(12) United States Patent
Cooper et al.

(10) Patent No.: US 11,926,600 B2
(45) Date of Patent: *Mar. 12, 2024

(54) SULFONYLUREAS AND SULFONYLTHIOUREAS AS NLRP3 INHIBITORS

(71) Applicant: Inflazome Limited, Dublin (IE)

(72) Inventors: Matthew Cooper, Cambridge (GB); David Miller, Cambridge (GB); Angus MacLeod, Cambridge (GB); Stephen Thom, Nottingham (GB); Stephen St-Gallay, Nottingham (GB); Jonathan Shannon, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/638,700

(22) PCT Filed: Aug. 15, 2018

(86) PCT No.: PCT/EP2018/072125
§ 371 (c)(1),
(2) Date: Feb. 12, 2020

(87) PCT Pub. No.: WO2019/034693
PCT Pub. Date: Feb. 21, 2019

(65) Prior Publication Data
US 2021/0122716 A1 Apr. 29, 2021

(30) Foreign Application Priority Data

| Aug. 15, 2017 | (GB) | 1713082 |
| Nov. 9, 2017 | (GB) | 1718563 |
| Dec. 22, 2017 | (GB) | 1721726 |
| Dec. 22, 2017 | (GB) | 1721735 |
| Jul. 4, 2018 | (GB) | 1810983 |

(51) Int. Cl.
| C07D 233/84 | (2006.01) |
| C07D 401/12 | (2006.01) |
| C07D 403/12 | (2006.01) |
| C07D 405/06 | (2006.01) |

(52) U.S. Cl.
CPC ......... C07D 233/84 (2013.01); C07D 401/12 (2013.01); C07D 403/12 (2013.01); C07D 405/06 (2013.01)

(58) Field of Classification Search
CPC .. C07D 233/84; C07D 401/12; C07D 403/12; C07D 405/06
See application file for complete search history.

(56) References Cited

U.S. PATENT DOCUMENTS

| 4,723,991 A | 2/1988 | Holyoke, Jr. et al. |
| 4,741,760 A | 5/1988 | Meyer et al. |
| 4,795,486 A | 1/1989 | Bohner et al. |
| 4,802,908 A | 2/1989 | Hillemann |
| 5,169,860 A | 12/1992 | Mohamadi et al. |
| 5,219,856 A | 6/1993 | Olson |
| 5,486,618 A | 1/1996 | Hagen et al. |
| 10,538,487 B2 | 1/2020 | O'Neill et al. |
| 11,130,731 B2 | 9/2021 | O'Neill et al. |
| 11,370,776 B2 | 6/2022 | Cooper et al. |
| 2002/0034764 A1 | 3/2002 | Gabel et al. |
| 2002/0077486 A1 | 6/2002 | Scarborough et al. |
| 2006/0069093 A1 | 3/2006 | Scarborough et al. |
| 2019/0119224 A1 | 4/2019 | Glick et al. |
| 2019/0192478 A1 | 6/2019 | Hacini-Rachinel |
| 2019/0337965 A1 | 11/2019 | Stafford et al. |
| 2020/0207780 A1 | 7/2020 | O'Neill et al. |
| 2020/0291003 A1 | 9/2020 | Cooper et al. |
| 2020/0299284 A1 | 9/2020 | O'Neill et al. |

(Continued)

FOREIGN PATENT DOCUMENTS

| CN | 104513239 A | 4/2015 |
| CN | 109432078 A | 3/2019 |

(Continued)

OTHER PUBLICATIONS

Alsante, et al., "Pharmaceutical Impurity Identification: A Case Study Using a Multidisciplinary Approach," Journal of Pharmaceutical Sciences, 93(9): 2296-2309, (2004).
Baldwin, et al., "Inhibiting the inflammasome: a chemical perspective," Journal of Medicinal Chemistry, 59(5): 1691-1710, (2016).
Booth, et al., "A new and efficient approach to the synthesis of 6-amidino-2-oxopurines," Journal of the Chemical Society Perkin Transactions, 1, 1(10): 1241-1251, (2001).
Braddock, et al., "Targeting IL-1 in Inflammatory Disease: New Opportunities for Therapeutic Intervention," Nature Reviews Drug Discovery, 3(4): 330-340, (2004).
CAS 1026500-66-2; STN Entry Date: Jun. 8, 2008; CN Compound Name: 2-Thiophenesulfonamide, 5-chloro-N-[[[2-ethyl-4-[7-fluoro-6-(methylamino)-1-oxo-2(1H)-isoquinoliny]-6-methylphenyl]amino]carbonyl]—(CA Index Name).

(Continued)

*Primary Examiner* — Brian E McDowell
(74) *Attorney, Agent, or Firm* — Alston & Bird LLP

(57) ABSTRACT

The present invention relates to sulfonylureas and sulfonylthioureas comprising a monocyclic imidazolyl group of formula (I):

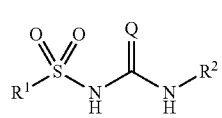

Formula (I)

wherein Q is selected from O or S, $R^1$ is an imidazolyl group, wherein the imidazolyl group is unsubstituted or substituted with one or more monovalent substituents, and $R^2$ is a cyclic group substituted at the α-position, wherein $R^2$ may optionally be further substituted. The present invention further relates to salts, solvates and prodrugs of such compounds, to pharmaceutical compositions comprising such compounds, and to the use of such compounds in the treatment and prevention of medical disorders and diseases, most especially by the inhibition of NLRP3.

12 Claims, No Drawings

(56) References Cited

U.S. PATENT DOCUMENTS

| | | |
|---|---|---|
| 2020/0317637 A1 | 10/2020 | Cooper et al. |
| 2020/0354341 A1 | 11/2020 | Cooper et al. |
| 2020/0361895 A1 | 11/2020 | Cooper et al. |
| 2021/0122739 A1 | 4/2021 | Cooper et al. |
| 2021/0130329 A1 | 5/2021 | Cooper et al. |
| 2021/0130359 A1 | 5/2021 | Cooper et al. |
| 2021/0163412 A1 | 6/2021 | Shannon et al. |
| 2021/0347737 A1 | 11/2021 | Cooper et al. |

FOREIGN PATENT DOCUMENTS

| | | |
|---|---|---|
| CN | 110151749 A | 8/2019 |
| DK | 2006 00313 L | 3/2006 |
| EP | 0125864 A1 | 11/1984 |
| EP | 0176304 A1 | 4/1986 |
| EP | 0177163 A2 | 4/1986 |
| EP | 0189069 A2 | 7/1986 |
| EP | 0204513 A2 | 12/1986 |
| EP | 0224842 A2 | 6/1987 |
| EP | 0249938 A2 | 12/1987 |
| EP | 0318602 A1 | 6/1989 |
| EP | 0610653 A1 | 8/1994 |
| EP | 0795548 A1 | 9/1997 |
| EP | 0885890 A1 | 12/1998 |
| EP | 0976742 A1 | 2/2000 |
| EP | 0987552 A2 | 3/2000 |
| EP | 1236468 A1 | 9/2002 |
| EP | 1270565 A1 | 1/2003 |
| EP | 1670749 A1 | 2/2005 |
| EP | 1995240 A1 | 11/2008 |
| EP | 2543670 A1 | 1/2013 |
| EP | 2781216 A1 | 9/2014 |
| EP | 2962692 A1 | 1/2016 |
| EP | 3272739 A1 | 1/2018 |
| FR | 2068472 A1 | 8/1971 |
| GB | 797474 A | 7/1958 |
| GB | 1146979 A | 3/1969 |
| GB | 1322980 A | 7/1973 |
| GB | 1713082.4 | 8/2018 |
| GB | 1718563.8 | 8/2018 |
| JP | S6045573 A | 12/1985 |
| JP | S6045573 A | 12/1985 |
| JP | 62-148482 A | 7/1987 |
| JP | 62-195376 A | 8/1987 |
| JP | 06199053 A | 7/1994 |
| JP | 06199054 A | 7/1994 |
| JP | 2000053649 A | 2/2000 |
| PL | 221813 B1 | 5/2016 |
| RU | 2022963 C1 | 11/1994 |
| WO | WO 91/10668 A1 | 7/1991 |
| WO | WO 92/04319 A1 | 3/1992 |
| WO | WO 93/04045 A1 | 3/1993 |
| WO | WO 93/04046 A1 | 3/1993 |
| WO | WO 97/11057 A1 | 3/1997 |
| WO | WO 98/032733 A1 | 7/1998 |
| WO | WO 00/55126 A2 | 9/2000 |
| WO | WO 2021/032588 A1 | 2/2001 |
| WO | WO 01/19390 A1 | 3/2001 |
| WO | WO 01/57037 A1 | 8/2001 |
| WO | WO 02/06246 A1 | 1/2002 |
| WO | WO 02/094176 A2 | 11/2002 |
| WO | WO 03/031194 A1 | 4/2003 |
| WO | WO 03/035076 A1 | 5/2003 |
| WO | WO 03/045400 A1 | 6/2003 |
| WO | WO 03/099805 A1 | 12/2003 |
| WO | WO 2004/039376 A1 | 5/2004 |
| WO | WO 2005/032488 A2 | 4/2005 |
| WO | WO 2005/035520 A1 | 4/2005 |
| WO | WO 2006/039212 A2 | 4/2006 |
| WO | WO 2006/085815 A1 | 8/2006 |
| WO | WO 2008/090382 A1 | 7/2008 |
| WO | WO 2009/065096 A1 | 5/2009 |
| WO | WO 2011/041694 A2 | 4/2011 |
| WO | WO 2015/069666 A1 | 5/2015 |
| WO | WO 2016/127924 A1 | 8/2016 |
| WO | WO 2016/131098 A1 | 8/2016 |
| WO | WO 2016/131098 A8 | 8/2016 |
| WO | WO 2016/138473 A1 | 9/2016 |
| WO | WO 2019/166623 A1 | 9/2016 |
| WO | WO 2017/106957 A1 | 6/2017 |
| WO | WO 2017/129897 A1 | 8/2017 |
| WO | WO 2017/140778 A1 | 8/2017 |
| WO | WO 2017/184604 A1 | 10/2017 |
| WO | WO 2017/184624 A1 | 10/2017 |
| WO | WO 2017/189652 A1 | 11/2017 |
| WO | WO 2018/015445 A1 | 1/2018 |
| WO | WO 2018/136890 A1 | 7/2018 |
| WO | WO 2018/152396 A1 | 8/2018 |
| WO | WO 2018/215818 A1 | 11/2018 |
| WO | WO 2019/008025 A1 | 1/2019 |
| WO | WO 2019/008029 A1 | 1/2019 |
| WO | WO 2019/023147 A1 | 1/2019 |
| WO | WO 2019/034686 A1 | 2/2019 |
| WO | WO 2019/034688 A1 | 2/2019 |
| WO | WO 2019/034690 A1 | 2/2019 |
| WO | WO 2019/034692 A1 | 2/2019 |
| WO | WO 2019/034693 A1 | 2/2019 |
| WO | WO 2019/034696 A1 | 2/2019 |
| WO | WO 2019/034697 A1 | 2/2019 |
| WO | WO 2019/068772 A1 | 4/2019 |
| WO | WO 2019/092170 A1 | 5/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166621 A1 | 9/2019 |
| WO | WO 2019/166624 A1 | 9/2019 |
| WO | WO 2019/166627 A1 | 9/2019 |
| WO | WO 2019/166628 A1 | 9/2019 |
| WO | WO 2019/166629 A1 | 9/2019 |
| WO | WO 2019/166632 A1 | 9/2019 |
| WO | WO 2019/166633 A1 | 9/2019 |
| WO | WO 2019/206871 A1 | 10/2019 |
| WO | WO 2019/211463 A1 | 11/2019 |
| WO | WO 2020/010118 A1 | 1/2020 |
| WO | WO 2020/010143 A1 | 1/2020 |
| WO | WO 2020/018970 A1 | 1/2020 |
| WO | WO 2020/035464 A1 | 2/2020 |
| WO | WO 2020/035465 A1 | 2/2020 |
| WO | WO 2020/035466 A1 | 2/2020 |
| WO | WO 2020/079207 A1 | 4/2020 |
| WO | WO 2020/086732 A1 | 4/2020 |
| WO | WO 2020/102096 A1 | 5/2020 |
| WO | WO 2020/104657 A1 | 5/2020 |
| WO | WO 2020/208249 A1 | 10/2020 |
| WO | WO 2021/032591 A1 | 2/2021 |
| WO | WO 2021/043966 A1 | 3/2021 |
| WO | WO 2021/165245 A1 | 8/2021 |

OTHER PUBLICATIONS

CAS 1026685-26-6; STN Entry Date: Jun. 9, 2008; CN Compound Name: 2-Thiophenesulfonamide, 5-chloro-N-[[[5-[6-(ethylamino)-7-fluoro-1-oxo-2(1H)-isoquinoliny]-3-methyl-2-pyridinyl]amino]carbonyl]—(CA Index Name).

CAS 1026892-76-1; STN Entry Date: Jun. 10, 2008; CN Compound Name: Benzamide, 2,3,4,5,6-pentafluoro-N-[2-[4-[[[[(2,3,4-trifluorophenyl)amino]carbonyl]amino]sulfonyl]phenyl]ethyl]—(CA Index Name).

CAS 1027977-57-6; STN Entry Date: Jun. 13, 2008; CN Compound Name: 2-Thiophenesulfonamide, 5-chloro-N-[[[4-[6-(ethylamino)-7-fluoro-1-oxo-2(1H)-isoquinoliny!]-2-(2-hydroxyethoxy)-6-methylphenyl]amino]carbonyl]—(CA Index Name).

CAS 104843-72-3 STN Entry Date:1986; CN Compound Name: 1H-Pyrazole-4-carboxylic acid, 5-[[[[(4,6-dimethyl-I-oxido-2-pyrimidinyl)amino]carbonyl]amino]sulfonyl]-1-(2-pyridinyl)-, ethyl ester (CA Index Name).

CAS 123807-74-8; STN Entry Date: 1995; CN Compound Name: 2H-1,2,5-Thiadiazino[5,6-a]indole-10-sulfonamide, N-[[(3-cyano-4,6-dimethyl-2-pyridinyl)amino]carbonyl]-2-methyl-1,1-dioxide (CA Index Name).

CAS 1332606-77-5; STN Entry Date: Sep. 16, 2011; CN Compound Name: 2-(3-(3-Amino-4-(tert-butoxycarbonyl)phenylsulfonyl)ureido)-4-chlorobenzoic acid.

(56) References Cited

OTHER PUBLICATIONS

CAS 1347649-72-2; STN Entry Date: Dec. 2, 2001; CN Compound Name: 2-Thiophenesulfonamide, 5-chloro-N-H[4-[7-fluoro-6-(methylamino)-1-oxo-2(1H)-isoquinolinyl]-2-(methoxymethoxy)phenyl]amino]carbonyl]—(CA Index Name).
CAS 170648-58-5; STN Entry Date: 1995; CN Compound Name: Acetamide, N-[5-[[[[(2,3-dihydro-1,5-dimethyl-3-oxo-2-phenyl-1H-pyrazol-4-yl)amino]carbonyl]amino]sulfonyl]-1,3,4-thiadiazol-2-yl]—(CA Index Name).
CAS 36628-63-4; STN Entry Date: 1972; CN Compound Name: Benzamide, N-[2-[5-[[[(bicyclo[2 .2]oct-5-en-2-ylamino)carbonyl]amino]sulfonyl]-2-thienyl]ethyl]-5-chloro-2-methoxy—(CA Index Name).
CAS 438013-57-1; STN Entry Date: Jul. 10, 2002; CN Compound Name: 2-Thiophenesulfonamide, 5-methyl-N-[(1-naphthalenylamino)carbonyl]—(CA Index Name).
CAS 663215-37-0; STN Entry Date: Mar. 15, 2004; CN Compound Name: 1H-1,2,4-Triazole-1-carboxamide, N-(2-chlorophenyl)-5-[[[[(2-chlorophenyl)amino]carbonyl]amino]sulfony]—(CA Index Name).
CAS 84884-90-2; STN Entry Date: 1983; CN Compound Name: Acetamide, N-15-[[[[(2-methylphenyl)amino)thioxomethyl]amino]sulfonyl]-1,3,4-thiadiazol-2-yl]—(CA Index Name).
CAS 907958-32-1; STN Entry Date: Sep. 20, 2006; CN Compound Name: Acetamide, N-[5-[[[[(2,5-dioxo-4-imidazolidinyl)amino]carbonyl]amino]sulfonyl]-4-methyl-2-thiazolyl]—(CA Index Name).
CAS 959378-15-5; STN Entry Date: Dec. 21, 2007; CN Compound Name: Benzo[b]thiophene-3-carboxylic acid,4,5,6,7-tetrahydro-6,6-dimethyl-2-[[[[(2-methyl-1H-imidazol-1-yl)sulfonyl]amino]carbonyl]amino]-, ethyl ester (CA Index Name).
CAS 959664-76-7; STN Entry Date: Dec. 28, 2007; CN Compound Name: Benzo[b]thiophene-3-carboxylic acid, 4,5,6,7-tetrahydro-6,6-dimethyl-2-[[[[(5-methyl-1H-pyrazol-1-yl)sulfonyl]amino]carbonyl]amino]-, ethyl ester (CA Index Name).
CAS RN 1026469-15-7; STN Entry Date: Jun. 8, 2008; CN Compound Name: 2-Thiophenesulfonamide, 5-chloro-N-[[[2-(cyclopropyloxy)-4-[7-fluoro-6-(methylamino)-1-oxo-2(1H)-isoquinolinyl]phenyl]amino]carbonyl]—(CA Index Name).
CAS RN 84884-72-0; STN Entry Date: 1983; CN Compound Name: Acetamide, N-[5-[[[[(2-chlorophenyl)amino]carbonyl]amino]sulfonyl]-1,3,4-thiadiazol-2-yl]—(Ca Index Name).
CAS RN 84884-75-3; STN Entry Date:1983; CN Compound Name: Acetamide, N-(5-[[[[(2-bromophenyl)amino]carbonyl]amino]sulfonyl]-1,3,4-thiadiazol-2-yl]—(CA Index Name).
CAS RN 84884-76-4; STN Entry Date: 1983; CN Compound Name: Acetamide, N-[5-[[[[(2-methylphenyl)amino]carbonyl]amino]sulfonyl]-1,3,4-thiadiazol-2-yl]—(CA Index Name).
CAS RN 84884-82-2; STN Entry Date: 1983; CN Compound Name: Acetamide, N-[5-[[[[1-naphthalenylamino)carbonyl]amino]sulfony]-1,3,4-thiadiazol-2-yl]—(CA Index Name).
Coll, et al., "A small-molecule inhibitor of the NLRP3 inflammasome for the treatment of inflammatory diseases," Nature Medicine, 21(3): 248-255, (2015).
Cubrilovic, et al., "Determination of Protein-Ligand Binding Constants of a Cooperatively Regulated Tetrameric Enzyme Using Electrospray Mass Spectrometry," ACS Chemical Biology, 9(1): 218-226, (2014).
Dias, et al., "Synthesis of new imidazo[4,5-d][1,3]diazepine derivatives from 5-amino-4-(cyanoformimidoyl)imidazoles," Journal of Heterocyclic Chemistry, 33(3): 855-862, (1996).
El-Telbany, et al., "Synthesis of Thiophenesulphonylureas and Thioureas Structurally Related to Certain Oral Hypoglycemic drugs. Part I," Egypt Journal of Pharmaceutical Science, 16(4): 397-401, (1975).

Fleming, et al., "Novel axially chiral bis-arylthiourea-based organocatalysts for asymmetric Friedel-Crafts type reactions," Tetrahedron Letters, 47(39): 7037-7042, (2006).
Groß, et al. "K+ Efflux-Independent NLRP3 Inflammasome Activation by Small Molecules Targeting Mitochondria," Immunity, 45(4):761-773, (2016).
Hebeisen, et al., "Orally active aminopyridines as inhibitors of tetrameric fructose-1,6-bisphosphatase," Bioorganic & Medicinal Chemistry Lettters, 21(11): 3237-3242, (2011).
Hill, et al., "Dual Action Sulfonylureas: NLRP3 Inhibition and Insulin Secretion," 1st Queensland Annual Chemistry Symposium, Poster P20, Nov. 25, 2016 (and accompanying programme).
Hill, et al., "Sulfonylureas as Concomitant Insulin Secretagogues and NLRP3 Inflammasome Inhibitors," Chem Med Chem, 12(17): 1449-1457, (2017).
Holland, "Preparation of some additional sulfonylureas," Journal of Organic Chemistry, 26(5): 1662-1665, (1961).
Hutton, et al, "The NLRP3 inflammasome in kidney disease and autoimmunity," Nephrology, 21(9): 736-744, (2016).
Kazuto, et al., "Design, synthesis and biological activity of novel non-peptidyl endothelin converting enzyme inhibitors, 1-phenyl-tetrazole-formazan analogues," Bioorganic & Medicinal Chemistry Letters, 12(9): 1275-1278, (2002).
Khelili, et al., "Synthesis and vasodilator effects of 3- and 7-sulfonylurea-1,2,4-benzothiadiazin-1,1-dioxides on rat aorta," Bioorganic & Medicinal Chemistry, 3(5): 495-503, (1995).
Khuntwal, et al., "Credential role of van der waal volumes and atomic masses in modeling Hepatitis C virus NS5B polymerase inhibition by tetrahydrobenzo-thiophenes using SVM and MLR aided QSAR studies," Current Bioinformatics, 8(4): 465-471, (2013).
Kim, et al., "Role for NLRP3 Inflammasome-mediated, IL-1β-Dependent Responses in Severe, Steroid-Resistant Asthma," 196(3): 283-297, (2017).
Krishnan, et al., "Inflammasome activity is essential for one kidney/deoxycorticosterone acetate/salt-induced hypertension in mice," British Journal of Pharmacology, 173(4): 752-765, (2016).
Laliberte, et al., "Glutathione S-transferase omega 1-1 is a target of cytokine release inhibitory drugs and may be responsible for their effect on interleukin-1B posttranslational processing," Journal of Biological Chemistry, 278(19): 16567-16578, (2003).
Laporte, et al., "Tetrahydrobenzothiophene inhibitors of hepatitis C virus NS5B polymerase," Bioorganic & Medicinal Chemistry Letters, 16(1): 100-103, (2006).
Lerner, et al. "*Mycobacterium tuberculosis* replicates within necrotic human macrophages," Journal of Cell Biology, 216(3): 583-594, (2017).
Li, et al., "Discovery of the first SecA inhibitors using structure-based virtual screening," Biochemical and Biophysical Research Communications, 368(4): 839-845, (2008).
Luckhurst, et al., "A convenient synthesis of sulfonylureas from carboxylic acids and sulfonamides via an in situ Curtius rearrangement," Tetrahedron Letters, 48(50): 8878-8882, (2007).
Ludwig-Portugall, et al., "An NLRP3-specific inflammasome inhibitor attenuates crystal-induced kidney fibrosis in mice," Kidney International, 90(3): 525-539, (2016).
Mokhtar, et al., "Synthesis of nitrogenous compounds. Part III," Pakistan Journal of Scientific and Industrial Research, 34(1): pp. 9-15, (1991).
Monnerat, et al.,"Macrophage-dependent IL-1β production induces cardiac arrhythmias in diabetic mice," Nature Communications, 7(13344): 1-15, (2016).
Mridha, et al., "NLRP3 inflammasome blockade reduces liver inflammation and fibrosis in experimental NASH in mice," Journal of Hepatology, 66(5): 1037-1046, (2017).
Ouf, et al., "Sulphonyl Ureas and Thioureas of 1,3,4-Thiodiazole to be Tested as Hypoglycomic Agents," Egyptian Journal of Pharmaceutical Sciences, 21(3-4): 189-198, (1980).
Ouf, et al., "Thiophene sulphonylureas structurally related to antidiabetic drugs," Journal of Drug Research Egypt, 6(2): 123-129, (1974).
Pacini, et al., "2-(3-Thienyl)-5,6-dihydroxypyrimidine-4-carboxylic acids as inhibitors of HCV NS5B RdRp," Bioorganic & Medicinal Chemistry Letters, 19(21): 6245-6249, (2009).

(56) References Cited

OTHER PUBLICATIONS

Pinar, et al., "PB1-F2 Peptide Derived from Avian Influenza A Virus H7N9 Induces Inflammation via Activation of the NLRP3 Inflammasome," Journal of Biological Chemistry, 292(3): 826-836, (2017).
Proks, et al., "Sulfonylurea stimulation of insulin secretion," Diabetes, 51(3): S368-S376, (2002).
Rotroff, et al., "Predictive Endocrine Testing in the 21st Century Using in Vitro Assays of Estrogen Receptor Signaling Responses," Environmental Science & Technology, 48(15): 8706-8716, (2014).
Sączewski, et al., "Synthesis of Novel Aryl(heteroaryl)sulfonyl Ureas of Possible Biological Interest," Molecules, 15(3): 1113-1126, (2010).
Salla, et al., "Identification, Synthesis, and Biological Evaluation of the Major Human Metabolite of NLRP3 Inflammasome Inhibitor MCC950," ACS Medicinal Chemistry Letters, 7(12): 1034-1038, (2016).
Sarges, et al., "Sulfamylurea hypoglycemic agents. 6. High potency derivatives," Journal of Medicinal Chemistry, 19(5): 695-709, (1976).
Shah, et al., "Analysis of Pfizer Compounds in EPA's ToxCast Chemicals-Assay Space," Chemical Research in Toxicology, 2014, 27(1), 86-98: (2014).
Shah, et al., "Setting Clinical Exposure Levels of Concern for Drug-Induced Liver Injury (DILI) Using Mechanistic in vitro Assays," Toxicological Sciences, 147(2): 500-514, (2015).
Sipes, et al., "Profiling 976 ToxCast Chemicals across 331 Enzymatic and Receptor Signaling Assays," Chemical Research in Toxicology, 26(6): 878-895, (2013).
Urban, et al., "Novel Synthesis of 1-(1,2,3,5,6,7-Hexahydro-s-indacen-4-yl)-3-[4-(1-hydroxy-1-methyl-ethyl)-furan-2-sulfonyl]urea, an Anti-inflammatory Agent," Synthetic Communications, 33(12): 2029-2043, (2003).
Wambaugh, et al., "High-Throughput Models for Exposure-Based Chemical Prioritization in the ExpoCast Project," Environmental Science & Technology, 47(15): 8479-8488, (2013).
Waterman, et al. "Improved Protocol and Data Analysis for Accelerated Shelf-Life Estimation of Solid Dosage Forms," Pharmaceutical Research, 24(4): 780-790, (2007).
Youssef, et al., "N1, N3-Diaryl sulfonylureas as possible anticancer agents," Alexandria Journal of Pharmaceutical Sciences, 8(3): 223-225, (1994).
Youssef, et al., "Synthesis of sulofenur analogues as antitumour agents: part II," Medicinal Chemistry Research, 11(9): 481-503, (2002).
Zhen, et al., "Recent advances in discovery and development of promising therapeutics against Hepatitis C virus NS5B RNA-dependent RNA polymerase," Mini Reviews in Medicinal Chemistry, 5(12): 1103-1112, (2005).
GB Application No. GB1713082.4 Search Report under Section 17(5) dated Apr. 30, 2018.
GB Application No. GB1721727.4 Search Report under Section 17(5) dated Sep. 17, 2018.
GB Application No. GB1721729.0 Search Report under Section 17(5) dated Aug. 30, 2018.
GB Application No. GB1721731.6 Search Report under Section 17(5) dated Sep. 3, 2018.
GB Application No. GB1721732.4 Search Report under Section 17(5) dated Sep. 3, 2018.
GB Application No. GB1721735.7 Search Report under Section 17(5) dated Aug. 30, 2018.
GB Application No. GB1721736.5 Search Report under Section 17(5) dated Aug. 30, 2018.
GB Application No. GB1803391.0 Search Report under Section 17(5) dated Oct. 16, 2018.
GB Application No. GB1803392.8 Search Report under Section 17(5) dated Oct. 16, 2018.
WIPO Application No. PCT/EP2018/072111, PCT International Preliminary Report on Patentability dated Feb. 27, 2020.
WIPO Application No. PCT/EP2018/072111, PCT International Search Report and Written Opinion of the International Searching Authority dated Nov. 6, 2018.
WIPO Application No. PCT/EP2018/072115, PCT International Preliminary Report on Patentability dated Feb. 27, 2020.
WIPO Application No. PCT/EP2018/072115, PCT International Search Report and Written Opinion of the International Searching Authority dated Oct. 24, 2018.
WIPO Application No. PCT/EP2018/072119, PCT International Preliminary Report on Patentability dated Feb. 27, 2020.
WIPO Application No. PCT/EP2018/072119, PCT International Search Report and Written Opinion of the International Searching Authority dated Dec. 11, 2018.
WIPO Application No. PCT/EP2018/072123, PCT International Preliminary Report on Patentability dated Feb. 27, 2020.
WIPO Application No. PCT/EP2018/072123, PCT International Search Report and Written Opinion of the International Searching Authority dated Nov. 14, 2018.
WIPO Application No. PCT/EP2018/072125, PCT International Preliminary Report on Patentability dated Feb. 27, 2020.
WIPO Application No. PCT/EP2018/072125, PCT International Search Report and Written Opinion of the International Searching Authority dated Oct. 22, 2018.
WIPO Application No. PCT/EP2018/080737, PCT International Preliminary Report on Patentability dated May 22, 2020.
WIPO Application No. PCT/EP2018/080737, PCT International Search Report and Written Opinion of the International Searching Authority dated Jan. 30, 2019.
WIPO Application No. PCT/EP2018/080739, PCT International Preliminary Report on Patentability dated May 22, 2020.
WIPO Application No. PCT/EP2018/080739, PCT International Search Report and Written Opinion of the International Searching Authority dated Jan. 25, 2019.
WIPO Application No. PCT/EP2018/080746, PCT International Preliminary Report on Patentability dated May 22, 2020.
WIPO Application No. PCT/EP2018/080746, PCT International Search Report and Written Opinion of the International Searching Authority dated Jan. 25, 2019.
WIPO Application No. PCT/EP2019/055127, PCT International Search Report and Written Opinion of the International Searching Authority dated Apr. 24, 2019.
WIPO Application No. PCT/IB2017/053059, PCT International Preliminary Report on Patentability dated Dec. 5, 2019.
WIPO Application No. PCT/IB2017/053059, PCT International Search Report and Written Opinion of the International Searching Authority dated Aug. 8, 2017.
U.S. Appl. No. 16/638,704, Requirement for Restriction/Election dated Apr. 29, 2021.
U.S. Appl. No. 16/638,707, Requirement for Restriction/Election dated May 13, 2021.
Brown, "Bioisosteres in Medicinal Chemistry" Published by Wiley-VCH Verlag Gmbh & Co. KGaA, Weinheim, Germany, (2012).
CAS 210826-40-7; STN Entry Date: Sep. 3, 1998; CN Compound Name: 2-Furansulfonamide, N-[[(1,2,3,5,6,7-hexahydro-s-indacen-4-yl)amino]carbonyl]-4-(1-hydroxy-1-methylethyl)- (Ca Index Name).
Coll, "In their own words . . . 2012 IEIIS Young Investigator Awardees," Endotoxin Newsletter, vol. 19, No. 1, Editor Jerold Weiss, PhD, Dept. of Internal Medicine, University of Iowa, (Oct. 2013).
Coll, et al., "Correction: The Cytokine Release Inhibitory Drug CRID3 Targets ASC Oligomerisation in the NLRP3 and AIM2 Inflammasomes," PloS One, vol. 6, Issue 12, e29539, (Feb. 27, 2013).
Coll, et al., "Supporting Information: The Cytokine Release Inhibitory Drug CRID3 Targets ASC Oligomerisation in the NLRP3 and AIM2 Inflammasomes," PloS One, vol. 6, Issue 12, e29539, (Feb. 27, 2013).
Coll, et al., "The Cytokine Release Inhibitory Drug CRID3 Targets ASC Oligomerisation in the NLRP3 and AIM2 Inflammasomes," PloS One, vol. 6, Issue 12, e29539, (Dec. 2011).
Dalvie, et al., "Biotransformation Reactions of Five-Membered Aromatic Heterocyclic Rings," Chem. Res. Toxicol., vol. 15, No. 3, pp. 269-299 (2002).
Dempsey, et al., "Cytokine release inhibitor drug, CRID3, inhibits the NLRP3 inflammasome in glia," Journal of Neuroimmunology, vol. 275(1-2), p. 147, (2014).

(56) References Cited

OTHER PUBLICATIONS

Email from CAS Customer Center <help@cas.org>, Subject: RE: Case #00345503: question of indexing, 218-Sent: Oct. 9, 2020.
Febbraio, "Role of interleukins in obesity: implications for metabolic disease," Trends in Endocrinology and Metabolism, vol. 25, No. 6, pp. 312-319, (Jun. 2014).
Guo, et al., "Inflammasomes: mechanism of action, role in disease, and therapeutics," Nature Medicine, vol. 21, No. 7, pp. 677-687, (Jul. 2015).
Haneklaus, et al., "Modulatory mechanisms controlling the NLRP3 inflammasome in inflammation: recent developments," Current opinion in immunology, 25, (1), pp. 40-45, (2013).
Mullen, et al., "Pattern recognition receptors as potential therapeutic targets in inflammatory rheumatic disease," Arthritis Research & Therapy, 17:122, (2015).
St Jean, et al., "Mitigating Heterocycle Metabolism in Drug Discovery," Journal of Medicinal Chemistry, 55, pp. 6002-6020, (2012).
Stocks, et al., "On Chemistry, On Medical Chemistry," Published in Great Britain by Sci-Ink Limited, ISBN 978-0-9550072-3-1, pp. 214-215, (2007).
WIPO Application No. PCT/EP2019/055127, PCT International Preliminary Report on Patentability dated Sep. 17, 2020.
U.S. Appl. No. 16/638,648, Requirement for Restriction/Election dated Apr. 20, 2021.
U.S. Appl. No. 16/761,993, Requirement for Restriction/Election dated Apr. 9, 2021.
Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.
Banker, et al., Prodrugs, Modern Pharmaceutics, 3rd edition, Revised and Expanded, pp. 451 and 596, (1995).
Belikov, et al., "The interconnection between chemical structure, properties of substances and their effect on the body", MEDpress-inform, Pharmaceutical Chemistry, Text Book, 4th Edition, Moscow, Chap. 2.6, 27-29, (2007), Brief statement of relevance.
Bundgaard, "Design of Prodrugs," Chapter1, p. 1, (1985).
Disease—Wikipedia, retrieved from the internet on Jan. 5, 2022 at: https://en.wikipedia.org/wiki/Disease.
Ettmayer, et al., "Perspective, Lessons Learned from Marketed and Investigational Prodrugs," Journal of Medicinal Chemistry, vol. 47, No. 10, 2393-2404, (May 6, 2004).
Himiceskij, Chemical Encyclopedia, (1983), p. 130-131, Brief statement of relevance.
Jordan, "Tamoxifen: A Most Unlikely Pioneering Medicine," Nature Reviews, Drug Discovery, vol. 2, 205-213, (Mar. 2003).
Parajuli, et al., "Prodrug as a novel approach of drug delivery—a review," Journal of Drug Delivery & Therapeutics, 5(3), pp. 5-9, (2015).
Silverman, "The Organic Chemistry of Drug Design and Drug Action," Prodrugs and Drug Delivery Stystem, The Organic Chemistry of Drug Design and Drug Action, Chapter 8, pp. 352-400, (1992).
Solvation—Wikipedia, retrieved from the internet on Jan. 5, 2022 at: https://en.wikipedia.org/wiki/Solvation.
Stella, "Prodrugs as therapeutics," Xpert Opin. Ther. Patients, 14(3): 277-280, (2004).
Testa, "Prodrug research: futile or fertile," Biochemical Pharmacology, 68, 2097-2106, (2004).
Zawilska, et al., "Prodrugs: a challenge for the drug development," Pharmacological reports: PR, vol. 65, No. 1, pp. 1-14, (Apr. 2013).
RU Application No. 2020110219/04(017079) Office Action and Search Report dated Feb. 15, 2022, English tranlsation of office action.
U.S. Appl. No. 16/638,648, Non-Final Office Action dated Oct. 12, 2021.
U.S. Appl. No. 16/638,707, Non-Final Office Action dated Oct. 15, 2021.
U.S. Appl. No. 16/761,993, Non-Final Office Action dated Aug. 16, 2021.
U.S. Appl. No. 16/762,000, Requirement for Restriction/Election dated Nov. 1, 2021.
U.S. Appl. No. 16/977,241, Requirement for Restriction/Election dated Nov. 30, 2021.
Belikov, et al., "MEDpress-inform," Pharmaceutical Chemistry, Text Book, 4th Edition, Moscow, 622 pages, 11, 27-29, (2007), Brief statement of relevance.
Gavrilov, et al., Pharmaceutical Technology, Preparation of Medicaments, Text Book, Moscow Publishing group "GEOTAR-Media", 2010, 624, p. 20, Brief statement of relevance.
Guidelines for Conducting Preclinical Drug Studies. Part one. M.: Grif and K, 2012, 944 p., ed. Mironova A.N, Brief statement of relevance.
Han, "Targeted Prodrug Design to Optimize Drug Delivery," AAPS Pharmsci, 2 (1) article 6, 1-11, (2000).
Mashkovskiy, "Medicaments," Moscow, "Medicine", 1993, chapter 1, p. 8, Brief statement of relevance.
Zhulenko, et al., "Pharmacology", Moscow: KolosS, p. 34-35, (2008), Brief statement of relevance.
U.S. Appl. No. 16/638,648, Final Office Action dated May 27, 2022.
U.S. Appl. No. 16/638,707, Notice of Allowance and interview Summary dated Apr. 21, 2022.
U.S. Appl. No. 16/761,993, Non-Final Office Action dated Apr. 6, 2022.
U.S. Appl. No. 16/762,000, Non-Final Office Action dated Apr. 4, 2022.
U.S. Appl. No. 16/977,241, Non-Final Office Action dated Jun. 13, 2022.
U.S. Appl. No. 16/638,704, Final Office Action dated Jul. 8, 2022.
Dorwald, "Side Reactions in Organic Synthesis, A Guide to Successful Synthesis Design," Wiley-VCH, 11 pages, (2005).
U.S. Appl. No. 16/638,648, Notice of Allowance dated Oct. 18, 2022.
U.S. Appl. No. 16/638,704, Non-Final Office Action dated Dec. 30, 2022.
U.S. Appl. No. 16/638,707, Notice of Allowance dated Sep. 7, 2022.
U.S. Appl. No. 16/761,993, Non-Final Office Action dated Oct. 12, 2022.
U.S. Appl. No. 16/762,000, Final Office Action dated Nov. 15, 2022.
U.S. Appl. No. 16/977,241, Notice of Allowance dated Jan. 6, 2023.
U.S. Appl. No. 16/638,648, Supplemental Notice of Allowance dated Jan. 20, 2023.
Hamarsheh, et al., "NLPR3 Inflammasome Activation in Cancer: A Double-edged Sword," Frontiers in Immunology, 11:1444, (Jul. 2020).
Kim, et al., "NLPR3 Inflammasome and Host Protection against Bacterial Infection," J. Korean Med Sci, 28: 1415-1423, (Oct. 2013).
Meanwell, "Fluorine and Fluorinated Motifs in the Design and Application of Bioisosteres for Drug Design," J. Med. Chem, 61, 5822-5880, (Feb. 2018).
Moossavi, et al., "Role of the NLRP3 inflammasome in cancer," Molecular Cancer, 17:158, (2018).
Mortimer, et al., "NLRP3 inflammasome inhibition is disrupted in a group of auto-inflammatory disease CAPS mutations," Nature Immunology, vol. 17, No. 10, 1176-1186, (Oct. 2016).
Shao, et al,. "Targeting NLRP3 Inflammasome in the Treatment fo CNS Diseases," Front. Mol Neurosci, 11:320, (Sep. 2018).
Sita, et al., "NLRP3 and Infections: β-Amyloid in Inflammasome beyond Neurodegeneration," Int. J. Mol. Sci, 22, 6984, (Jun. 2021).
Song, et al., "NLRP3 Inflammasome in Neurological Diseases, from Functions to Therapies," Front. Cell. Neurosci 11:63, doi: 10.3389/Incel.2017.00063, (Mar. 2017).
Zhao, et al., "NLRP3 Inflammasome—A Key Player in Antiviral Responses," Frontiers in Immunology, vol. 11, Article 211, (Feb. 2020).
EP 19708309.0 Commuication pursuant to Article 94(3) dated Mar. 23, 2023.
U.S. Appl. No. 16/761,993, Final Office Action dated Feb. 28, 2023.
U.S. Appl. No. 16/762,000, Non-Final Office Action dated Apr. 26, 2023.
U.S. Appl. No. 16/977,241, Non-Final Office Action dated Apr. 25, 2023.

(56) References Cited

OTHER PUBLICATIONS

U.S. Appl. No. 16/761,993, Non-Final Office Action dated Jul. 17, 2023.
U.S. Appl. No. 16/638,704, Final Office Action dated Oct. 3, 2023.
U.S. Appl. No. 16/977,241, Notice of Allowance dated Sep. 13, 2023.
U.S. Appl. No. 16/762,000, Non-Final Office Action dated Dec. 26, 2023.

SULFONYLUREAS AND SULFONYLTHIOUREAS AS NLRP3 INHIBITORS

CROSS-REFERENCE TO RELATED APPLICATION

This application is the US national stage of PCT/EP2018/072125 filed Aug. 15, 2018, which claims priority to GB 1713082.4 filed Aug. 15, 2017; GB 1718563.8 filed Nov. 9, 2017; GB 1721726.6 filed Dec. 22, 2017; GB 1721735.7 filed Dec. 22, 2017; and GB 1810983.5 filed Jul. 4, 2018.

FIELD OF THE INVENTION

The present invention relates to sulfonylureas and sulfonylthioureas comprising a monocyclic imidazolyl group, and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatoiy process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NO-MID) are caused by gain-of-function mutations in NLRP3, thus defining NLRP3 as a critical component of the inflammatoiy process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al, J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/136890 A1 and WO 2018/015445 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

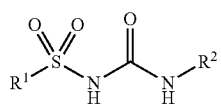

Formula (I)

wherein:
  Q is selected from O or S;
  $R^1$ is an imidazolyl group, wherein the imidazolyl group is unsubstituted or substituted with one or more monovalent substituents; and
  $R^2$ is a cyclic group substituted at the α-position, wherein $R^2$ may optionally be further substituted.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, z-propyl, n-butyl, z-butyl, i-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, l-butenyl, 2-butenyl, 1-pentenyl, l-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

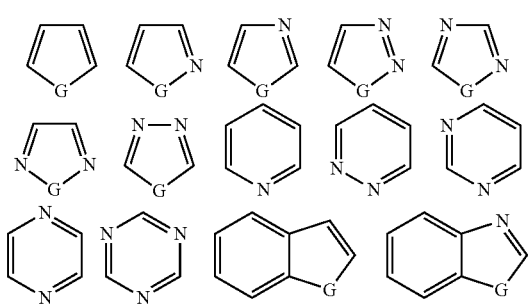

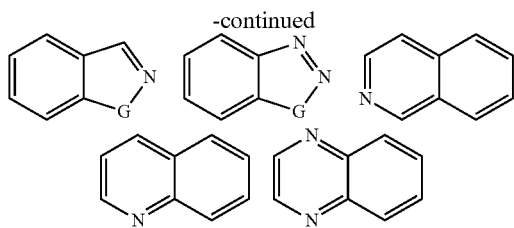

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or
(ii) any two hydrogen atoms attached to the same atom may optionally be replaced by a n-bonded substituent independently selected from oxo (=O), =S, =NH or =NR$^\beta$; and/or
(iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;
wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and
wherein each —R$^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two or three —R$^\beta$ attached to the same nitrogen atom may, together with the nitrogen atom to which they are attached, form a $C_2$-$C_7$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), —CO($C_1$-$C_4$ alkyl), —CO($C_1$-$C_4$ haloalkyl), —COO($C_1$-$C_4$ alkyl), —COO($C_1$-$C_4$ haloalkyl), halo, —OH, —NH$_2$, —CN, —OCH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)RP group, what is intended is:

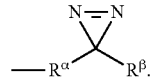

Typically, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N $(R^\beta)_2$; —NH—$R^\alpha$—OH; —NH—$R^\alpha$—$OR^\beta$; —NH—$R^\alpha$—$NH_2$; —NH—$R^\alpha$—$NHR^\beta$; —NH—$R^\alpha$—$N(R^\beta)_2$; —$NR^\beta$—$R^\alpha$—OH; —$NR^\beta$—$R^\alpha$—$OR^\beta$; —$NR^\beta$—$R^\alpha$—$NH_2$; —$NR^\beta$—$R^\alpha$—$NHR^\beta$; or —$NR^\beta$—$R^\alpha$—$N(R^\beta)_2$; and/or (ii) any two hydrogen atoms attached to the same carbon atom may optionally be replaced by a π-bonded substituent independently selected from oxo (=O), =S, =NH or =$NR^\beta$; and/or (iii) any two hydrogen atoms attached to the same or different atoms, within the same optionally substituted group or moiety, may optionally be replaced by a bridging substituent independently selected from —O—, —S—, —NH—, —$N(R^\beta)$— or —$R^\alpha$—;
wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_4$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), halo, —OH, —$NH_2$, —CN, —C≡CH, oxo (=O), or 4- to 6-membered heterocyclic group.

More typically, in an optionally substituted group or moiety:

(i) each hydrogen atom may optionally be replaced by a group independently selected from halo; —CN; —$R^\beta$; —OH; —$OR^\beta$; —$R^\alpha$-halo; —$R^\alpha$—CN; —$R^\alpha$—$R^\beta$; —$R^\alpha$—OH; —$R^\alpha$—$OR^\beta$; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$; and/or (ii) any two hydrogen atoms attached to the same carbon atom may optionally be replaced by a n-bonded substituent independently selected from oxo (=O), =S, =NH or =$NR^\beta$; and/or (iii) any two hydrogen atoms attached to the same or different atoms, within the same optionally substituted group or moiety, may optionally be replaced by a bridging substituent independently selected from —O—, —S—, —NH—, —$N(R^\beta)$— or —$R^\alpha$—;
wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —R$^\beta$ may optionally be substituted with one or more C$_4$-C$_4$ alkyl, halo, —OH, or 4- to 6-membered heterocyclic group.

Alternately in the optionally substituted groups or moieties defined immediately above, each —R$^\beta$ may be independently selected from a C$_1$-C$_6$ alkyl, C$_2$-C$_6$ alkenyl, C$_2$-C$_6$ alkynyl or C$_2$-C$_6$ cyclic group, or any two —R$^\beta$ attached to the same nitrogen atom may, together with the nitrogen atom to which they are attached, form a C$_2$-C$_7$ cyclic group, wherein any —R$^\beta$ may optionally be substituted with one or more C$_1$-C$_4$ alkyl, C$_1$-C$_4$ haloalkyl, halo, —OH, or 4- to 6-membered heterocyclic group.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N(R$^\beta$)—, —N(O)(R$^\beta$)—, —N$^+$(R$^\beta$)$_2$— or —R$^\alpha$—) of an optionally substituted group or moiety (e.g. R$^1$) must only be attached to the specified group or moiety and may not be attached to a second group or moiety (e.g. R$^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

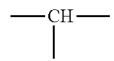

is replaced by

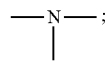

—CH$_2$— is replaced by —NH—, —O— or —S—;
—CH$_3$ is replaced by —NH$_2$, —OH or —SH;
CH= is replaced by —N=;
CH$_2$= is replaced by NH=, O= or S=; or
CH≡ is replaced by N≡;

provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:

—CH$_2$— is replaced by

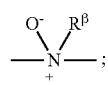

or

—CH$_2$— is replaced by

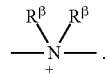

In the context of the present specification, unless otherwise stated, a C$_x$-C$_y$ group is defined as a group containing from x to y carbon atoms. For example, a C$_1$-C$_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are not to be counted as carbon atoms when calculating the number of carbon atoms in a C$_x$-C$_y$ group. For example, a morpholinyl group is to be considered a C$_4$ heterocyclic group, not a C$_6$ heterocyclic group.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group —(C=O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

As stated, R$^1$ is an imidazolyl group, wherein the imidazolyl group is unsubstituted or substituted with one or more monovalent substituents.

For the purposes of the present specification, where it is stated that a substituent, group or moiety "is a" specific group, it is to be understood that the specific group is directly attached to the remainder of the molecule, i.e. via a covalent bond with no intervening atom(s) or groups being present. Thus, in the first aspect of the invention, where it is stated that "$R^1$ is an imidazolyl group" it is to be understood that a ring atom of the 5-membered ring of the imidazolyl group is directly attached to the sulfur atom of the sulfonyl group, with no intervening atom(s) or groups being present. Similarly, where it is stated that "$R^2$ is a cyclic group", it is to be understood that a ring atom of the cyclic group is directly attached to the nitrogen atom of the (thio)urea group, with no intervening atom(s) or groups being present. For the avoidance of doubt, $R^1$ is not attached to the sulfur atom of the sulfonyl group via any optional substituent.

Since the imidazolyl group of $R^1$ is unsubstituted or substituted with one or more monovalent substituents, it will be understood that the imidazolyl group is monocyclic. Thus, for example, the imidazolyl group of $R^1$ does not form part of a bicyclic fused ring structure. The monocyclic imidazole group of $R^1$ may however be substituted with one or more monovalent substituents, where said monovalent substituents may be or may include cyclic groups.

In one embodiment, $R^1$ is an imidazol-4-yl group. In such an embodiment, the compound may be a compound of formula (Ia):

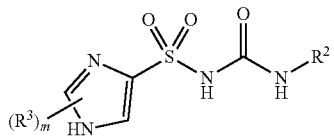

Formula (Ia)

wherein:
$R^2$ is as described herein;
$R^3$ is any optional monovalent substituent as described herein; and
m is 0, 1, 2 or 3.

In another embodiment, $R^1$ is an imidazol-5-yl group. In such an embodiment, the compound may be a compound of formula (Ib):

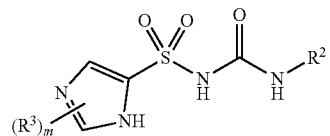

Formula (Ib)

wherein:
$R^2$ is as described herein;
$R^3$ is any optional monovalent substituent as described herein; and
m is 0, 1, 2 or 3.

In yet another embodiment, $R^1$ is an imidazol-2-yl group. In such an embodiment, the compound may be a compound of formula (Ic):

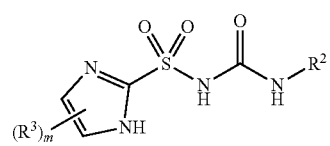

Formula (Ic)

wherein:
$R^2$ is as described herein;
$R^3$ is any optional monovalent substituent as described herein; and
m is 0, 1, 2 or 3.

Typically, the imidazolyl group of $R^1$ is substituted with one or more monovalent substituents. More typically, the imidazolyl group of $R^1$ is substituted with one or two monovalent substituents. For example, where the compound is a compound of formula (Ia), (Ib) or (Ic), m is typically 1 or 2.

Where the imidazolyl group of $R^1$ is substituted, typically it is substituted at least at the 1-position. For example, where the compound is a compound of formula (Ia), (Ib) or (Ic), typically the NH of the imidazolyl ring is N—$R^3$.

In one embodiment, the imidazolyl group of $R^1$ is substituted with one (i.e. a single) monovalent substituent. Where the imidazolyl group of $R^1$ is substituted with one monovalent substituent, $R^1$ may be for example a 1-substituted-imidazol-4-yl group, a 1-substituted-imidazol-5-yl group or a 1-substituted-imidazol-2-yl group. Most typically, $R^1$ is a 1-substituted-imidazol-4-yl group.

In another embodiment, the imidazolyl group of $R^1$ is substituted with two or three monovalent substituents. Typically in such an embodiment, the imidazolyl group of $R^1$ is substituted with two monovalent substituents. Where the imidazolyl group of $R^1$ is substituted with two monovalent substituents, $R^1$ may be for example a 1,2-disubstituted-imidazol-4-yl group, a 1,5-disubstituted-imidazol-4-yl group, a 1,2-disubstituted-imidazol-5-yl group, a 1,4-disubstituted-imidazol-5-yl group, a 1,4-disubstituted-imidazol-2-yl group or a 1,5-disubstituted-imidazol-2-yl group. More typically, $R^1$ is a 1,2-disubstituted-imidazol-4-yl group, a 1,5-disubstituted-imidazol-4-yl group or a 1,2-disubstituted-imidazol-5-yl group. Most typically, $R^1$ is a 1,2-disubstituted-imidazol-4-yl group.

In the above embodiments, where the imidazolyl group of $R^1$ is substituted with one or more monovalent substituents, the one or more monovalent substituents (e.g. $R^3$) may be independently selected from halo; —CN; —NO$_2$; —N$_3$; —$R^{(i)}$; —OH; —OR$^{(i)}$; —$R^\alpha$-halo; —$R^\alpha$—CN; —$R^\alpha$—NO$_2$; —$R^\alpha$—N$_3$; —$R^\alpha$—$R^\beta$; —$R^\alpha$—OH; —$R^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —$R^\alpha$—SH; —$R^\alpha$—SR$^\beta$; —$R^\alpha$—SOR$^\beta$; —$R^\alpha$—SO$_2$H; —$R^\alpha$—SO$_2$R$^\beta$; —$R^\alpha$—SO$_2$NH$_2$; —$R^\alpha$—SO$_2$NHR$^\beta$; —$R^\alpha$—SO$_2$N(R$^\beta$)$_2$; —Si(R$^\beta$)$_3$; —O—Si(R$^\beta$)$_3$; —$R^\alpha$—Si(R$^\beta$)$_3$; —$R^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —$R^\alpha$—NH$_2$; —$R^\alpha$—NHR$^\beta$; —$R^\alpha$—N(R$^\beta$)$_2$; —$R^\alpha$—N(O)(R$^\beta$)$_2$; —$R^\alpha$—N$^+$(R$^\beta$)$_3$; —CHO; —COR$^\beta$; —COOH; —COOR$^\beta$; —OCOR$^\beta$; —$R^\alpha$—CHO; —$R^\alpha$—COR$^\beta$; —$R^\alpha$—COOH; —$R^\alpha$—COOR$^\beta$; —$R^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —$R^\alpha$—C(=NH)R$^\beta$; —$R^\alpha$—C(=NH)NH$_2$; —$R^\alpha$—C(=NH)NHR$^\beta$; —$R^\alpha$—C(=NH)N(R$^\beta$)$_2$; —$R^\alpha$—C(=NR$^\beta$)R$^\beta$; —$R^\alpha$—C(=NR$^\beta$)NHR$^\beta$; —$R^\alpha$—C(=NR$^\beta$)N(R$^\beta$)$_2$; —$R^\alpha$—C(=NOH)R$^\beta$; —$R^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —$R^\alpha$—NH—CHO; —$R^\alpha$—NR$^\beta$—CHO; —$R^\alpha$—NH—COR$^\beta$; —$R^\alpha$—NR$^\beta$—COR$^\beta$; —$R^\alpha$—CONH$_2$; —$R^\alpha$—CONHR$^\beta$; —$R^\alpha$—CON(R$^\beta$)$_2$; —O—$R^\alpha$—OH; —O—$R^\alpha$—OR$^\beta$; —O—$R^\alpha$—NH$_2$; —O—$R^\alpha$—NHR$^\beta$; —O—$R^\alpha$—N(R$^\beta$)$_2$; —O—$R^\alpha$—N(O)(R$^\beta$)$_2$; —O—$R^\alpha$—N$^+$(R$^\beta$)$_3$; —NH—$R^\alpha$—OH; —NH—$R^\alpha$—OR$^\beta$; —NH—$R^\alpha$—NH$_2$; —NH—$R^\alpha$—NHR$^\beta$;

—NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —OCH, oxo (=O), or 4- to 6-membered heterocyclic group.

In one embodiment, where the imidazolyl group of R$^1$ is substituted with one or more monovalent substituents, the one or more monovalent substituents (e.g. R$^3$) may be independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_4$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

In one embodiment, the imidazolyl group of R$^1$ is substituted with one, two or three substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —OCH, oxo (=O), or 4- to 6-membered heterocyclic group.

Alternatively, R$^1$ may be substituted with one or more substituents independently selected from halo; —CN; —R$^\beta$; —OH; —OR$^\beta$; —R$^\alpha$-halo; —R$^\alpha$—CN; —R$^\alpha$—R$^\beta$; —R$^\alpha$—OH; —R$^\alpha$—OR$^\beta$; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more $C_4$-$C_4$ alkyl, halo, —OH, or 4- to 6-membered heterocyclic group.

In one embodiment, each monovalent substituent (e.g. $R^3$) of the imidazolyl group of $R^1$ is independently selected from a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton. Where the hydrocarbyl group is optionally substituted, typically it is substituted with one or more groups selected from halo, —CN, —OH, —$NH_2$, oxo (=O) and =NH.

Typically, each monovalent substituent (e.g. $R^3$) of the imidazolyl group of $R^1$ is independently selected from a saturated hydrocarbyl group, wherein the saturated hydrocarbyl group may be straight-chained or branched, or be or include cyclic groups, wherein the saturated hydrocarbyl group may optionally be substituted with one or more groups selected from halo, —CN, —OH, —$NH_2$ and oxo (=O), and wherein the saturated hydrocarbyl group may optionally include one or two heteroatoms N or O in its carbon skeleton.

More typically, each monovalent substituent (e.g. $R^3$) of the imidazolyl group of $R^1$ is independently selected from a saturated hydrocarbyl group, wherein the saturated hydrocarbyl group may be straight-chained or branched, or be or include cyclic groups, wherein the saturated hydrocarbyl group may optionally be substituted with one or more fluoro and/or chloro groups, and wherein the saturated hydrocarbyl group may optionally include a single heteroatom N or O in its carbon skeleton.

In one embodiment, each monovalent substituent (e.g. $R^3$) of the imidazolyl group of $R^1$ is acyclic. For example, each monovalent substituent (e.g. $R^3$) of the imidazolyl group of $R^1$ may be independently selected from a saturated hydrocarbyl group, wherein the saturated hydrocarbyl group is straight-chained or branched, wherein the saturated hydrocarbyl group may optionally be substituted with one or more groups selected from halo, —CN, —OH, —$NH_2$ and oxo (=O), and wherein the saturated hydrocarbyl group may optionally include one or two heteroatoms N or O in its carbon skeleton. More typically in such an embodiment, each monovalent substituent (e.g. $R^3$) of the imidazolyl group of $R^1$ is independently selected from a saturated hydrocarbyl group, wherein the saturated hydrocarbyl group is straight-chained or branched, wherein the saturated hydrocarbyl group may optionally be substituted with one or more fluoro and/or chloro groups, and wherein the saturated hydrocarbyl group may optionally include a single heteroatom N or O in its carbon skeleton.

In one aspect of any of the above embodiments, each monovalent substituent (e.g. each $R^3$) of the imidazolyl group of $R^1$ contains from 1 to 12 atoms other than hydrogen or halogen. More typically, each monovalent substituent of the imidazolyl group contains from 1 to 8 atoms other than hydrogen or halogen. Most typically, each monovalent substituent of the imidazolyl group contains from 1 to 6 atoms other than hydrogen or halogen.

In one embodiment, each monovalent substituent (e.g. $R^3$) of the imidazolyl group of $R^1$ is independently selected from the group consisting of: methyl, ethyl, isopropyl,

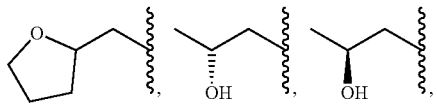

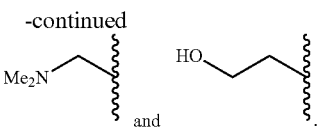

In one aspect of any of the above embodiments, $R^1$ contains from 5 to 30 atoms other than hydrogen. More typically, $R^1$ contains from 6 to 25 atoms other than hydrogen. More typically, $R^1$ contains from 6 to 20 atoms other than hydrogen. More typically, $R^1$ contains from 6 to 17 atoms other than hydrogen.

In one aspect of any of the above embodiments, $R^1$ contains from 5 to 25 atoms other than hydrogen or halogen. More typically, $R^1$ contains from 6 to 20 atoms other than hydrogen or halogen. More typically still, $R^1$ contains from 6 to 15 atoms other than hydrogen or halogen. Most typically, $R^1$ contains from 6 to 12 atoms other than hydrogen or halogen.

$R^2$ is a cyclic group substituted at the α-position, wherein $R^2$ may optionally be further substituted. For the avoidance of doubt, it is noted that it is a ring atom of the cyclic group of $R^2$ that is directly attached to the nitrogen atom of the urea or thiourea group, not any substituent.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is a phenyl or a 5- or 6-membered heteroaryl group, wherein the phenyl or the heteroaryl group is substituted at the α-position, and wherein $R^2$ may optionally be further substituted. Typically, $R^2$ is an aryl or a heteroaryl group, wherein the aryl or the heteroaryl group is substituted at the α and α' positions, and wherein $R^2$ may optionally be further substituted. Typically, $R^2$ is a phenyl or a 5- or 6-membered heteroaryl group, wherein the phenyl or the heteroaryl group is substituted at the α and α' positions, and wherein $R^2$ may optionally be further substituted. For example, $R^2$ may be a phenyl group substituted at the 2- and 6-positions or a phenyl group substituted at the 2-, 4- and 6-positions.

In one embodiment, the parent phenyl or 5- or 6-membered heteroaryl group of $R^2$ may be selected from phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl. Typically, the parent phenyl or 5- or 6-membered heteroaryl group of $R^2$ may be selected from phenyl, pyridinyl, pyridazinyl, pyrimidinyl, pyrrolyl, pyrazolyl, imidazolyl or triazolyl. Typically, the parent phenyl or 5- or 6-membered heteroaryl group of $R^2$ may be selected from phenyl, pyridinyl, pyridazinyl, pyrimidinyl or pyrazolyl.

As used herein, the nomenclature α, β, α', β' refers to the position of the atoms of a cyclic group, such as —$R^2$, relative to the point of attachment of the cyclic group to the remainder of the molecule. For example, where —$R^2$ is a 1,2,3,5,6,7-hexahydro-s-indacen-4-yl moiety, the α,β, α' and β' positions are as follows:

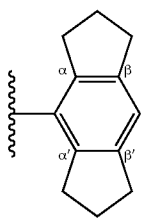 [SMILES: *c1c2c(cc3c1CCC3)CCC2]

For the avoidance of doubt, where it is stated that a cyclic group, such as an aryl or a heteroaryl group, is substituted at the α and/or α' positions, it is to be understood that one or more hydrogen atoms at the α and/or α' positions respectively are replaced by one or more substituents, such as any optional substituent as defined above. Unless stated otherwise, the term "substituted" does not include the replacement of one or more ring carbon atoms by one or more ring heteroatoms.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions may be independently selected from —$R^4$, —$OR^4$ and —$COR^4$ groups, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the aryl or heteroaryl group across the α,β positions. Typically, the aryl or heteroaryl group is also substituted at the α' position, for example with a substituent selected from —$R^4$, —$OR^4$ and —$COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

More typically, $R^2$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure. Typically, the phenyl or the 5- or 6-membered heteroaryl group is also substituted at the α' position, for example with a substituent selected from —$R^4$, —$OR^4$ and —$COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted. Typically in such an embodiment, $R^2$ is tricyclic.

More typically, $R^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α',β' positions so as to form a second 4- to 6-membered fused ring structure, wherein $R^2$ may optionally be further substituted. Typically in such an embodiment, $R^2$ is tricyclic.

In one embodiment, —$R^2$ has a formula selected from:

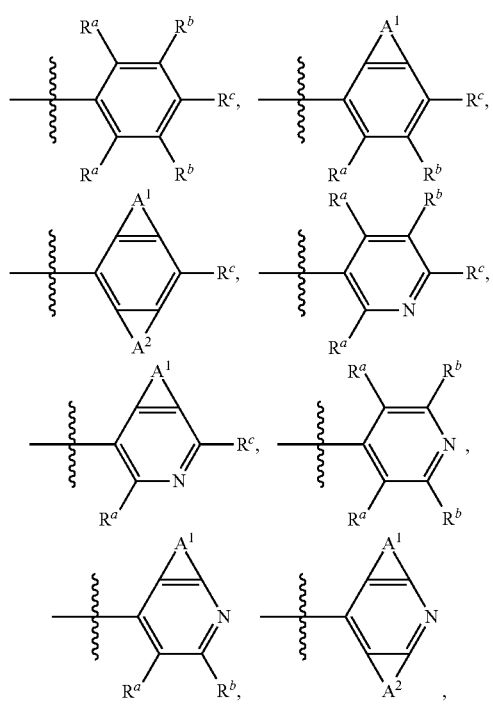

-continued

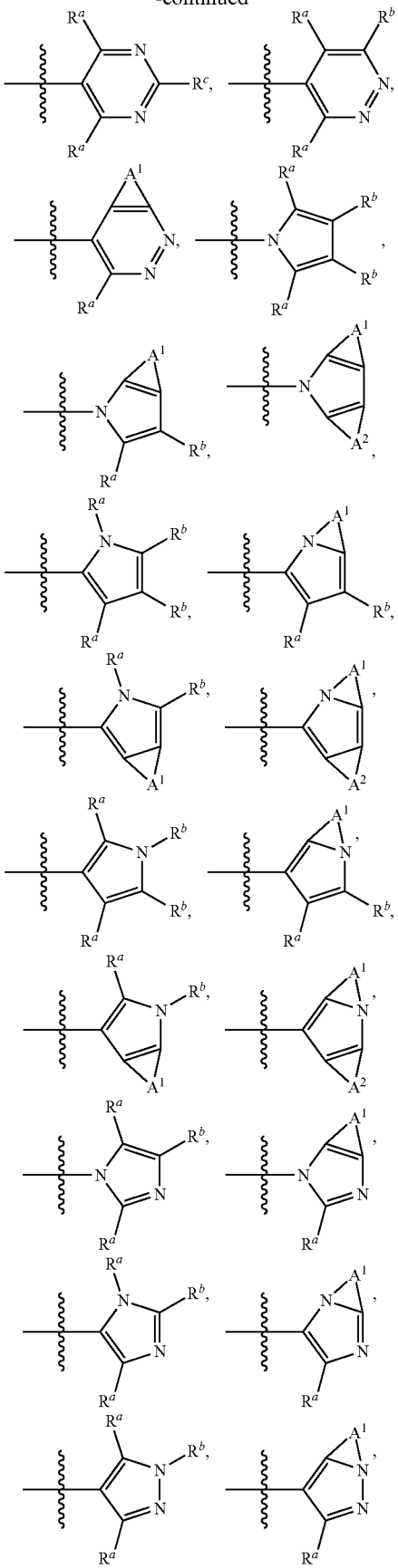

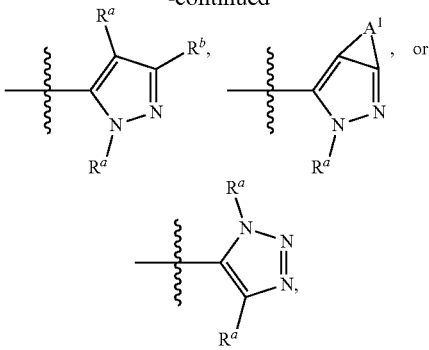

wherein:
A¹ and A² are each independently selected from an optionally substituted alkylene or alkenylene group, wherein one or more carbon atoms in the backbone of the alkylene or alkenylene group may optionally be replaced by one or more heteroatoms N, O or S;

each $R^a$ is independently selected from —$R^{aa}$, —$OR^{aa}$ or —$COR^{aa}$;

each $R^b$ is independently selected from hydrogen, halo, —$NO_2$, —CN, —$R^{aa}$, —$OR^{aa}$ or —$COR^{aa}$;

provided that any $R^a$ or $R^b$ that is directly attached to a ring nitrogen atom is not halo, —$NO_2$, —CN, or —$OR^{aa}$;

each $R^c$ is independently selected from hydrogen, halo, —OH, —$NO_2$, —CN, —$R^{cc}$, —$OR^{cc}$, —$COR^{cc}$, —$COOR^{cc}$, —$CONH_2$, —$CONHR^{cc}$ or —$CON(R^{cc})_2$;

each $R^{aa}$ is independently selected from a $C_1$-$C_6$ alkyl, $C_2$-$C_6$ alkenyl, $C_2$-$C_6$ alkynyl or a 3- to 7-membered cyclic group, wherein each $R^{aa}$ is optionally substituted; and each $R^{cc}$ is independently selected from a $C_1$-$C_6$ alkyl, $C_2$-$C_6$ alkenyl, $C_2$-$C_6$ alkynyl or a 3- to 7-membered cyclic group, or any two $R^{cc}$ attached to the same nitrogen atom may, together with the nitrogen atom to which they are attached, form a 3- to 7-membered heterocyclic group, wherein each $R^{cc}$ is optionally substituted.

Typically, any ring containing A¹ or A² is a 5- or 6-membered ring. Typically, A¹ and A² are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A¹ and A² are each independently selected from an optionally substituted straight-chained alkylene group, wherein one carbon atom in the backbone of the alkylene group may optionally be replaced by an oxygen atom. Typically, no heteroatom in A¹ or A² is directly attached to another ring heteroatom. Typically, A¹ and A² are unsubstituted or substituted with one or more substituents independently selected from halo, —OH, —CN, —$NO_2$, $C_1$-$C_4$ alkyl, $C_1$-$C_4$ haloalkyl, —O($C_1$-$C_4$ alkyl) or —O($C_1$-$C_4$ haloalkyl). More typically, A¹ and A² are unsubstituted or substituted with one or more fluoro and/or chloro groups. Where $R^2$ contains both A¹ and A² groups, A¹ and A² may be the same or different. Typically, A¹ and A² are the same.

Where $R^{aa}$ is a substituted $C_1$-$C_6$ alkyl, $C_2$-$C_6$ alkenyl or $C_2$-$C_6$ alkynyl group, typically the $C_1$-$C_6$ alkyl, $C_2$-$C_6$ alkenyl or $C_2$-$C_6$ alkynyl group is substituted with one or more (e.g. one or two) substituents independently selected from halo, —OH, —CN, —NO$_2$, —O(C$_1$-C$_4$ alkyl) or —O(C$_1$-C$_4$ haloalkyl).

Where R$^{aa}$ is a substituted 3- to 7-membered cyclic group, typically the 3- to 7-membered cyclic group is substituted with one or more (e.g. one or two) substituents independently selected from halo, —OH, —NH$_2$, —CN, —NO$_2$, —B$^1$, —OB$^1$, —NHB$^1$, —N(B$^1$)$_2$, —CONH$_2$, —CONHB$^1$, —CON(B$^1$)$_2$, —NHCOB$^1$, —NB$^1$COB$^1$, or —B$^{11}$—;

- wherein each B$^1$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B$^1$ may optionally be halo-substituted and/or substituted with one or two substituents independently selected from —OH, —NH$_2$, —OB$^{12}$, —NHB$^{12}$ or —N(B$^{12}$)$_2$;
- wherein each B$^{11}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and
- wherein each B$^{12}$ is independently selected from a C$_1$-C$_3$ alkyl or C$_4$-C$_3$ haloalkyl group. Typically, any divalent group —B$^{11}$— forms a 4- to 6-membered fused ring.

Typically, each R$^a$ is —R$^{aa}$. More typically, each R$^a$ is independently selected from a C$_1$-C$_6$ alkyl (in particular C$_3$-C$_6$ branched alkyl) or C$_3$-C$_6$ cycloalkyl group, wherein each R$^a$ is optionally further substituted with one or more halo groups. More typically, each R$^a$ is independently selected from a C$_1$-C$_4$ alkyl, C$_1$-C$_4$ haloalkyl, C$_3$-C$_4$ cycloalkyl or C$_3$-C$_4$ halocycloalkyl group. Where a group R$^a$ is present at both the α- and α'-positions, each R$^a$ may be the same or different. Typically, each R$^a$ is the same.

Typically, each R$^b$ is independently selected from hydrogen or halo. More typically, each R$^b$ is hydrogen.

Typically, each R$^c$ is independently selected from hydrogen, halo, —OH, —NO$_2$, —CN, —R$^{cc}$ or —OR$^{cc}$. More typically, each R$^c$ is independently selected from hydrogen, halo, —CN, C$_1$-C$_3$ alkyl, C$_1$-C$_3$ haloalkyl, cyclopropyl or halocyclopropyl. Most typically, each R$^c$ is independently selected from hydrogen or halo.

Typically, each R$^{cc}$ is independently selected from a C$_1$-C$_4$ alkyl or C$_3$-C$_6$ cycloalkyl group, or any two R$^{cc}$ attached to the same nitrogen atom may, together with the nitrogen atom to which they are attached, form a 3- to 6-membered saturated heterocyclic group, wherein each R$^{cc}$ is optionally substituted. Where R$^{cc}$ is substituted, typically R$^{cc}$ is substituted with one or more halo, —OH, —CN, —NO$_2$, —O(C$_1$-C$_4$ alkyl) or —O(C$_1$-C$_4$ haloalkyl) groups. More typically, each R$^{cc}$ is independently selected from a C$_1$-C$_4$ alkyl, C$_1$-C$_4$ haloalkyl, C$_3$-C$_4$ cycloalkyl or C$_3$-C$_4$ halocycloalkyl group.

In one embodiment, —R$^2$ has a formula selected from:

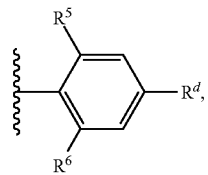

wherein R$^5$ and R$^6$ are independently selected from C$_1$-C$_4$ alkyl, C$_1$-C$_4$ haloalkyl, C$_3$-C$_4$ cycloalkyl and C$_3$-C$_4$ halocycloalkyl, and R$^d$ is hydrogen, halo, —OH, —NO$_2$, —CN, —R$^{dd}$, —OR$^{dd}$, —COR$^{dd}$, —COOR$^{dd}$, —CONH$_2$, —CONHR$^{dd}$ or —CON(R$^{dd}$)$_2$, wherein each —R$^{dd}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^5$ and R$^6$ are independently selected from C$_1$-C$_4$ alkyl, and R$^d$ is hydrogen, halo, —CN, C$_1$-C$_3$ alkyl, C$_1$-C$_3$ haloalkyl, cyclopropyl or halocyclopropyl. More typically, R$^5$ and R$^6$ are independently selected from C$_1$-C$_4$ alkyl, and R$^d$ is hydrogen or halo. In one aspect of such an embodiment, R$^5$ and R$^6$ are independently selected from C$_1$-C$_4$ alkyl, and R$^d$ is halo.

Typically, —R$^2$ has a formula selected from:

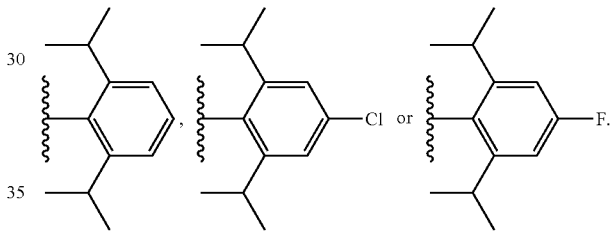

In one embodiment, —R$^2$ has a formula selected from:

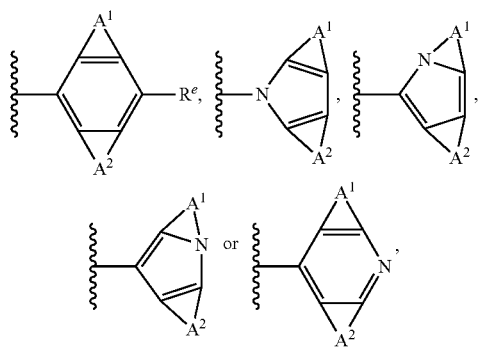

wherein A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S, and wherein R$^e$ is hydrogen or any optional substituent. R$^e$ and any optional substituent attached to A$^1$ or A$^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to A$^1$ and any optional substituent attached to A$^2$ may also together with the atoms to which they are attached form a further fused cycloalkyl, cycloalkenyl, non-aromatic heterocyclic, aryl or heteroaryl ring which may itself be optionally substituted.

In one embodiment, $R^e$ is hydrogen, halo, —OH, —NO$_2$, —CN, —R$^{ee}$, —OR$^{ee}$, —COR$^{ee}$, —COOR$^{ee}$, —CONH$_2$, —CONHR$^{ee}$ or —CON(R$^{ee}$)$_2$, wherein each —R$^{ee}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, $R^e$ is hydrogen or a halo, hydroxyl, —CN, —NO$_2$, —R$^{ee}$ or —OR$^{ee}$ group, wherein R$^{ee}$ is a C$_1$-C$_4$ alkyl group which may optionally be halo-substituted. More typically, $R^e$ is hydrogen or a halo, hydroxyl, —CN, —R$^{ee}$ or —OR$^{ee}$ group, wherein R$^{ee}$ is a C$_1$-C$_4$ alkyl group which may optionally be halo-substituted. More typically, $R^e$ is hydrogen or halo.

Typically, any ring containing A$^1$ or A$^2$ is a 5- or 6-membered ring.

Typically, A$^1$ and A$^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A$^1$ and A$^2$ are each independently selected from an optionally substituted straight-chained alkylene group, wherein one carbon atom in the backbone of the alkylene group may optionally be replaced by an oxygen atom. Typically, no heteroatom in A$^1$ or A$^2$ is directly attached to another ring heteroatom. Typically, A$^1$ and A$^2$ are unsubstituted or substituted with one or more halo, hydroxyl, —CN, —NO$_2$, —B$^3$ or —OB$^3$ groups, wherein B$^3$ is a C$_1$-C$_4$ alkyl group which may optionally be halo-substituted. More typically, A$^1$ and A$^2$ are unsubstituted or substituted with one or more halo, hydroxyl, —CN, —B$^3$ or —OB$^3$ groups, wherein B$^3$ is a C$_1$-C$_4$ alkyl group which may optionally be halo-substituted. More typically, A$^1$ and A$^2$ are unsubstituted or substituted with one or more fluoro and/or chloro groups. Where R$^2$ contains both A$^1$ and A$^2$ groups, A$^1$ and A$^2$ may be the same or different. Typically, A$^1$ and A$^2$ are the same.

In a further embodiment, —R$^2$ has a formula selected from:

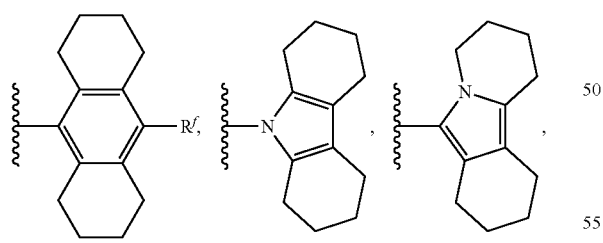

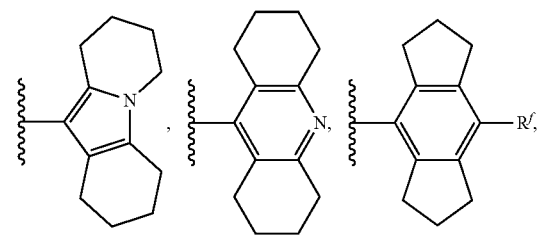

-continued

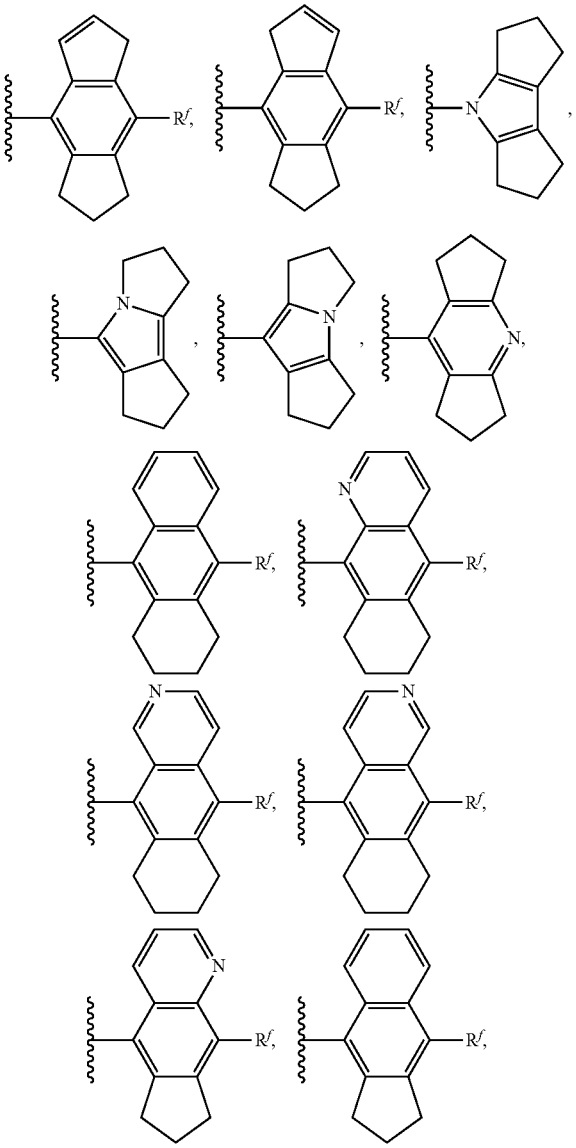

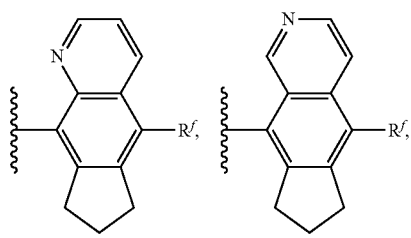

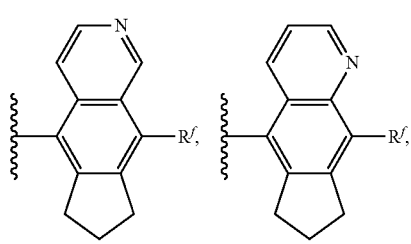

-continued

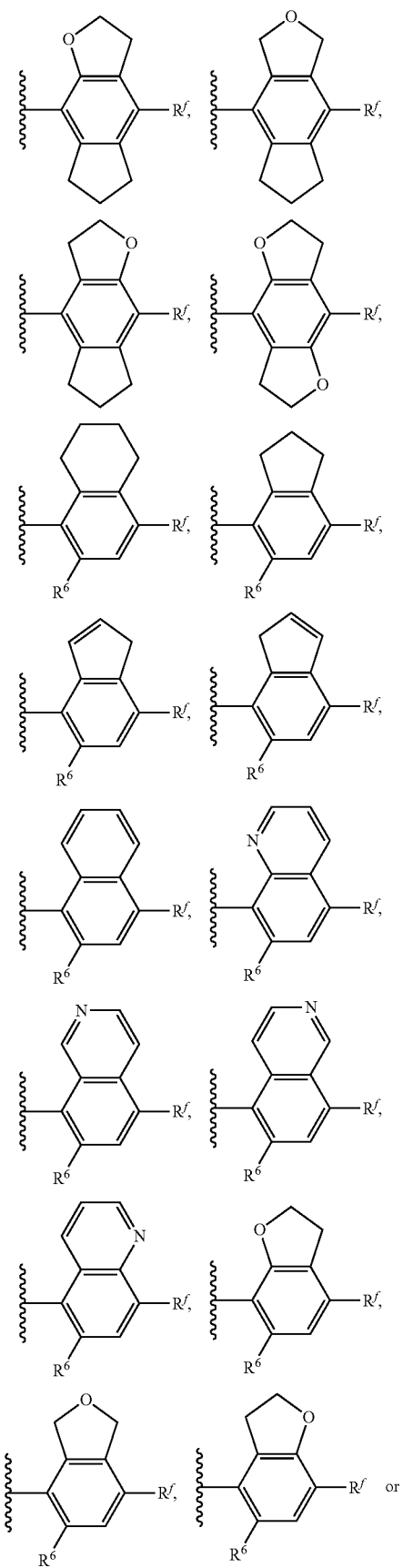

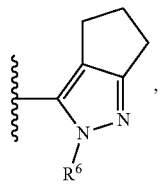

wherein $R^6$ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —NO$_2$, —CN, —$R^{ff}$, —O$R^{ff}$, —CO$R^{ff}$, —COO$R^{ff}$, —CONH$_2$, —CONHR$^{ff}$ or —CON(R$^{ff}$)$_2$, wherein each —$R^{ff}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^6$ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, $R^6$ is $C_1$-$C_4$ alkyl, and $R^f$ is hydrogen or halo.

Typically, —$R^2$ has the formula:

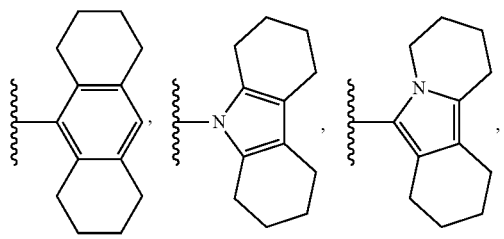

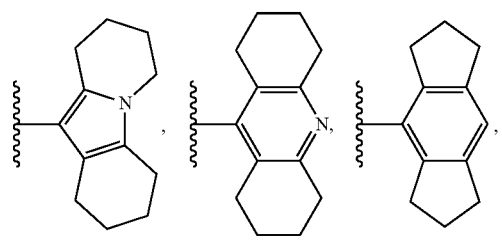

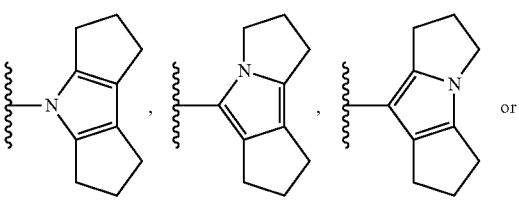

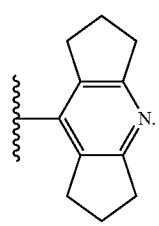

More typically, —R² has the formula:

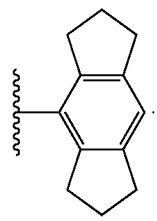 [SMILES: *c1c2c(cc3c1CCC3)CCC2 ; "."]

Yet other typical substituents at the α-position of the parent cyclic group of R² may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such R² groups are described in greater detail below.

In one embodiment, the α-substituted parent cyclic group of R² is a 5- or 6-membered cyclic group, wherein the cyclic group may optionally be further substituted. In one embodiment, the α-substituted parent cyclic group of R² is an aryl or a heteroaryl group, all of which may optionally be further substituted. In one embodiment, the α-substituted parent cyclic group of R² is a phenyl or a 5- or 6-membered heteroaryl group, all of which may optionally be further substituted. In one embodiment, the ci-substituted parent cyclic group of R² is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of R² is a phenyl or pyrazolyl group, both of which may optionally be further substituted. In a further embodiment, the α-substituted parent cyclic group of R² is a phenyl group, which may optionally be further substituted.

In one embodiment, the α-substituted parent cyclic group of R² is substituted at the α and α' positions, and may optionally be further substituted. For example, the α-substituted parent cyclic group of R² may be a phenyl group substituted at the 2- and 6-positions or a phenyl group substituted at the 2-, 4- and 6-positions.

In one embodiment, R² is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH₂, —CN, —NO₂, —B⁴, —OB⁴, —NHB⁴, —N(B⁴)₂, —CONH₂, —CONHB⁴, —CON(B⁴)₂, —NHCOB⁴, —NB⁴COB⁴, or —B⁴⁴—;

wherein each B⁴ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁴ together with the nitrogen atom to which they are attached may form a 4- to 6-membered heterocyclic group containing one or two ring heteroatoms N and/or O, wherein any B⁴ may optionally be halo-substituted and/or substituted with one or two substituents independently selected from —OH, —NH₂, —OB⁴⁵, —NHB⁴⁵ or —N(B⁴⁵)₂;

wherein each B⁴⁴ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁴⁵, —NHB⁴⁵ or —N(B⁴⁵)₂; and wherein each B⁴⁵ is independently selected from a $C_1$-$C_3$ alkyl or $C_1$-$C_3$ haloalkyl group.

Typically, any divalent group —B⁴⁴— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of R$^2$. Such further substituents may be independently selected from halo, —R$^8$, —OR$^8$ or —COR$^8$ groups, wherein each R$^8$ is independently selected from a C$_1$-C$_6$ alkyl, C$_2$-C$_6$ alkenyl, C$_2$-C$_6$ alkynyl or C$_2$-C$_6$ cyclic group and wherein each R$^8$ is optionally further substituted with one or more halo groups. Typically, such further substituents on the α-substituted parent cyclic group of R$^2$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

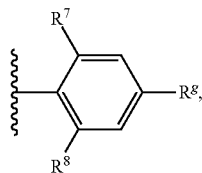

wherein R$^7$ is C$_1$-C$_4$ alkyl, C$_1$-C$_4$ haloalkyl, C$_3$-C$_6$ cycloalkyl or C$_3$-C$_6$ halocycloalkyl, R$^8$ is a 5- or 6-membered, optionally substituted heterocyclic or aromatic group, and R$^g$ is hydrogen, halo, —OH, —NO$_2$, —CN, —R$^{gg}$, —OR$^{gg}$, —COR$^{gg}$, —COOR$^{gg}$, —CONH$_2$, —CONHR$^{gg}$ or —CON(R$^{gg}$)$_2$, wherein each —R$^{gg}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B$^5$, —OB$^5$, —NHB$^5$, —N(B$^5$)$_2$, —CONH$_2$, —CONHB$^5$, —CON(B$^5$)$_2$, —NHCOB$^5$, —NB$^5$COB$^5$, or —B$^{55}$—;

wherein each B$^5$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^5$ together with the nitrogen atom to which they are attached may form a 4- to 6-membered heterocyclic group containing one or two ring heteroatoms N and/or O, wherein any B$^5$ may optionally be halo-substituted and/or substituted with one or two substituents independently selected from —OH, —NH$_2$, —OB$^{56}$, —NHB$^{56}$ or —N(B$^{56}$)$_2$;

wherein each B$^{55}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{56}$, —NHB$^{56}$ or —N(B$^{56}$)$_2$; and wherein each B$^{56}$ is independently selected from a C$_1$-C$_3$ alkyl or C$_1$-C$_3$ haloalkyl group.

Typically, any divalent group —B$^{55}$— forms a 4- to 6-membered fused ring. Typically, R$^7$ is C$_1$-C$_4$ alkyl, R$^8$ is a 5- or 6-membered, optionally substituted heterocyclic or aromatic group, and R$^g$ is hydrogen, halo, —CN, C$_1$-C$_3$ alkyl, C$_1$-C$_3$ haloalkyl, cyclopropyl or halocyclopropyl. More typically, R$^7$ is C$_1$-C$_4$ alkyl, R$^8$ is a 5- or 6-membered, optionally substituted heterocyclic or aromatic group, and R$^g$ is hydrogen or halo. In one embodiment, the optional substituents on the heterocyclic or aromatic group are independently selected from halo, —OH, —NH$_2$, —CN, —B$^5$, —OB$^5$, —NHB$^5$ or —N(B$^5$)$_2$, wherein each B$^5$ is independently selected from a C$_1$-C$_4$ alkyl, C$_2$-C$_4$ alkenyl or C$_2$-C$_4$ alkynyl group all of which may optionally be halo-substituted.

Typically, —R$^2$ has a formula selected from:

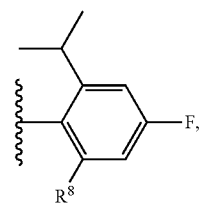

wherein R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^6$, —OB$^6$, —NHB$^6$, —N(B$^6$)$_2$, —CONH$_2$, —CONHB$^6$, —CON(B$^6$)$_2$, —NHCOB$^6$, —NB$^6$COB$^6$, or —B$^{66}$—;

wherein each B$^6$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^6$ together with the nitrogen atom to which they are attached may form a 4- to 6-membered heterocyclic group containing one or two ring heteroatoms N and/or O, wherein any B$^6$ may optionally be halo-substituted and/or substituted with one or two substituents independently selected from —OH, —NH$_2$, —OB$^{67}$, —NHB$^{67}$ or —N(B$^{67}$)$_2$;

wherein each $B^{66}$ is independently selected from a $C_1$-$C_8$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{67}$, —NHB$^{67}$ or —N(B$^{67}$)$_2$; and wherein each $B^{67}$ is independently selected from a $C_1$-$C_3$ alkyl or $C_1$-$C_3$ haloalkyl group.

Typically, any divalent group —B$^{66}$— forms a 4- to 6-membered fused ring. Typically, the optional substituents on the heterocyclic or aromatic group are independently selected from halo, —OH, —NH$_2$, —CN, —B$^6$, —OB$^6$, —NHB$^6$ or —N(B$^6$)$_2$, wherein each $B^6$ is independently selected from a $C_1$-$C_4$ alkyl, $C_2$-$C_4$ alkenyl or $C_2$-$C_4$ alkynyl group all of which may optionally be halo-substituted.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the ci-substituted parent cyclic group of $R^2$ also include cycloalkyl, cycloalkenyl, non-aromatic heterocyclic, aryl or heteroaryl rings which are fused to the α-substituted parent cyclic group of $R^2$. Typically, the cycloalkyl, cycloalkenyl, non-aromatic heterocyclic, aryl or heteroaryl rings are ortho-fused to the α-substituted parent cyclic group of $R^2$, i.e. each fused cycloalkyl, cycloalkenyl, non-aromatic heterocyclic, aryl or heteroaryl ring has only two atoms and one bond in common with the α-substituted parent cyclic group of $R^2$. Typically, the cycloalkyl, cycloalkenyl, non-aromatic heterocyclic, aryl or heteroaryl rings are ortho-fused to the α-substituted parent cyclic group of $R^2$ across the α',β' positions.

In one embodiment, —$R^2$ has a formula selected from:

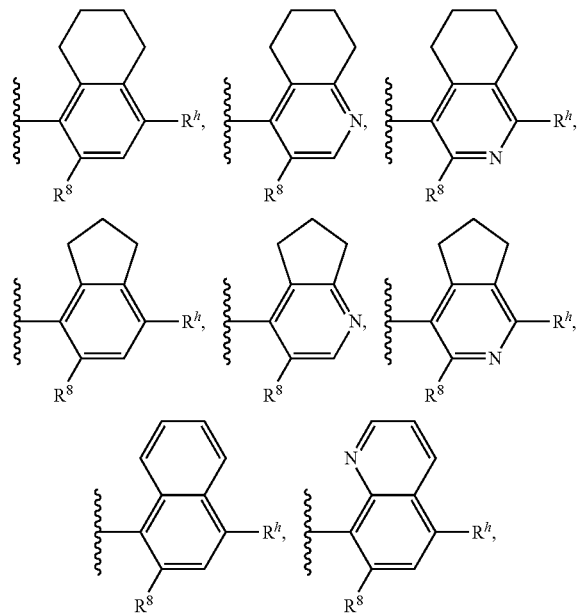

-continued

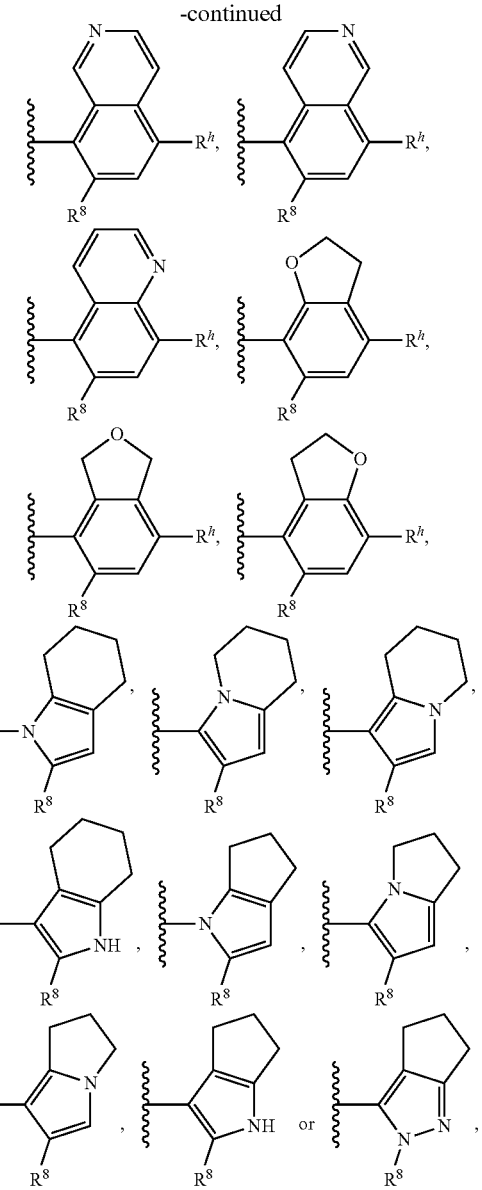

wherein $R^8$ is a 5- or 6-membered, optionally substituted heterocyclic or aromatic group, and $R^h$ is hydrogen, halo, —OH, —NO$_2$, —CN, —R$^{hh}$, —OR$^{hh}$, —COR$^{hh}$, —CO-OR$^{hh}$, —CONH$_2$, —CONHR$^{hh}$ or —CON(R$^{hh}$)$_2$, wherein each —R$^{hh}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH$_2$, —CN, —NO$_2$, —B$^7$, —OB$^7$, —NHB$^7$, —N(B$^7$)$_2$, —CONH$_2$, —CONHB$^7$, —CON(B$^7$)$_2$, —NHCOB$^7$, —NB$^7$COB$^7$, or —B$^{77}$—;

wherein each $B^7$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^7$ together with the nitrogen atom to which they are attached may form a 4- to 6-membered heterocyclic group containing one or two ring heteroatoms N and/or O, wherein any $B^7$ may optionally be halo-substituted and/or substituted with one or two substituents independently selected from —OH, —NH₂, —OB⁷⁸, —NHB⁷⁸ or —N(B⁷⁸)₂;

wherein each B⁷⁷ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁷⁸, —NHB⁷⁸ or —N(B⁷⁸)₂; and wherein each B⁷⁸ is independently selected from a $C_4$-$C_3$ alkyl or $C_4$-$C_3$ haloalkyl group.

Typically, any divalent group —B⁷⁷— forms a 4- to 6-membered fused ring. Typically, $R^h$ is hydrogen, halo, —CN, $C_1$-$C_3$ alkyl, $C_1$-$C_3$ haloalkyl, cyclopropyl or halocyclopropyl. More typically, $R^h$ is hydrogen or halo. Typically, the optional substituents on the heterocyclic or aromatic group are independently selected from halo, —OH, —NH₂, —CN, —B⁷, —OB⁷, —NHB⁷ or —N(B⁷)₂, wherein each B⁷ is independently selected from a $C_1$-$C_4$ alkyl, $C_2$-$C_4$ alkenyl or $C_2$-$C_4$ alkynyl group all of which may optionally be halo-substituted.

In one embodiment, —R² has a formula selected from:

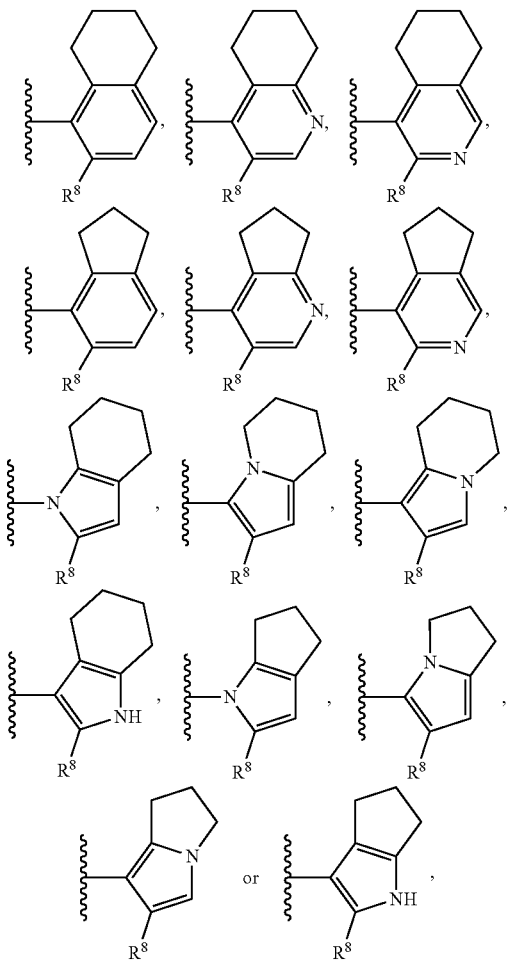

wherein R⁸ is a 5- or 6-membered, optionally substituted heterocyclic or aromatic group. In one embodiment, the optional substituents on the heterocyclic or aromatic group are independently selected from halo, —OH, —NH₂, —CN, —NO₂, —B⁸, —OB⁸, —NHB⁸, —N(B⁸)₂, —CONH₂, —CONHB⁸, —CON(B⁸)₂, —NHCOB⁸, —NB⁸COB⁸, or —B⁸⁸—;

wherein each B⁸ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁸ together with the nitrogen atom to which they are attached may form a 4- to 6-membered heterocyclic group containing one or two ring heteroatoms N and/or O, wherein any B⁸ may optionally be halo-substituted and/or substituted with one or two substituents independently selected from —OH, —NH₂, —OB⁸⁹, —NHB⁸⁹ or —N(B⁸⁹)₂;

wherein each B⁸⁸ is independently selected from a $C_1$-$C_8$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁸⁹, —NHB⁸⁹ or —N(B⁸⁹)₂; and wherein each B⁸⁹ is independently selected from a $C_1$-$C_3$ alkyl or $C_1$-$C_3$ haloalkyl group.

Typically, any divalent group —B⁸⁸— forms a 4- to 6-membered fused ring. Typically, the optional substituents on the heterocyclic or aromatic group are independently selected from halo, —OH, —NH₂, —CN, —B⁸, —OB⁸, —NHB⁸ or —N(B⁸)₂, wherein each B⁸ is independently selected from a $C_1$-$C_4$ alkyl, $C_2$-$C_4$ alkenyl or $C_2$-$C_4$ alkynyl group all of which may optionally be halo-substituted.

Typically, —R² has a formula selected from:

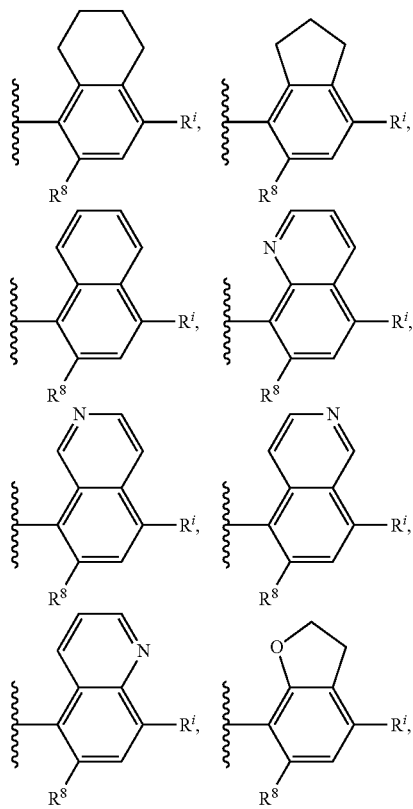

-continued

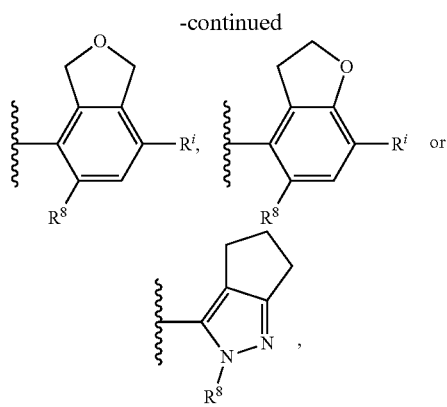

wherein $R^8$ is a 5- or 6-membered, optionally substituted heterocyclic or aromatic group, and $R^i$ is hydrogen, halo, —OH, —NO$_2$, —CN, —$R^{ii}$, —OR$^{ii}$, —COR$^{ii}$, —COOR$^{ii}$, —CONH$_2$, —CONHR$^{ii}$ or —CON(R$^{ii}$)$_2$, wherein each —R$^{ii}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH$_2$, —CN, —NO$_2$, —B$^9$, —OB$^9$, —NHB$^9$, —N(B$^9$)$_2$, —CONH$_2$, —CONHB$^9$, —CON(B$^9$)$_2$, —NHCOB$^9$, —NB$^9$COB$^9$, or —B$^{99}$—;
  wherein each B$^9$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^9$ together with the nitrogen atom to which they are attached may form a 4- to 6-membered heterocyclic group containing one or two ring heteroatoms N and/or O, wherein any Eh may optionally be halo-substituted and/or substituted with one or two substituents independently selected from —OH, —NH$_2$, —OB$^{98}$, —NHB$^{98}$ or —N(B$^{98}$)$_2$;
  wherein each B$^{99}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{98}$, —NHB$^{98}$ or —N(B$^{98}$)$_2$; and
  wherein each B$^{98}$ is independently selected from a $C_1$-$C_3$ alkyl or $C_1$-$C_3$ haloalkyl group.

Typically, any divalent group —B$^{99}$— forms a 4- to 6-membered fused ring. Typically, $R^i$ is hydrogen, halo, —CN, $C_1$-$C_3$ alkyl, $C_1$-$C_3$ haloalkyl, cyclopropyl or halocyclopropyl. More typically, $R^i$ is hydrogen or halo. Typically, the optional substituents on the heterocyclic or aromatic group are independently selected from halo, —OH, —NH$_2$, —CN, —B$^9$, —OB$^9$, —NHB$^9$ or —N(B$^9$)$_2$, wherein each B$^9$ is independently selected from a $C_1$-$C_4$ alkyl, $C_2$-$C_4$ alkenyl or $C_2$-$C_4$ alkynyl group all of which may optionally be halo-substituted.

In one embodiment, $R^2$ is phenyl or a 5- or 6-membered heteroaryl group (such as phenyl, pyridinyl, pyridazinyl, pyrimidinyl or pyrazinyl); wherein
  (i) the phenyl or 5- or 6-membered heteroaryl group is substituted at the α position with a substituent selected from —R$^4$, —OR$^4$ and —COR$^4$, wherein R$^4$ is selected from a $C_1$-$C_6$ alkyl, $C_2$-$C_6$ alkenyl, $C_2$-$C_6$ alkynyl or $C_2$-$C_6$ cyclic group and wherein R$^4$ is optionally substituted with one or more halo groups; and
  optionally the phenyl or 5- or 6-membered heteroaryl group is further substituted at the α' position with a substituent selected from —R$^{14}$, —OR$^{14}$ and —COR$^{14}$, wherein R$^{14}$ is selected from a $C_1$-$C_6$ alkyl, $C_2$-$C_6$ alkenyl, $C_2$-$C_6$ alkynyl or $C_2$-$C_6$ cyclic group and wherein R$^{14}$ is optionally substituted with one or more halo groups; and
  optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or
  (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α, β positions and which is optionally substituted with one or more halo groups; and
  optionally the phenyl or 5- or 6-membered heteroaryl group is further substituted at the α' position with a substituent selected from —R$^4$, —OR$^4$ and —COR$^4$, wherein R$^4$ is selected from a $C_1$-$C_6$ alkyl, $C_2$-$C_6$ alkenyl, $C_2$-$C_6$ alkynyl or $C_2$-$C_6$ cyclic group and wherein R$^4$ is optionally substituted with one or more halo groups; and
  optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or
  (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α, β positions and which is optionally substituted with one or more halo groups; and
  the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and
  optionally the phenyl group is further substituted (typically with a substituent selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or
  (iv) the phenyl or 5- or 6-membered heteroaryl group is substituted at the ex-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —R$^{12}$—OR$^{13}$, —R$^{12}$—N(R$^{13}$)$_2$, —R$^{12}$—CN or —R$^{12}$—C≡CR$^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (v) the phenyl or 5- or 6-membered heteroaryl group is substituted at the ex-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_4$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{13}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^2$ contains from 10 to 50 atoms other than hydrogen. More typically, $R^2$ contains from 10 to 40 atoms other than hydrogen. More typically, $R^2$ contains from 10 to 35 atoms other than hydrogen. Most typically, $R^2$ contains from 12 to 30 atoms other than hydrogen.

In one aspect of any of the above embodiments, $R^2$ contains from 5 to 30 atoms other than hydrogen or halogen. More typically, $R^2$ contains from 7 to 25 atoms other than hydrogen or halogen. More typically, $R^2$ contains from 9 to 20 atoms other than hydrogen or halogen. Most typically, $R^2$ contains from 12 to 18 atoms other than hydrogen or halogen.

Q is selected from O or S. In one embodiment of the first aspect of the invention, Q is O.

In one aspect of any of the above embodiments, the compound of formula (I) has a molecular weight of from 250 to 2000 Da. Typically, the compound of formula (I) has a molecular weight of from 300 to 900 Da. More typically, the compound of formula (I) has a molecular weight of from 330 to 550 Da.

A second aspect of the invention provides a compound selected from the group consisting of:

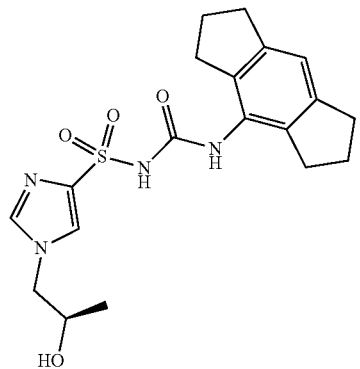

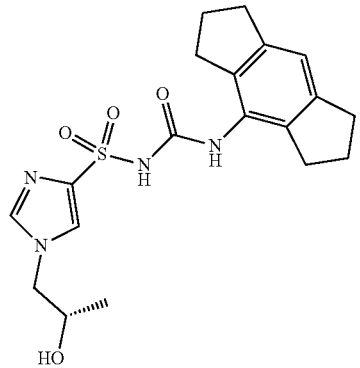

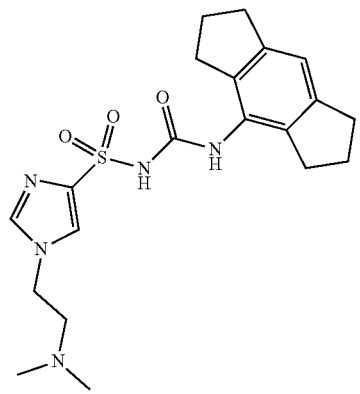

-continued
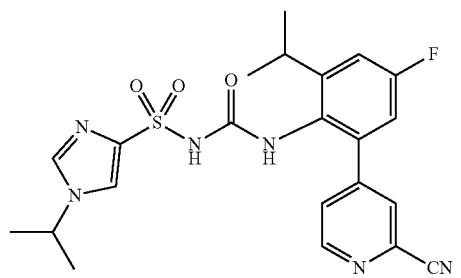
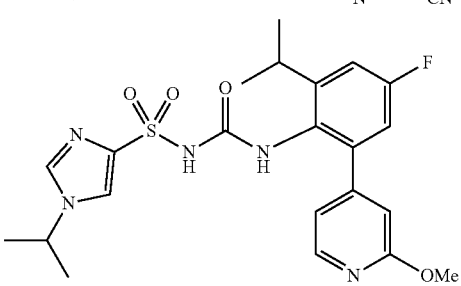
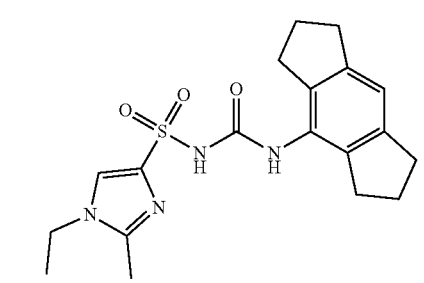
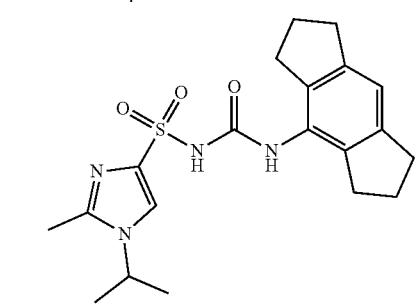
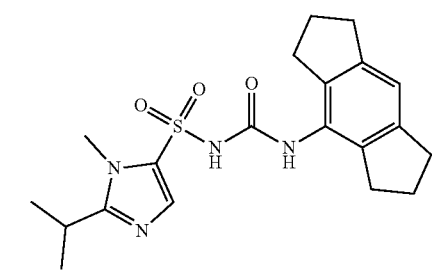
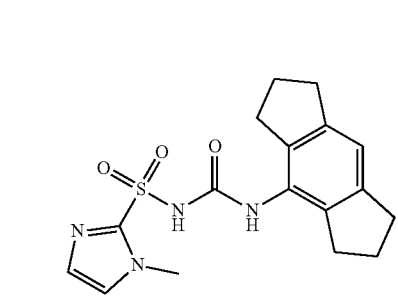
-continued
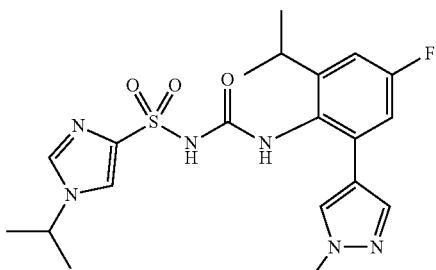
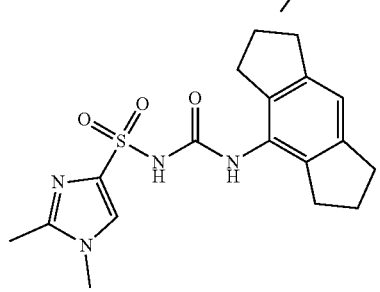
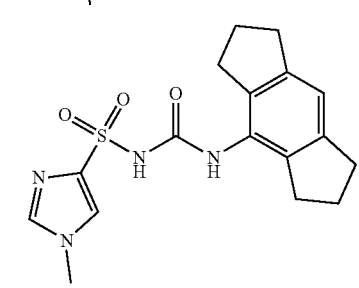
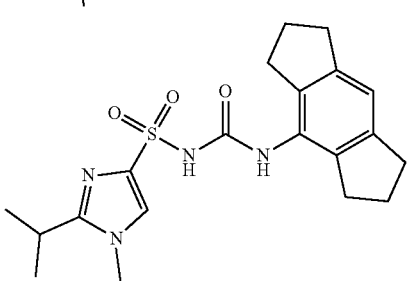
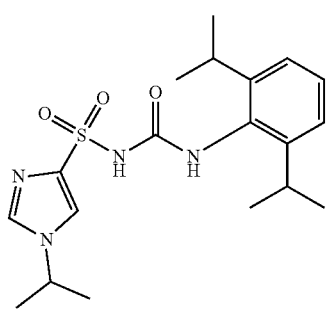
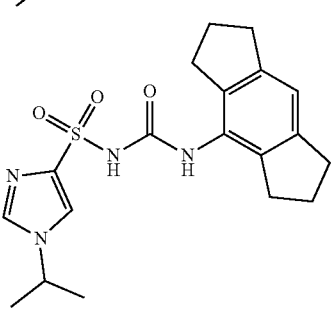

-continued

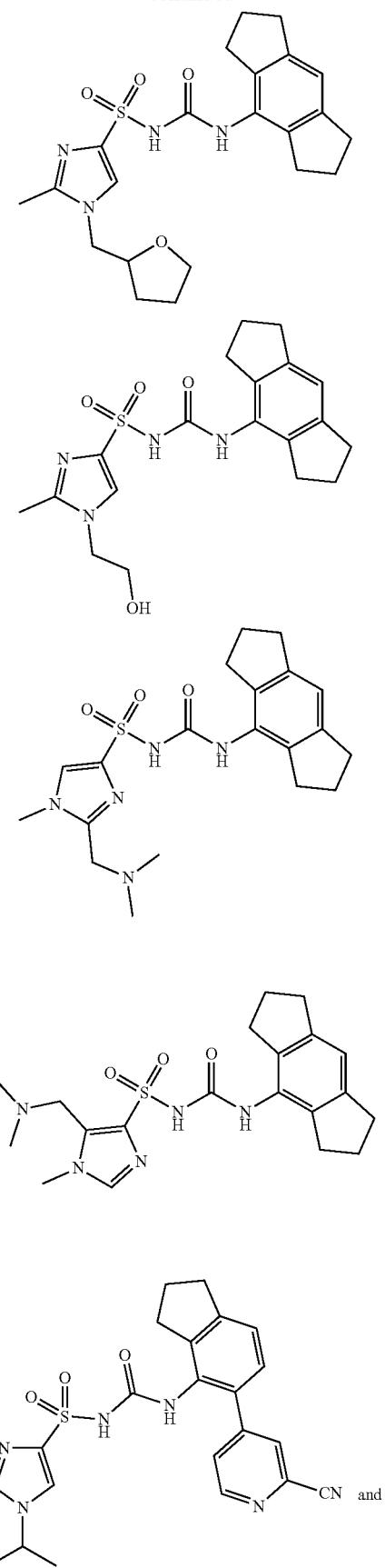

-continued

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphor-sulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, $4^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3:1-10; Inoue et al., Immunology 139:11-18, Coll et al. Nat. Med. 2015 21(31:248-55; and Scott et al. Clin. Exp. Rheumatol 2016 34(1): 88-93), systemic lupus eiythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al, Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al, Nature, 464:1357-1361, 2010; Strowig et al, Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149(4): 847-59), diabetic retinopathy (Loukovaara et al. Acta Ophthalmol. 2017; 95(8): 803-808) and optic nerve damage (Puyang et al. Sci Rep. 216 February 1956:20998); liver diseases including non-alcoholic steatohepatitis (NASH) (Henao-Meija et al., Nature, 482:179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): 60122272); and inflammatory bowel diseases including ulcerative colitis and Crohn's disease (Braddock et al., Nat. Rev. Drug Disc., 3:1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166:1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13:1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behcet's disease, Chagas' disease, dysautonomia, endometriosis, hidradenitis suppurativa (HS), interstitial cystitis, neuromyotonia, sarcoidosis, psoriasis, scleroderma, ulcerative colitis, Schnitzler syndrome, macrophage activation syndrome, Blau syndrome, vitiligo or vulvodynia;

(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetard, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsn, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *Schistosoma*, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;

(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD), and non-alcoholic steatohepatitis (NASH) including advanced fibrosis stages F3 and F4; alcoholic fatty liver disease (AFLD), and alcoholic steatohepatitis (ASH);

(x) renal diseases including chronic kidney disease, oxalate nephropathy, nephrocalcinosis, glomerulonephritis, and diabetic nephropathy;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease;

(xiv) psychological disorders such as depression and psychological stress;

(xv) graft versus host disease;

(xvi) allodynia including mechanical allodynia; and (xvii) any disease where an individual has been determined to carry a germline or somatic non-silent mutation in NLRP3.

In one embodiment, the disease, disorder or condition is selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease; and
(xvi) any disease where an individual has been determined to carry a germline or somatic non-silent mutation in NLRP3.

In another embodiment, the disease, disorder or condition is selected from:
(i) inflammation;
(ii) an auto-immune disease;
(iii) cancer;
(iv) a metabolic disease;
(v) a cardiovascular disease;
(vi) a respiratory disease;
(vii) a non-infectious liver disease;
(viii) a renal disease;
(ix) an ocular disease;
(x) a skin disease;
(xi) a psychological disorder;
(xii) a lymphatic condition; and/or
(xiii) any disease, disorder or condition in which an individual has been determined to carry a germline or somatic non-silent mutation in NLRP3.

In a further embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
(iii) a muscular condition such as polymyositis or myasthenia gravis; (iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);
(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;
(vi) a vascular condition such as atherosclerosis, Behcet's disease, vasculitides, or wegener's granulomatosis;
(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;
(viii) an ocular condition such as uveitis, allergic conjunctivitis, or vernal conjunctivitis;
(ix) a nervous condition such as multiple sclerosis or encephalomyelitis;
(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *Legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, pred-nimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, *Catharanthus roseus* (formerly known as *Vinca rosea*), and may be selected from vincristine, vinblastine, vinorelbine and/orvindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatoiy agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TLiA, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PDi), nivolumab (PDi), atezolizumab (formerly MPDL3280A) (PD-L1), MEDI4736 (PD-L1), avelumab (PD-L1), PDR001 (PDi), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

By way of example, combinations of aspects and embodiments that are typical of the present invention include the following.

In a first combination, a compound of the first aspect of the invention is provided wherein $R^2$ is a cyclic group substituted at the $\alpha$ and $\alpha'$ positions, wherein $R^2$ may optionally be further substituted. Typically in such a combination, the imidazolyl group of $R^1$ is substituted with one or more monovalent substituents.

In a second combination, a compound of the first aspect of the invention is provided wherein $R^1$ is an imidazol-2-yl group, an imidazol-4-yl group or an imidazol-5-yl group, wherein the imidazolyl group is unsubstituted or substituted with one or more monovalent substituents, and $R^2$ is a cyclic group substituted at the α and α' positions, wherein $R^2$ may optionally be further substituted. Typically in such a combination, the imidazolyl group of $R^1$ is substituted with one or more monovalent substituents.

In a third combination, a compound of the first aspect of the invention is provided wherein $R^1$ is an imidazol-4-yl group or an imidazol-5-yl group, wherein the imidazolyl group is substituted with one or more acyclic monovalent substituents.

In a fourth combination, a compound of the first aspect of the invention is provided wherein $R^1$ is an imidazol-4-yl group or an imidazol-5-yl group, wherein the imidazolyl group is substituted with one or more monovalent substituents, and wherein each monovalent substituent is independently selected from a saturated hydrocarbyl group, wherein the saturated hydrocarbyl group may be straight-chained or branched, or be or include cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton.

A fifth combination provides a compound of the first or second aspect of the invention, or a pharmaceutically acceptable salt, solvate or prodrug of the third aspect of the invention, or a pharmaceutical composition of the fourth aspect of the invention, wherein $R^1$ is an imidazol-4-yl group or an imidazol-5-yl group, wherein the imidazolyl group is unsubstituted or substituted with one or more monovalent substituents, for use in medicine. Typically in such a combination, the imidazolyl group of $R^1$ is substituted with one or more monovalent substituents.

A sixth combination provides a compound of the first or second aspect of the invention, or a pharmaceutically acceptable salt, solvate or prodrug of the third aspect of the invention, or a pharmaceutical composition of the fourth aspect of the invention, wherein the imidazolyl group of $R^1$ is substituted with two or three monovalent substituents, for use in medicine.

A sixth combination provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition, wherein the disease, disorder or condition is selected from:
 (i) inflammation;
 (ii) an auto-immune disease;
 (iii) cancer;
 (iv) a metabolic disease;
 (v) a cardiovascular disease;
 (vi) a respiratory disease;
 (vii) a non-infectious liver disease;
 (viii) a renal disease;
 (ix) an ocular disease;
 (x) a skin disease;
 (xi) a psychological disorder;
 (xii) a lymphatic condition; and/or
 (xiii) any disease, disorder or condition in which an individual has been determined to carry a germline or somatic non-silent mutation in NLRP3.

Typically in such a combination, the imidazolyl group of $R^1$ is substituted with one or more monovalent substituents.

A seventh combination provides a compound of the first or second aspect of the invention, or a pharmaceutically acceptable salt, solvate or prodrug of the third aspect of the invention, or a pharmaceutical composition of the fourth aspect of the invention, wherein $R^1$ is an imidazol-2-yl group, an imidazol-4-yl group or an imidazol-5-yl group, wherein the imidazolyl group is unsubstituted or substituted with one or more monovalent substituents, for use in the treatment or prevention of a disease, disorder or condition, wherein the disease, disorder or condition is selected from:
 (i) inflammation;
 (ii) an auto-immune disease;
 (iii) cancer;
 (iv) a metabolic disease;
 (v) a cardiovascular disease;
 (vi) a respiratory disease;
 (vii) a non-infectious liver disease;
 (viii) a renal disease;
 (ix) an ocular disease;
 (x) a skin disease;
 (xi) a psychological disorder;
 (xii) a lymphatic condition; and/or
 (xiii) any disease, disorder or condition in which an individual has been determined to carry a germline or somatic non-silent mutation in NLRP3.

Typically in such a combination, the imidazolyl group of $R^1$ is substituted with one or more monovalent substituents.

Typically, in any of the above exemplary combinations, Q is O.

Typically, in any of the above exemplary combinations, $R^1$ contains from 6 to 20 atoms other than hydrogen or halogen.

Typically, in any of the above exemplary combinations, $R^2$ is an aryl or a heteroaryl group, wherein the aryl or the heteroaryl group is substituted at the α and α' positions, and wherein $R^2$ may optionally be further substituted. Typically, each substituent at the α and α' positions comprises a carbon atom. Typically in any of the above exemplary combinations, $R^2$ contains from 9 to 20 atoms other than hydrogen or halogen.

As will be appreciated the above combinations are exemplary only and other combinations of aspects and embodiments, including combinations of the above combinations, may readily be envisaged.

EXAMPLES—COMPOUND SYNTHESIS

All solvents, reagents and compounds were purchased and used without further purification unless stated otherwise.

Abbreviations
2-MeTHF 2-methyltetrahydrofuran
Ac$_2$O acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMA dimethylacetamide DMAP 4-dimethylaminopyridine, also called N,N-dimethylpyridin-4-amine
DME dimethoxyethane
DMF N,N-dimethylformamide
DMSO dimethyl sulfoxide
eq or equiv equivalent
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaO$^t$Bu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
$^1$H NMR nuclear magnetic resonance (spectroscopy)
Pd(dba)$_3$ tris(dibenzylideneacetone) dipalladium(0)
Pd(dppf)Cl$_2$ [1,1'-bis(diphenylphosphino)ferrocene]dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight
Experimental Methods
Nuclear Magnetic Resonance
$^1$H NMR spectra were recorded at 300, 400 or 500 MHz. Spectra were measured at 298 K, unless indicated otherwise, and were referenced relative to the solvent resonance. The chemical shifts are reported in parts per million. Spectra were recorded using one of the following machines:

a Bruker Avance III spectrometer at 400 MHz fitted with a BBO 5 mm liquid probe, a Bruker 400 MHz spectrometers using ICON-NMR, under TopSpin program control, a Bruker Avance III HD spectrometer at 500 MHz, equipped with a Bruker 5 mm SmartProbe™, an Agilent VNMRS 300 instrument fitted with a 7.05 Tesla magnet from Oxford instruments, indirect detection probe and direct drive console including PFG module, or an Agilent MercuryPlus 300 instrument fitted with a 7.05 Tesla magnet from Oxford instruments, 4 nuclei auto-switchable probe and Mercury plus console.

LC-MS

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% NH$_3$—H$_2$O in water (v/v); B: acetonitrile. Column: Kinetex EVO C18 2.1×30 mm, 5 µm.

Reversed Phase HPLC Conditions for the LCMS Analytical Methods

Methods 1a and 1b: Waters Xselect CSH C18 XP column (4.6×30 mm, 2.5 µm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% water-5% acetonitrile to 5% water-95% acetonitrile; 3.00-3.01 min, held at 5% water-95% acetonitrile, flow rate increased to 4.5 mL min$^{-1}$; 3.01-3.50 min, held at 5% water-95% acetonitrile; 3.50-3.60 min, returned to 95% water-5% acetonitrile, flow rate reduced to 3.50 mL min$^{-1}$; 3.60-3.90 min, held at 95% water-5% acetonitrile; 3.90-4.00 min, held at 95% water-5% acetonitrile, flow rate reduced to 2.5 mL min$^{-1}$.

Method 1c: Agilent 1290 series with UV detector and HP 6130 MSD mass detector using Waters XBridge BEH C18 XP column (2.1×50 mm, 2.5 µm) at 35° C.; flow rate 0.6 mL/min; mobile phase A: ammonium acetate (10 mM); water/MeOH/acetonitrile (900:60:40); mobile phase B: ammonium acetate (10 mM); water/MeOH/acetonitrile (100:540:360); over 4 min employing UV detection at 215 and 238 nm. Gradient information: 0-0.5 min, held at 80% A-20% B; 0.5-2.0 min, ramped from 80% A-20% B to 100% B.

Reversed Phase HPLC Conditions for the UPLC Analytical Methods

Methods 2a and 2b: Waters BEH C18 (2.1×30 mm, 1.7 µm) at 40° C.; flow rate 0.77 mL min$^{-1}$ eluted with a H$_2$O-MeCN gradient containing either 0.1% v/v formic acid (Method 2a) or 10 mM NH$_4$HCO$_3$ in water (Method 2b) over 3 min employing UV detection at 254 nm. Gradient information: 0-0.11 min, held at 95% water-5% acetonitrile, flow rate 0.77 mL min$^{-1}$; 0.11-2.15 min, ramped from 95% water-5% acetonitrile to 5% water-95% acetonitrile; 2.15-2.49 min, held at 5% water-95% acetonitrile, flow rate 0.77 mL min$^{-1}$; 2.49-2.56 min, returned to 95% water-5% acetonitrile; 2.56-3.00 min, held at 95% water-5% acetonitrile, flow rate reduced to 0.77 mL min$^{-1}$.

Preparative Reversed Phase HPLC General Methods

Method 1 (acidic preparation): Waters X-Select CSH column C18, 5 µm (19×50 mm), flow rate 28 mL min$^{-1}$ eluting with a H$_2$O-MeCN gradient containing 0.1% v/v formic acid over 6.5 min using UV detection at 254 nm.

Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Method 2 (basic preparation): Waters X-Bridge Prep column C18, 5 μm (19×50 mm), flow rate 28 mL min$^{-1}$ eluting with a 10 mM NH$_4$HCO$_3$-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

Method 3: Phenomenex Gemini column, 10 μm (150×25 mm), flow rate=25 mL/min eluting with a water-acetonitrile gradient containing 0.04% NH$_3$ at pH 10 over 9 minutes using UV detection at 220 and 254 nm. Gradient information: 0-9 minutes, ramped from 8% to 35% acetonitrile; 9-9.2 minutes, ramped from 35% to 100% acetonitrile; 9.2-15.2 minutes, held at 100% acetonitrile.

Method 4: Revelis C18 reversed-phase 12 g cartridge [carbon loading 18%; surface area 568 m$^2$/g; pore diameter 65 Angstrom; pH (5% slurry) 5.1; average particle size 40 μm], flow rate=30 mL/min eluting with a water-methanol gradient over 35 minutes using UV detection at 215, 235, 254 and 280 nm. Gradient information: 0-5 minutes, held at 0% methanol; 5-30 minutes, ramped from 0% to 70% methanol; 30-30.1 minutes, ramped from 70% to 100% methanol; 30.1-35 minutes, held at 100% methanol.

Synthesis of Intermediates

Intermediate P1: (R)-1-(2-Hydroxypropyl)-1H-imidazole-4-sulfonamide

Step A: N,N-Bis(4-methoxybenzyl)-1H-imidazole-4-sulfonamide

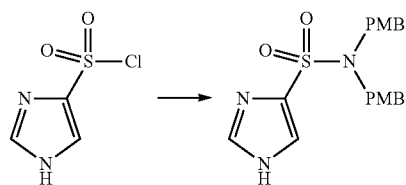

A solution of 1H-imidazole-4-sulfonyl chloride (2.5 g, 15.01 mmol) in DCM (10 mL) was added slowly to a solution of bis(4-methoxybenzyl)amine (4 g, 15.54 mmol) and Et$_3$N (4.5 mL, 32.3 mmol) in DCM (50 mL) cooled in an ice bath. The mixture was stirred for 30 minutes, warmed to room temperature and stirred for 2 hours. The DCM was removed under pressure and replaced with dioxane (50 mL) and the mixture heated under reflux for 48 hours, cooled, and then partitioned between EtOAc (200 mL) and water (200 mL). The organic layer was dried (MgSO$_4$), filtered and evaporated to give an oil that was purified by chromatography on silica gel (120 g column, 0-100% EtOAc/isohexane). The product was triturated in TBME/EtOAc, filtered and dried to afford the title compound (2.864 g, 48%) as a solid.

$^1$H NMR (CDCl$_3$) δ 7.92 (d, J=1.3 HZ, 1H), 7.52 (d, J=1.3 HZ, 1H), 7.06-7.02 (m, 4H), 6.79-6.75 (m, 4H), 4.30 (s, 4H), 3.77 (s, 6H). Exchangeable proton not visible.

LCMS; m/z 388 (M+H)$^+$ (ES$^+$); 386 (M−H)$^-$ (ES$^-$).

Step B: (R)-1-(2-Hydroxypropyl)-N,N-bis(4-methoxybenzyl)-1H-imidazole-4-sulfonamide

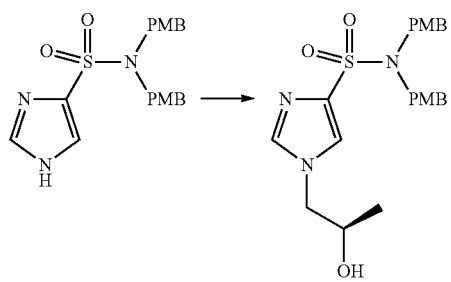

A mixture of N,N-bis(4-methoxybenzyl)-1H-imidazole-4-sulfonamide (500 mg, 1.29 mmol), (R)-2-methyloxirane (0.18 ml, 2.57 mmol) and K$_2$CO$_3$ (535 mg, 3.87 mmol) in acetonitrile (10 mL) was stirred at 60° C. overnight. Upon cooling to room temperature, the reaction mixture was diluted with H$_2$O (20 mL) and extracted with EtOAc (3×50 mL). The combined organic extracts were washed with brine (30 mL), passed through a phase separator, and concentrated in vacuo. The residue was loaded onto silica and purified by chromatography on silica gel (40 g column, 0-100% EtOAc/isohexane) to afford the title compound (468 mg, 68%) as a clear colourless oil.

$^1$H NMR (DMSO-d$_6$) δ 7.82 (d, J=1.3 Hz, 1H), 7.81 (d, J=1.3 Hz, 1H), 7.03 (d, J=8.6 Hz, 4H), 6.80 (d, J=8.6 Hz, 4H), 4.18 (s, 4H), 4.06-4.00 (m, 2H), 3.95-3.86 (m, 2H), 3.71 (s, 6H), 1.04 (d, J=5.9 Hz, 3H).

LCMS; m/z 446.4 (M+H)$^+$ (ES$^+$).

Step C: (R)-1-(2-Hydroxypropyl)-1H-imidazole-4-sulfonamide

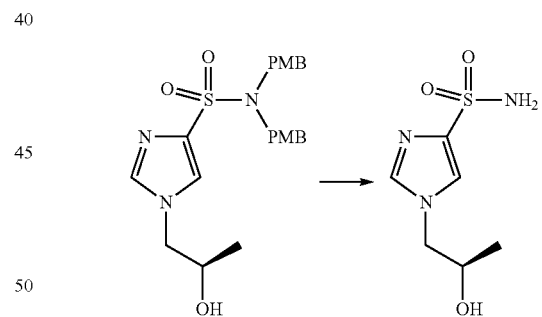

A mixture of (R)-1-(2-hydroxypropyl)-N,N-bis(4-methoxybenzyl)-1H-imidazole-4-sulfonamide (460 mg, 0.857 mmol) and TFA (5.5 mL) was stirred at room temperature for 2 days. The reaction mixture was concentrated in vacuo and the residue loaded onto silica and purified by chromatography on silica gel (12 g column, 0-10% MeOH/DCM) to afford a clear colourless oil, which was further purified by prep-HPLC to afford the title compound (123 mg, 68%) as a clear colourless oil.

$^1$H NMR (DMSO-d$_6$) δ 7.71 (d, J=1.3 Hz, 1H), 7.59 (d, J=1.3 Hz, 1H), 7.12 (s, 2H), 5.00 (d, J=4.1 Hz, 1H), 4.07-3.96 (m, 1H), 3.93-3.79 (m, 2H), 1.03 (d, J=6.0 Hz, 3H).

LCMS; m/z 206.2 (M+H)$^+$ (ES$^+$).

Intermediate P2: (S)-1-(2-Hydroxypropyl)-1H-imidazole-4-sulfonamide

Step A: (S)-1-(2-Hydroxypropyl)-N,N-bis(4-methoxybenzyl)-1H-imidazole-4-sulfonamide

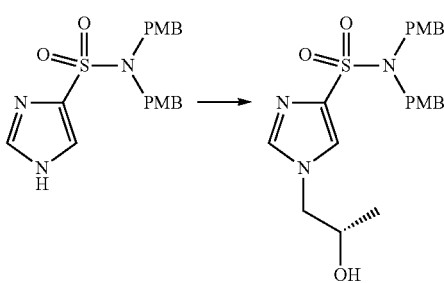

Prepared according to the general procedure of (R)-1-(2-hydroxypropyl)-N,N-bis(4-methoxybenzyl)-1H-imidazole-4-sulfonamide (Intermediate P1, Step B) from N,N-bis(4-methoxybenzyl)-1H-imidazole-4-sulfonamide (Intermediate P1, Step A) and (S)-2-methyloxirane to afford the title compound (160 mg, 37%) as a clear colourless oil.

$^1$H NMR (DMSO-$d_6$) δ 7.81 (d, J=1.2 Hz, 1H), 7.80 (d, J=1.2 Hz, 1H), 7.02 (d, J=8.7 Hz, 4H), 6.80 (d, J=8.7 Hz, 4H), 5.04 (d, J=4.6 Hz, 1H), 4.18 (s, 4H), 4.06-3.99 (m, 1H), 3.97-3.84 (m, 2H), 3.71 (s, 6H), 1.04 (d, J=5.9 Hz, 3H).

LCMS; m/z 446.2 (M+H)$^+$ (ES$^+$).

Step B: (S)-1-(2-Hydroxypropyl)-1H-imidazole-4-sulfonamide

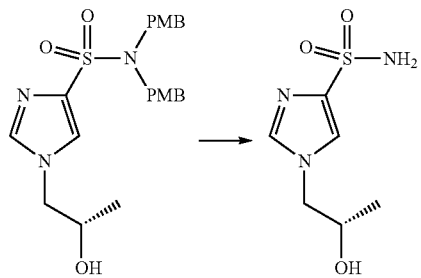

Prepared according to the general procedure of (R)-1-(2-hydroxypropyl)-1H-imidazole-4-sulfonamide (Intermediate P1, Step C) from (S)-1-(2-hydroxypropyl)-N,N-bis(4-methoxybenzyl)-1H-imidazole-4-sulfonamide to afford the title compound (56 mg, 70%) as a clear colourless oil.

$^1$H NMR (DMSO-$d_6$) δ 7.71 (d, J=1.3 Hz, 1H), 7.59 (d, J=1.3 Hz, 1H), 7.11 (s, 2H), 5.00 (d, J=4.6 Hz, 1H), 4.04-3.95 (m, 1H), 3.92-3.80 (m, 2H), 1.03 (d, J=6.0 Hz, 3H).

LCMS; m/z 206.2 (M+H)$^+$ (ES$^+$).

Intermediate P3: 1-(2-(Dimethylamino)ethyl)-1H-imidazole-4-sulfonamide

Step A: N,N-Bis(4-methoxybenzyl)-1H-imidazole-4-sulfonamide

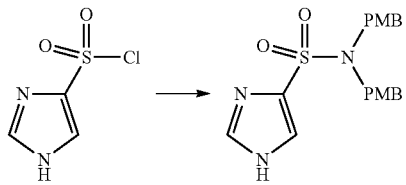

A solution of 1H-imidazole-4-sulfonyl chloride (2.5 g, 15.01 mmol) in DCM (10 mL) was added slowly to a solution of bis(4-methoxybenzyl)amine (4 g, 15.54 mmol) and Et$_3$N (4.5 mL, 32.3 mmol) in DCM (50 mL) cooled in an ice bath. The mixture was stirred for 30 minutes, warmed to room temperature and stirred for 2 hours. The DCM was removed under pressure and replaced with dioxane (50 mL). Then the reaction mixture was heated under reflux for 48 hours, cooled and partitioned between EtOAc (200 mL) and water (200 mL). The organic layer was dried (MgSO$_4$), filtered and evaporated to give an oil that was purified by chromatography on silica gel (120 g column, 0-100% EtOAc/isohexane). The product was triturated in TBME/EtOAc, filtered and dried to afford the title compound (2.864 g, 48%) as a solid.

$^1$H NMR (CDCl$_3$) δ 7.92 (d, J=1.3 HZ, 1H), 7.52 (d, J=1.3 HZ, 1H), 7.06-7.02 (m, 4H), 6.79-6.75 (m, 4H), 4.30 (s, 4H), 3.77 (s, 6H). Exchangeable proton not visible.

LCMS; m/z 388 (M+H)$^+$ (ES$^+$); 386 (M–H)$^-$ (ES$^-$).

Step B: 1-(2-Hydroxyethyl)-N,N-bis(4-methoxybenzyl)-1H-imidazole-4-sulfonamide

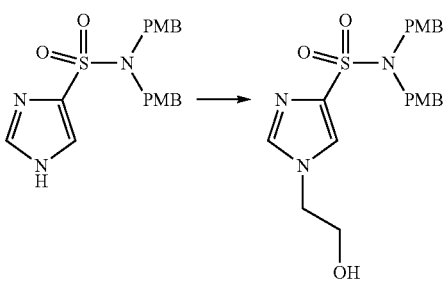

A mixture of N,N-bis(4-methoxybenzyl)-1H-imidazole-4-sulfonamide (1 g, 2.58 mmol), oxirane (2.5 M in THF) (2 mL, 5.00 mmol) and K$_2$CO$_3$ (1.07 g, 7.74 mmol) in acetonitrile (20 mL) was stirred at 50° C. for 3 days. Upon cooling to room temperature, the reaction mixture was diluted with H$_2$O (40 mL) and extracted with EtOAc (3×80 mL). The combined organic extracts were washed with brine (50 mL), passed through a phase separator and the solvent was removed in vacuo. The residue was loaded onto silica and purified by chromatography on silica gel (40 g column, 0-100% EtOAc/isohexane, eluting at 100%) to afford the title compound (679 mg, 61%) as a clear colourless solid.

$^1$H NMR (DMSO-$d_6$) δ 7.85 (d, J=1.3 Hz, 1H), 7.84 (d, J=1.3 Hz, 1H), 7.03 (d, J=8.7 Hz, 4H), 6.80 (d, J=8.7 Hz,

4H), 5.04 (t, J=5.1 Hz, 1H), 4.18 (s, 4H), 4.08 (t, J=5.3 Hz, 2H), 3.71 (s, 6H), 3.70-3.66 (m, 2H).
LCMS; m/z 432.4 (M+H)+ (ES+).

Step C: 1-(2-(Dimethylamino)ethyl)-N,N-bis(4-methoxybenzyl)-1H-imidazole-4-sulfonamide

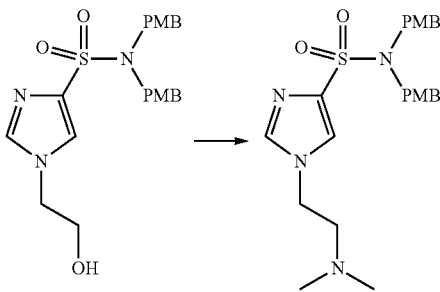

To a solution of 1-(2-hydroxyethyl)-N,N-bis(4-methoxybenzyl)-1H-imidazole-4-sulfonamide (675 mg, 1.564 mmol) in DCM (8 mL) at 0° C. was added DIPEA (0.41 mL, 2.348 mmol) and methanesulfonyl chloride (0.16 mL, 2.053 mmol). The reaction mixture was warmed to room temperature and stirred for 2 hours before being quenched by addition of aqueous NaHCO₃ (10 mL). The reaction mixture was extracted twice with DCM (15 mL) and the combined organic extracts were passed through a phase separator and concentrated in vacuo. The orange residue was dissolved in THF (8 mL), dimethylamine (2M in THF) (2.4 mL, 4.80 mmol) and potassium iodide (130 mg, 0.782 mmol) were added, and the reaction mixture was heated to 60° C. and stirred overnight. Additional dimethylamine (2M in THF) (2.4 mL, 4.80 mmol) was added and stirring was continued overnight. The reaction mixture was diluted with aqueous NaHCO₃ (20 mL) and extracted with EtOAc (3×40 mL). The combined organic extracts were passed through a phase separator and the solvent was removed in vacuo. The residue was dissolved in MeOH (30 mL), SCX (~12 g) was added and the suspension was stirred at room temperature for 30 minutes. The mixture was transferred into a cartridge, sequentially washed with DCM/MeOH (9:1) and MeOH, and the product was eluted with 0.7 M NH₃ in MeOH to afford the title compound (585 mg, 73%) as a yellow oil.
¹H NMR (DMSO-d₆) δ 7.87 (s, 2H), 7.02 (d, J=8.7 Hz, 4H), 6.79 (d, J=8.7 Hz, 4H), 4.18 (s, 4H), 4.12 (t, J=6.2 Hz, 2H), 3.71 (s, 6H), 2.58 (t, J=6.2 Hz, 2H), 2.18 (s, 6H).
LCMS; m/z 459.0 (M+H)+ (ES+).

Step D: 1-(2-(Dimethylamino)ethyl)-1H-imidazole-4-sulfonamide

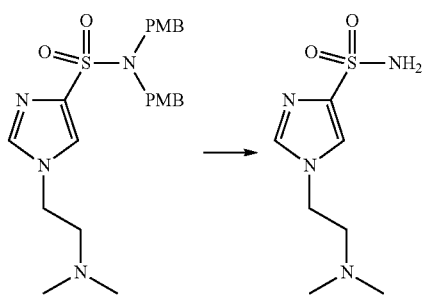

A mixture of 1-(2-(dimethylamino)ethyl)-N,N-bis(4-methoxybenzyl)-1H-imidazole-4-sulfonamide (585 mg, 1.135 mmol) and TFA (4 mL, 62.8 mmol) was stirred at room temperature overnight. The mixture was evaporated and the residue was dissolved in MeOH (30 mL) and DCM (10 mL). SCX (8 g) was added and the mixture was stirred for 30 minutes at room temperature, transferred to a cartridge and the solid washed sequentially with DCM:MeOH (9:1) and MeOH. The product was eluted with 0.7 M NH₃ in MeOH to give crude product, which was further purified by chromatography on silica gel (24 g column, 0-10% (0.7 M ammonia/MeOH/DCM) to afford the title compound (180 mg, 72%) as a pale yellow oil.
¹H NMR (DMSO-d₆) δ 7.77 (d, J=1.4 Hz, 1H), 7.66 (d, J=1.3 Hz, 1H), 7.11 (s, 2H), 4.09 (t, J=6.1 Hz, 2H), 2.56 (t, J=6.1 Hz, 2H), 2.17 (s, 6H).
LCMS; m/z 219.3 (M+H)+ (ES+).

Intermediate P4: (4-(Dimethylamino)pyridin-1-ium-1-carbonyl)((1-isopropyl-1H-imidazol-4-yl)sulfonyl)amide

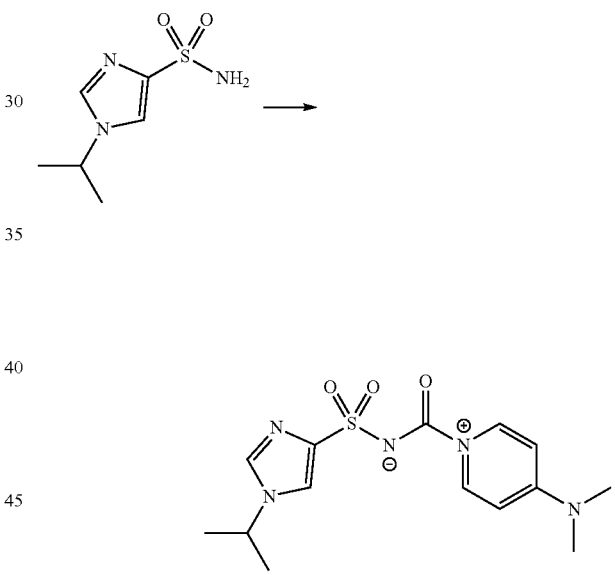

A solution of 1-iso-propyl-1H-imidazole-4-sulfonamide (161 mg, 0.851 mmol) in acetonitrile (1 mL) was treated with N,N-dimethylpyridin-4-amine (208 mg, 1.702 mmol) and the reaction mixture was stirred at room temperature until sulfonamide had dissolved. Then diphenyl carbonate (200 mg, 0.936 mmol) was added and the reaction mixture was left for 16 hours at room temperature. The resulting precipitate was separated by filtration, washed with methyl tert-butylether and dried to afford the title compound (186 mg, 65%) as a white solid which was used without further purification.

Intermediate P5: 2-((Dimethylamino)methyl)-1-methyl-1H-imidazole-4-sulfonamide, and Intermediate P6: 5-((Dimethylamino)methyl)-1-methyl-1H-imidazole-4-sulfonamide Step A: N,N-Bis(4-methoxybenzyl)-1-methyl-1H-imidazole-4-sulfonamide

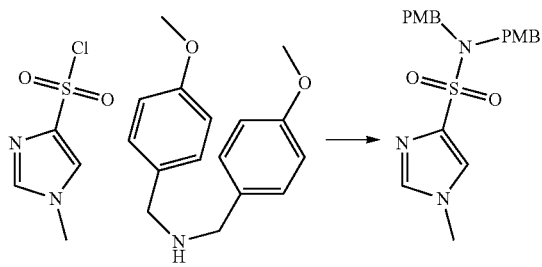

1-Methyl-1H-imidazole-4-sulfonyl chloride (4 g, 22.15 mmol) was added portionwise to a solution of bis(4-methoxybenzyl)amine (5.98 g, 23.25 mmol) and triethylamine (6.17 ml, 44.3 mmol) in DCM (100 mL) cooled in an ice bath. The mixture was stirred for 30 minutes, warmed to room temperature and stirred for 16 hours. The mixture was washed with water (2×50 mL), aq 1 M HCl (50 mL), water (50 mL), and brine (50 mL), then dried over MgSO$_4$, filtered and evaporated to dryness to give crude product as a cream coloured solid. The crude product was dissolved in a minimum amount of DCM to load, then purified by column chromatography on silica gel (220 g column, 0-80% EtOAc/isohexane) to afford the title compound (5.1 g, 55%) as a white solid.

$^1$H NMR (DMSO-d$_6$) δ 7.87-7.78 (m, 2H), 7.09-6.99 (m, 4H), 6.91-6.73 (m, 4H), 4.19 (s, 4H), 3.72 (s, 6H), 3.33 (s, 3H).

LCMS; m/z 402.3 (M+H)$^+$ (ES$^+$).

Step B: 2-((Dimethylamino)methyl)-N,N-bis(4-methoxybenzyl)-1-methyl-1H-imidazole-4-sulfonamide and 5-((dimethylamino)methyl)-N,N-bis(4-methoxybenzyl)-1-methyl-1H-imidazole-4-sulfonamide

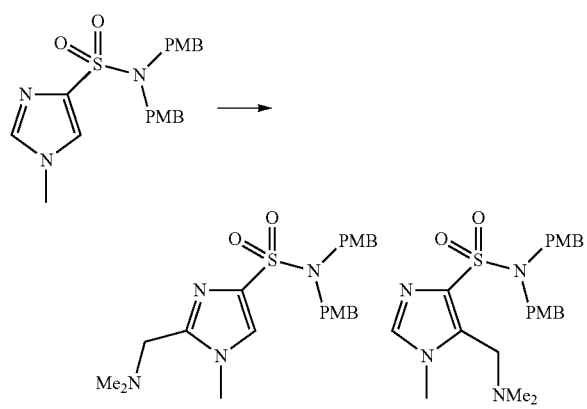

A solution of n-BuLi (2.5M in hexanes) (1.046 mL, 2.62 mmol) was added dropwise to a stirred solution of N,N-bis(4-methoxybenzyl)-1-methyl-1H-imidazole-4-sulfonamide (1 g, 2.491 mmol) in THF (14 mL) at −78° C. The reaction was stirred for 1 hour and then N-methyl-N-methylenemethanaminium iodide (0.922 g, 4.98 mmol) was added. The reaction mixture was left at −78° C. for 1 hour. The reaction was quenched with water (20 mL) and extracted with EtOAc (2×20 mL). The combined organic layers were dried over MgSO$_4$, filtered and concentrated to dryness. The crude product was purified by chromatography on silica gel (24 g column, 0-5% MeOH/DCM) to afford an inseparable 85:15 mixture of 2-((dimethylamino)methyl)-N,N-bis(4-methoxybenzyl)-1-methyl-1H-imidazole-4-sulfonamide and 5-((dimethylamino)methyl)-N,N-bis(4-methoxybenzyl)-1-methyl-1H-imidazole-4-sulfonamide (374 mg, 27.8%) as a yellow oil.

$^1$H NMR (major product) (DMSO-d$_6$) δ 7.83 (s, 1H), 7.05-6.98 (m, 4H), 6.83-6.74 (m, 4H), 4.24 (s, 4H), 3.71 (s, 6H), 3.70 (s, 3H), 3.68 (s, 2H), 2.16 (s, 6H).

m/z 459.4 (M+H)$^+$ (ES$^+$).

Step C: 2-((Dimethylamino)methyl)-1-methyl-1H-imidazole-4-sulfonamide & 5-((dimethylamino)methyl)-1-methyl-1H-imidazole-4-sulfonamide

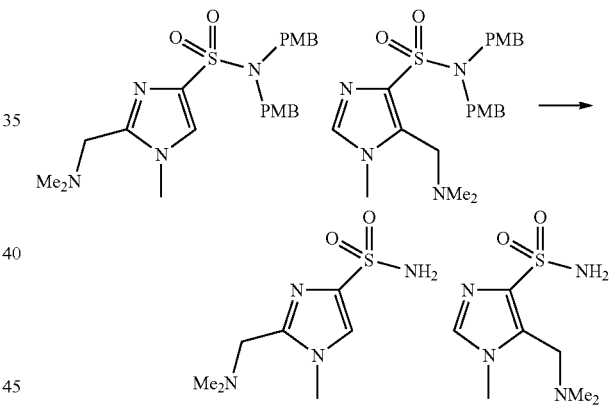

A 85:15 mixture of 2-((dimethylamino)methyl)-N,N-bis(4-methoxybenzyl)-1-methyl-1H-imidazole-4-sulfonamide and 5-((dimethylamino)methyl)-N,N-bis(4-methoxybenzyl)-1-methyl-1H-imidazole-4-sulfonamide (552 mg, 1.204 mmol) was dissolved in TFA (5 ml, 1.204 mmol) and stirred overnight. Additional TFA (2 mL) was added and stirred for a further 24 hours at room temperature. The mixture was concentrated in vacuo and the residue was suspended in a mixture of MeOH (50 mL) and DCM (10 mL). SCX (3 eq.) was added and the suspension was stirred at room temperature for 1 hour. The SCX was filtered and washed with MeOH (50 mL) and the product was then eluted with 0.7% ammonia in MeOH (50 mL). After concentration in vacuo, a 85:15 mixture of 2-((dimethylamino)methyl)-1-methyl-1H-imidazole-4-sulfonamide and 5-((dimethylamino)methyl)-1-methyl-1H-imidazole-4-sulfonamide (222 mg, 84%) was isolated as a pale yellow oil.

$^1$H NMR (major product) (DMSO-d$_6$) δ 7.72 (s, 1H), 7.10 (s, 2H), 3.66 (s, 3H), 3.65 (s, 2H), 2.15 (s, 6H).

Intermediate P7:
2-Isopropyl-1-methyl-1H-imidazole-5-sulfonamide,
and

Intermediate P8:
2-Isopropyl-1-methyl-1H-imidazole-4-sulfonamide

Step A: 2-Isopropyl-1-methyl-1H-imidazole-5-sulfonyl chloride and 2-isopropyl-1-methyl-1H-imidazole-4-sulfonyl chloride

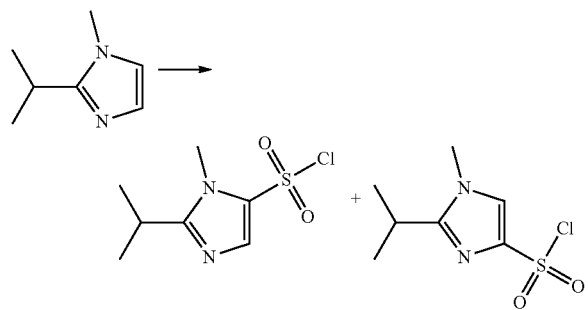

To chlorosulfonic acid (1.2 mL, 24.1 mmol) stirred in a microwave vial (20 mL) at room temperature was added 1-methyl-2-(propan-2-yl)-1H-imidazole (1.0 g, 8.0 mmol). The microwave vial was sealed and heated in a sand bath at 150° C. for 3 hours. The reaction mixture was cooled to room temperature and then thionyl chloride (0.7 mL, 9.1 mmol) was added. The reaction mixture was heated at 100° C. overnight and then cooled to room temperature and poured into ice. The aqueous mixture was neutralised with sodium bicarbonate to pH 5, and then extracted with DCM. The organic layer was washed brine, dried over Na$_2$SO$_4$, filtered and then concentrated in vacuo. The crude product was dissolved in DCM and then submitted for normal phase flash chromatography on silica using heptane and EtOAc as eluent to afford 2-isopropyl-1-methyl-1H-imidazole-5-sulfonyl (157 mg, 9%) and 2-isopropyl-1-methyl-1H-imidazole-4-sulfonyl chloride (130 mg, 7%).

$^1$H NMR for 2-isopropyl-1-methyl-1H-imidazole-5-sulfonyl chloride:
$^1$H NMR (CDCl$_3$) δ 7.55 (s, 1H), 3.70 (s, 3H), 3.12-2.95 (m, 1H), 1.37 (d, 6H).
$^1$H NMR for 2-isopropyl-1-methyl-1H-imidazole-4-sulfonyl chloride:
$^1$H NMR (CDCl$_3$) δ 7.78 (s, 1H), 3.88 (s, 3H), 3.18-2.96 (m, 1H), 1.38 (d, 6H).

Step B1:
2-Isopropyl-1-methyl-1H-imidazole-5-sulfonamide

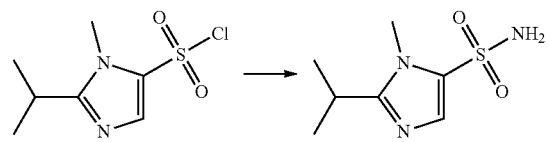

To a solution of 2-isopropyl-1-methyl-1H-imidazole-5-sulfonyl chloride (Intermediates P7 & P8, Step A) (130 mg, 0.58 mmol) in DCM (5 mL) was added 7M NH$_3$ in methanol (0.32 mL, 2.32 mmol). The reaction mixture was stirred at room temperature overnight and then concentrated in vacuo. The crude product was dissolved in methanol, coated on hydromatrix and then submitted for normal phase flash chromatography on silica using DCM and a mixture of 3.5 M NH$_3$ in methanol as eluent to afford the title compound (41 mg, 34%).

$^1$H NMR (DMSO-d$_6$) δ 7.62 (s, 2H), 7.22 (s, 1H), 3.71 (s, 3H), 3.19-3.05 (m, 1H), 1.21 (d, 6H).

Step B2:
2-Isopropyl-1-methyl-1H-imidazole-4-sulfonamide

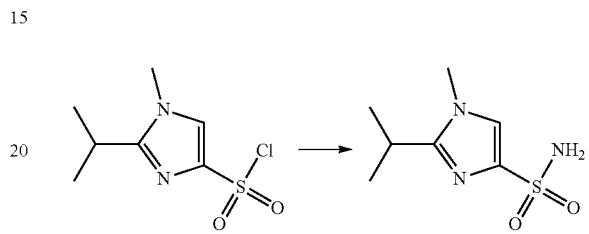

To a solution of 2-isopropyl-1-methyl-1H-imidazole-4-sulfonyl chloride (Intermediates P7 & P8, Step A) (157 mg, 0.70 mmol) in DCM (7 mL) was added 7M NH$_3$ in methanol (0.4 mL, 2.8 mmol). The reaction mixture was stirred at room temperature for 3 hours and then extra 7M NH$_3$ in methanol (0.4 mL, 2.8 mmol) was added. The mixture was stirred for an additional 4 hours and then concentrated in vacuo. The crude product was dissolved in methanol, coated on hydromatrix and then submitted for normal phase flash chromatography on silica using DCM and a mixture of 3.5 M NH$_3$ in methanol as eluent to afford the title compound (85 mg, 59%).

$^1$H NMR (DMSO-d$_6$) δ 7.50 (s, 1H), 7.05 (s, 2H), 3.62 (s, 3H), 3.09 (p, 1H), 1.21 (d, 6H).

Intermediate P9:
1-Isopropyl-2-methyl-1H-imidazole-4-sulfonamide

Step A: N,N-Bis(4-Methoxybenzyl)-2-methyl-1H-imidazole-4-sulfonamide

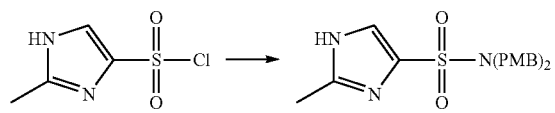

2-Methyl-1H-imidazole-4-sulfonylchloride (1 g, 5.5 mmol) was suspended in DCM (30 mL) at room temperature. To this suspension was added bis(4-methoxybenzyl)amine (1.5 g, 6 mmol) and potassium tert-butoxide (0.25 g, 2 mmol). The reaction mixture was stirred for 18 hours at room temperature, washed with water and brine, dried (Na$_2$SO$_4$), filtered and evaporated. The residue was further purified over silica (using a gradient of methanol in DCM 0-5% as eluent) to afford the title compound as a brown oil (2.4 g, 100%).

$^1$H NMR (CDCl$_3$) δ 7.37 (s, 1H), 7.07 (d, 4H), 6.76 (d, 4H), 4.30 (s, 4H), 3.80 (s, 6H), 2.43 (s, 3H).

Step B: 1-Isopropyl-N,N-bis(4-methoxybenzyl)-2-methyl-1H-imidazole-4-sulfonamide

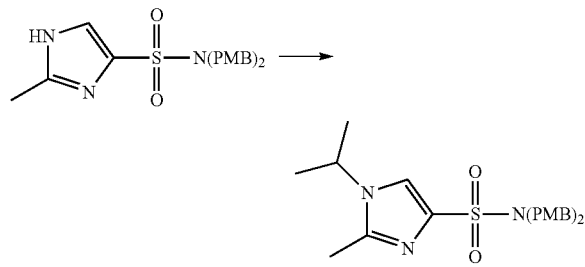

N,N-Bis(4-methoxybenzyl)-2-methyl-1H-imidazole-4-sulfonamide (250 mg, 0.63 mmol) was dissolved in DMF (10 mL). Potassium carbonate (500 mg, 3.6 mmol), followed by 2-iodopropane (0.42 g, 2.5 mmol) were added. The reaction mixture was stirred for 48 hours at room temperature and then diluted with DCM and washed with water and brine. The organic layer was dried (Na$_2$SO$_4$), filtered and evaporated. The residue was purified over silica (using a gradient of methanol in DCM 0-5% as eluent) to afford the title compound (283 mg, 100%).

$^1$H NMR (CDCl$_3$) δ 7.37 (s, 1H), 7.10 (d, 4H), 6.76 (d, 4H), 4.32 (s, 4H), 3.78 (s, 6H), 2.43 (s, 3H) 1.42 (d, 6H).

Step C: 1-Isopropyl-2-methyl-1H-imidazole-4-sulfonamide

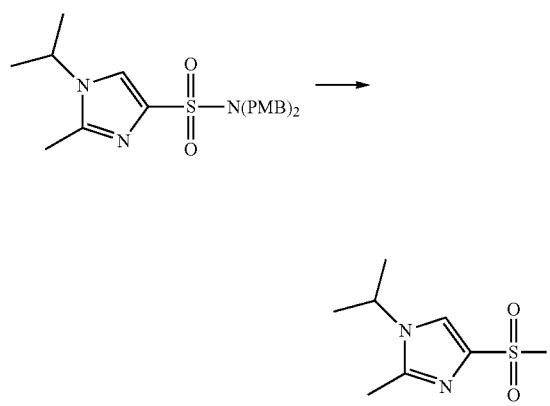

1-Isopropyl-N,N-bis(4-methoxybenzyl)-2-methyl-1H-imidazole-4-sulfonamide (0.28 g, 0.64 mmol) was dissolved in DCM (10 mL). Trifluoroacetic acid (10 mL) was added and the mixture was stirred for 18 hours at room temperature. The solvents were evaporated and to the residue was added NH$_3$ (7 M) in methanol. The solvents were evaporated and the residue was triturated with water, filtered and lyophilized. The residue was further purified over silica, using DCM and a mixture of 3.5 M NH$_3$ in methanol as the eluent to afford the title compound as a white solid (60 mg, 46%).

$^1$H NMR (CDCl$_3$) δ 748 (s, 1H), 5.03 (s, br, 2H), 4.32 (m, 1H), 2.43 (s, 3H), 1.45 (d, 6H).

Intermediate P10: 1-Ethyl-2-methyl-1H-imidazole-4-sulfonamide

Step A: 1-Ethyl-N,N-bis(4-methoxybenzyl)-2-methyl-1H-imidazole-4-sulfonamide

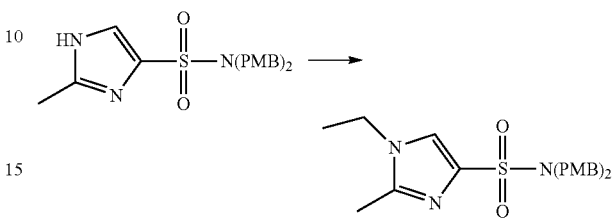

Prepared as described for 1-isopropyl-N,N-bis(4-methoxybenzyl)-2-methyl-1H-imidazole-4-sulfonamide (Intermediate P9, Step B), using N,N-bis(4-methoxybenzyl)-2-methyl-1H-imidazole-4-sulfonamide (Intermediate P9, Step A) (250 mg, 0.63 mmol) and ethyl iodide (390 mg, 2.5 mmol) to afford the title compound (280 mg, 100%).

$^1$H NMR (CDCl$_3$) δ 7.32 (s, 1H), 7.10 (d, 4H), 6.76 (d, 4H), 4.32 (s, 4H), 3.89 (q, 2H), 3.78 (s, 6H), 243 (s, 3H), 142 (t, 3H).

Step B: 1-Ethyl-2-methyl-1H-imidazole-4-sulfonamide

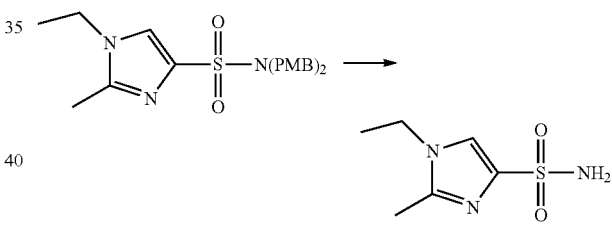

Prepared as described for 1-isopropyl-2-methyl-1H-imidazole-4-sulfonamide (Intermediate P9, Step C) using 1-ethyl-N,N-bis(4-methoxybenzyl)-2-methyl-1H-imidazole-4-sulfonamide to afford the title compound (0.28 g, 14%) as a white solid.

$^1$H NMR (CD3OD) δ 7.75 (s, 1H), 4.00 (q, 2H), 2.39 (s, 3H), 1.39 (t, 3H).

Intermediate P11: 2-Methyl-1-((tetrahydrofuran-2-yl)methyl)-1H-imidazole-4-sulfonamide

Step A: N,N-Bis(4-methoxybenzyl)-2-methyl-1-((tetrahydrofuran-2-yl)methyl)-1H-imidazole-4-sulfonamide

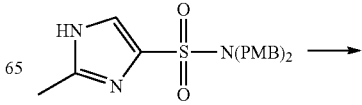

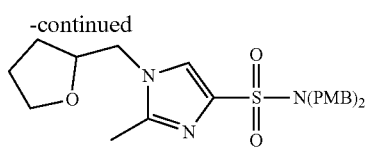

Prepared as described for 1-isopropyl-N,N-bis(4-methoxybenzyl)-2-methyl-1H-imidazole-4-sulfonamide (Intermediate P9, Step B), using N,N-bis(4-methoxybenzyl)-2-methyl-1H-imidazole-4-sulfonamide (Intermediate P9, Step A) (0.28 g, 0.64 mmol) and 3-bromomethylfuran (400 mg, 2.5 mmol) to afford the title compound (242 mg, 78%) as a solid.

$^1$H NMR (CDCl$_3$) δ 7.45 (s, 1H), 7.10 (d, 4H), 6.76 (d, 4H), 4.32 (s, 4H), 3.97 (dd, 1H), 3.82 (m, 2H), 3.78 (s, 6H), 2.44 (s, 3H), 2.07 (m, 1H), 1.89 (m, 2H), 1.61 (m, 1H).

Step B: 2-Methyl-1-((tetrahydrofuran-2-yl)methyl)-1H-imidazole-4-sulfonamide

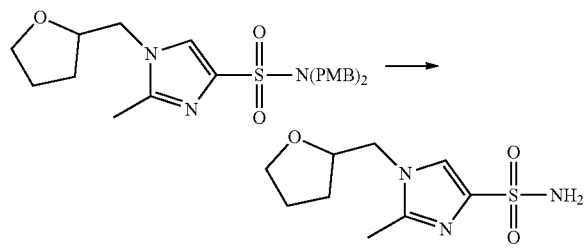

Prepared as described for 1-isopropyl-2-methyl-1H-imidazole-4-sulfonamide (Intermediate P9, Step C) using N,N-bis(4-methoxybenzyl)-2-methyl-1-((tetrahydrofuran-2-yl)methyl)-1H-imidazole-4-sulfonamide (0.2 g, 042 mmol) to afford the title compound (45 mg, 45%) as a white solid.

$^1$H NMR (CD3OD): δ 7.56 (s, 1H), 4.11 (m, 2H), 3.96 (dd, 1H), 3.80 (m, 2H), 2.40 (s, 3H), 2.07 (m, 1H), 1.89 (m, 2H), 1.61 (m, 1H).

Intermediate P12: 1-(2-Hydroxyethyl)-2-methyl-1H-imidazole-4-sulfonamide

Step A: 1-(2-((tert-Butyldimethylsilyl)oxy)ethyl)-N,N-bis(4-methoxybenzyl)-2-methyl-1H-imidazole-4-sulfonamide

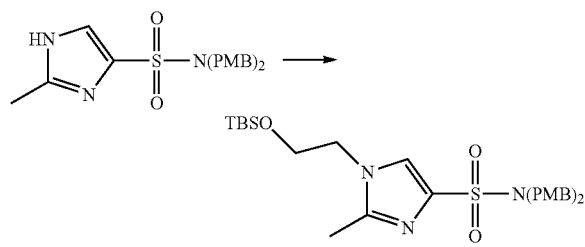

Prepared as described for 1-isopropyl-N,N-bis(4-methoxybenzyl)-2-methyl-1H-imidazole-4-sulfonamide (Intermediate P9, Step B) using N,N-bis(4-methoxybenzyl)-2-methyl-1H-imidazole-4-sulfonamide (Intermediate P9, Step A) (0.28 g, 0.64 mmol) and (2-bromoethoxy)(tert-butyl)dimethylsilane (600 mg, 2.5 mmol) to afford the title compound (350 mg, 100%).

$^1$H NMR (CDCl$_3$) δ 7.40 (s, 1H), 7.10 (d, 4H), 6.76 (d, 4H), 4.29 (s, 4H), 3.97 (t, 2H), 3.86 (t, 2H), 3.78 (s, 6H), 2.45 (s, 3H), 0.84 (s, 9H), −0.03 (s, 6H).

Step B: 1-(2-Hydroxyethyl)-N,N-bis(4-methoxybenzyl)-2-methyl-1H-imidazole-4-sulfonamide

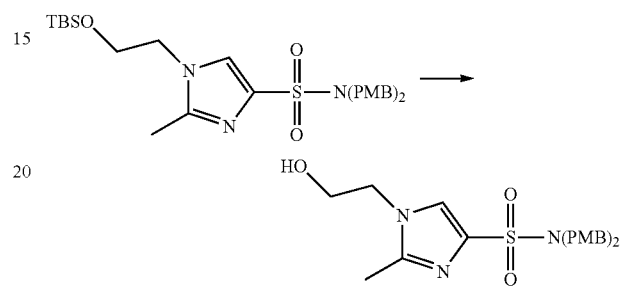

1-(2-((tert-Butyldimethylsilyl)oxy)ethyl)-N,N-bis(4-methoxybenzyl)-2-methyl-1H-imidazole-4-sulfonamide (350 mg, 0.63 mmol) was dissolved in DCM (10 mL). Tetrabutylammonium fluoride (0.60 g, 1.90 mmol) was added and the mixture was stirred overnight at room temperature. The DCM layer was washed with brine, dried, filtered and evaporated to afford the title compound, which was used as such for the next step.

Step C: 1-(2-Hydroxyethyl)-2-methyl-1H-imidazole-4-sulfonamide

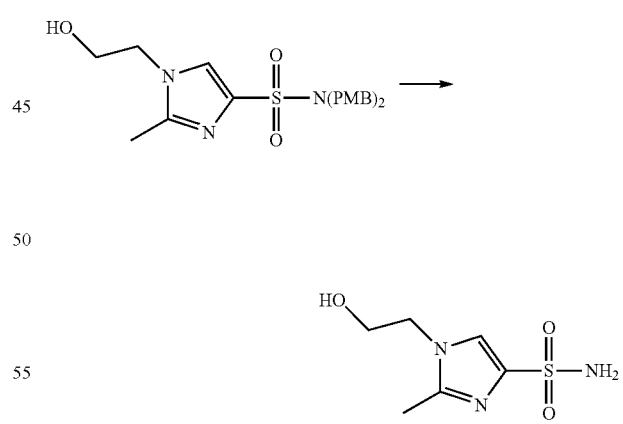

Prepared as described for 1-isopropyl-2-methyl-1H-imidazole-4-sulfonamide (Intermediate P9, Step C) using 1-(2-hydroxyethyl)-N,N-bis(4-methoxybenzyl)-2-methyl-1H-imidazole-4-sulfonamide (0.28 g, 0.64 mmol) to afford the title compound (340 mg, 100%) as a solid, still containing inorganic salts.

$^1$H NMR (CD3OD) δ 7.59 (s, 1H), 4.07 (t, 2H), 3.81 (t, 2H), 2.42 (s, 3H).

Intermediate A1: 4-Isocyanato-1,2,3,5,6,7-hexahydro-s-indacene

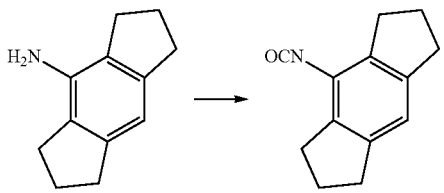

To a solution of phosgene (4.45 mL, 20% weight in toluene, 8.4 mmol) in EtOAc (90 mL) was added dropwise a solution of 1,2,3,5,6,7-hexahydro-s-indacen-4-amine (589 mg, 3.4 mmol) in EtOAc (45 mL) at ambient temperature. The resulting reaction mixture was then heated to reflux for 3 hours and upon cooling was filtered and concentrated in vacuo to afford the title compound as a brown oil (756 mg, 100%). The crude product was used directly in the next step without further purification.

$^1$H NMR (CDCl$_3$) δ 6.8 (s, 1H), 2.89 (m, 8H) and 2.09 (m, 4H).

Intermediate A2: 2-Isocyanato-1,3-diisopropylbenzene

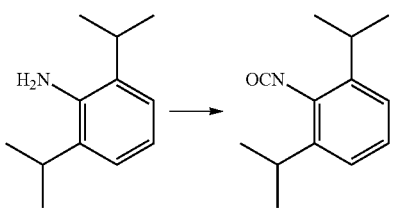

2,6-Diisopropylaniline (3.07 g, 17.14 mmol) was dissolved in dry THF (40 mL) and Et$_3$N (3 mL, 21.52 mmol) was added. A solution of triphosgene (4.26 g, 14.35 mmol) in dry THF (12 mL) was added over 5 minutes, resulting in the formation of a thick colourless precipitate. The reaction mixture was stirred at room temperature overnight. The THF was removed in vacuo and toluene (50 mL) was added. The mixture was filtered through a short silica plug eluting with toluene (150 mL). The filtrate was concentrated in vacuo to afford the title compound (2.76 g, 92%) as a colourless oil.

$^1$H NMR (CDCl$_3$) δ 7.20-7.10 (m, 3H), 3*22 (hept, J=6.9 Hz, 2H), 1.26 (d, J=6.8 Hz, 12H).

Intermediate A2: 4-Fluoro-2-isopropyl-6-(2-methoxypyridin-4-yl)aniline

Step A: 2-Bromo-4-fluoro-6-iso-propylaniline

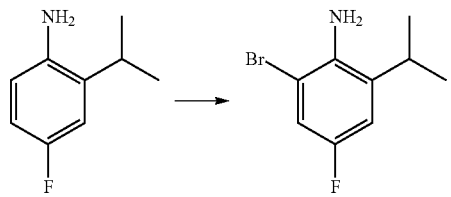

N-Bromosuccinimide (5.64 g, 31.7 mmol) was added portionwise to 4-fluoro-2-isopropylaniline (4.62 g, 30.2 mmol) in DCM (72 mL) at 0° C. The resulting mixture was stirred at 0° C. for 1 hour and then left to warm to room temperature over 21 hours. The reaction mixture was washed with a solution of aqueous sodium hydroxide (2 M, 2×50 mL), dried (MgSO$_4$), filtered and concentrated in vacuo to give a brown residue. The brown residue was put onto a plug of silica (50 g) and washed through with 50% DCM in iso-hexane (500 mL). The red filtrate was concentrated to dryness and the crude product was purified by chromatography on silica gel (120 g column, 0-10% DCM/iso-hexane) to afford the title compound (4.99 g, 70%) as a red oil.

$^1$H NMR (CDCl$_3$) δ 7.07 (dd, 1H), 6.86 (dd, 1H), 4.14 (s, 2H), 2.93 (sep, 1H) and 1.25 (d, 6H).

LCMS m/z 232.2/234.3 (M+H)$^+$ (ES$^+$).

Step B: 4-Fluoro-2-isopropyl-6-(2-methoxypyridin-4-yl)aniline

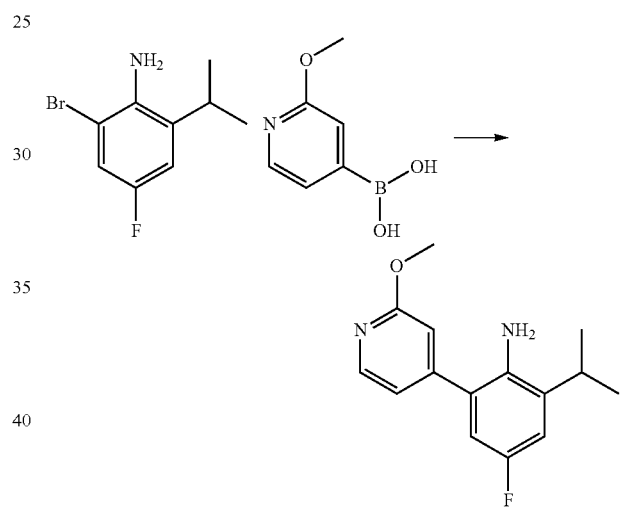

(2-Methoxypyridin-4-yl)boronic acid (144 mg, 0.938 mmol) was added to a stirred, N$_2$-degassed mixture of 2-bromo-4-fluoro-6-isopropylaniline (200 mg, 0.853 mmol), Pd(dppf)Cl$_2$ (31.2 mg, 0.043 mmol) and potassium carbonate (354 mg, 2.56 mmol) in 1,4-dioxane:water (10:1, 6.6 mL). The reaction mixture was then heated to 80° C. under an N$_2$ atmosphere for 22.5 hours. The reaction mixture was left to cool to room temperature and poured onto EtOAc (10 mL) and water (5 mL). The organic layer was collected and the aqueous layer extracted with EtOAc (2×10 mL). The combined organic layers were dried (Na$_2$SO$_4$), filtered and evaporated to dryness. The crude product was purified by chromatography on silica gel (24 g column, 0-50% EtOAc/isohexane) to afford the title compound (174 mg, 78%) as a light brown solid.

$^1$H NMR (CDCl$_3$) δ 8.25 (d, J=5.3 Hz, 1H), 7.00 (dd, J=5.3, 1.4 Hz, 1H), 6.93 (dd, J=9.9, 2.9 Hz, 1H), 6.85 (s, 1H), 6.71 (dd, J=8.6, 3.0 Hz, 1H), 4.01 (s, 3H), 2.92 (hept, J=6.9 Hz, 1H), 1.28 (d, J=6.8 Hz, 6H). Exchangeable NH$_2$ signal seen as broad hump from 4.5-0.5 ppm.

LCMS m/z 261.1 (M+H)$^+$ (ES$^+$).

Intermediate A4: 4-Fluoro-2-isopropyl-6-(i-methyl-1H-pyrazol-4-yl)aniline

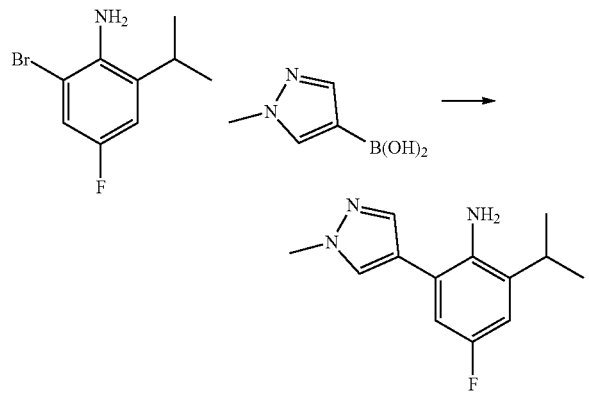

To a sealed vial was added 2-bromo-4-fluoro-6-isopropylaniline (Intermediate A3, Step A) (350 mg, 1.508 mmol) in DMF (15 mL), followed by the addition of (1-methyl-1H-pyrazol-4-yl)boronic acid (190 mg, 1.508 mmol), Pd(PPh$_3$)$_4$ (174 mg, 0.151 mmol) and aqueous 2.0M Na$_2$CO$_3$ (3 mL). The reaction mixture is heated under argon at 100° C. overnight. The residue was diluted with EtOAc (20 mL), washed with brine (20 mL), dried over anhydrous Na$_2$SO$_4$, filtered and concentrated. The crude product was purified by chromatography on silica gel (40 g column, 0-60% EtOAc/isohexane) to afford the title compound (85 mg, 23%) as a brown oil.

$^1$H NMR (CDCl$_3$) δ 7.68 (d, 1H), 7.58 (d, 1H), 6.86 (dd, 1H), 6.78 (dd, 1H), 3.99 (s, 3H), 3.74 (br s, 2H), 2.94 (sept, 1H), 1.29 (d, 6H).

Intermediate A5: d-(2-Amino-5-fluoro-3-isopropylphenyl)picolinonitrile

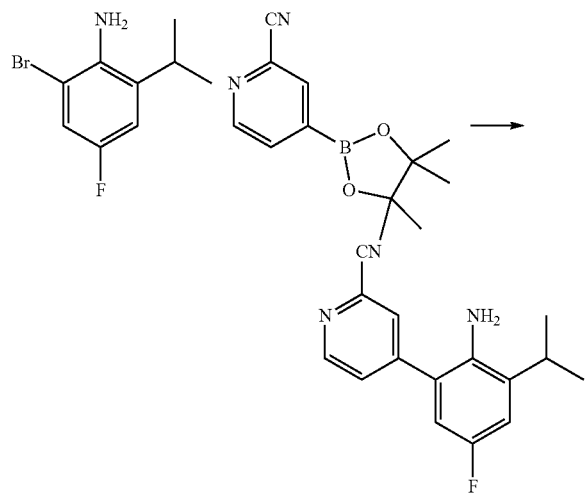

4-(4,4,5,5-Tetramethyl-1,3,2-dioxaborolan-2-yl)picolinonitrile (1 g, 4.35 mmol), 2-bromo-4-fluoro-6-isopropylaniline (Intermediate A3, Step A) (1 g, 4.31 mmol) and potassium carbonate (2 g, 14.47 mmol) were suspended in a mixture of dioxane (10 mL) and water (1 mL). After degassing with nitrogen for 15 minutes, Pd(dppf)Cl$_2$·DCM (150 mg, 0.184 mmol) was added and the mixture was heated to 90° C. overnight, after which time complete consumption of starting bromide was seen. The mixture was cooled to room temperature and diluted with EtOAc (10 mL) and water (5 mL). The organic phase was separated, dried (MgSO$_4$), filtered and concentrated in vacuo to give a brown oil. The crude product was purified by chromatography (Companion apparatus, 40 g column, 0-5% MeOH/DCM) to afford the product as a pale brown oil. The bulk material was further purified by SCX. It was dissolved in methanol (10 mL) and SCX (0.84 meq, 8 g, 3 eq) was added. It was stirred overnight, filtered and washed first with MeOH (100 mL) and then 0.7 M NH$_3$ in methanol (100 mL). The ammoniacal fractions were concentrated in vacuo to afford the title compound (0.484 g, 42%) as a pale yellow oil.

$^1$H NMR (CDCl$_3$) δ 8.79 (dd, J=5.1, 0.9 Hz, 1H), 7.87 (dd, J=1.7, 0.9 Hz, 1H), 7.67 (dd, J=5.1, 1.7 Hz, 1H), 7.01 (dd, J=9.8, 2.9 Hz, 1H), 6.71 (dd, J=8.4, 2.9 Hz, 1H), 3.62 (br s, 2H), 2.95 (sept, J=6.8 Hz, 1H) and 1.32 (d, J=6.8 Hz, 6H).

m/z 256.4 (M+H)$^+$ (ES$^+$).

PREPARATION OF EXAMPLES

Example 1: (R)—N-((1,2,3,5,6,7-Hexahydro-s-indacen-4-yl)carbamoyl)-1-(2-hydroxypropyl)-1H-imidazole-4-sulfonamide

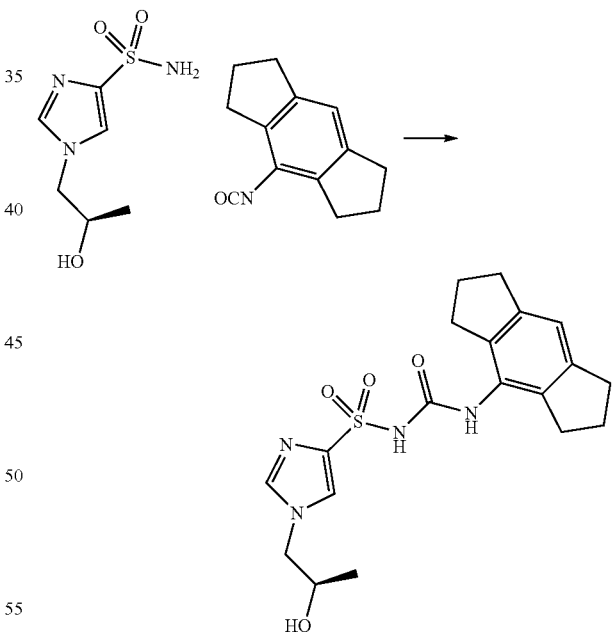

To a solution of (R)-1-(2-hydroxypropyl)-1H-imidazole-4-sulfonamide (Intermediate P1) (120 mg, 0.573 mmol) in THF (2 mL) was added sodium tert-butoxide (2M in THF) (0.3 mL, 0.600 mmol) and the mixture was stirred at room temperature for 1 hour. 4-Isocyanato-1,2,3,5,6,7-hexahydro-s-indacene (Intermediate A1) (120 mg, 0.602 mmol) in THF (2 mL) was added and the mixture was stirred at room temperature overnight. The volatiles were evaporated, the residue dissolved in DMSO and purified by prep-HPLC to afford the title compound (29 mg, 12%) as a white solid.

¹H NMR (DMSO-d₆) δ 8.02 (s, 1H), 7.79 (d, J=1.3 Hz, 1H), 7.76 (d, J=1.3 Hz, 1H), 6.90 (s, 1H), 5.01 (d, J=4.1 Hz, 1H), 4.05-3.96 (m, 1H), 3.92-3.82 (m, 2H), 2.77 (t, J=7.4 Hz, 4H), 2.59 (t, J=7.4 Hz, 4H), 1.93 (p, J=7.4 Hz, 4H), 1.01 (d, J=5.8 Hz, 3H). One exchangeable proton not visible. LCMS; m/z 405.3 (M+H)⁺ (ES⁺).

Example 2: (S)—N-((1,2,3,5,6,7-Hexahydro-s-indacen-4-yl)carbamoyl)-1-(2-hydroxypropyl)-1H-imidazole-4-sulfonamide

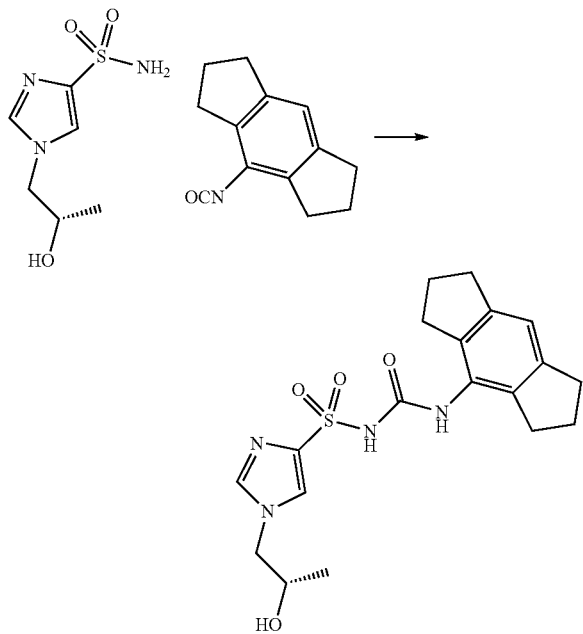

Prepared according to the general procedure of (R)—N-((1,2,3,5,6,7-hexahydro-s-indacen-4-yl)carbamoyl)-1-(2-hydroxypropyl)-1H-imidazole-4-sulfonamide (Example 1) from (S)-1-(2-hydroxypropyl)-1H-imidazole-4-sulfonamide (Intermediate P2) and 4-isocyanato-1,2,3,5,6,7-hexahydro-s-indacene (Intermediate A1) to afford the title compound (13 mg, 13%) as a white solid.

¹H NMR (DMSO-d₆) δ 8.75 (br s, 1H), 7.98 (s, 1H), 7.73 (s, 2H), 6.88 (s, 1H), 5.01 (d, J=4.1 Hz, 1H), 4.08-3.93 (m, 1H), 3.92-3.79 (m, 2H), 2.77 (t, J=7.4 Hz, 4H), 2.60 (t, J=7.4 Hz, 4H), 1.93 (p, J=7.4 Hz, 4H), 1.01 (d, J=5.8 Hz, 3H). LCMS; m/z 405.3 (M+H)⁺ (ES⁺).

Example 3: 1-(2-(Dimethylamino)ethyl)-N-((1,2,3,5,6,7-hexahydro-s-indacen-4-yl)carbamoyl)-1H-imidazole-4-sulfonamide

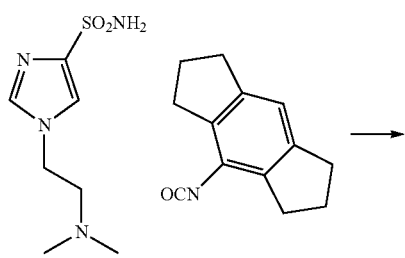

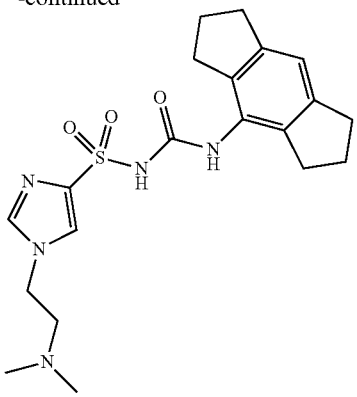

To a solution of 1-(2-(dimethylamino)ethyl)-1H-imidazole-4-sulfonamide (Intermediate P3) (105 mg, 0.481 mmol) in THF (2.5 mL) was added sodium tert-butoxide (2M in THF) (0.3 mL, 0.600 mmol) and the reaction mixture was stirred at room temperature for 1 hour. 4-Isocyanato-1,2,3,5,6,7-hexahydro-s-indacene (Intermediate A1) (105 mg, 0.527 mmol) in THF (2.5 mL) was added and the reaction mixture was stirred at room temperature overnight. The volatiles were removed in vacuo, the residue dissolved in DMSO (2 mL) and purified by prep-HPLC to afford the title compound (44 mg, 22%) as a white solid.

¹H NMR (DMSO-d₆) δ 8.06 (s, 1H), 7.93 (d, J=1.3 Hz, 1H), 7.86 (d, J=1.3 Hz, 1H), 6.92 (s, 1H), 4.11 (t, J=6.2 Hz, 2H), 2.78 (t, J=7.4 Hz, 4H), 2.63-2.55 (m, 6H), 2.17 (s, 6H), 1.94 (p, J=7.4 Hz, 4H). One exchangeable proton not visible. LCMS; m/z 418.4 (M+H)⁺ (ES⁺).

Example 4: N-((2-(2-Cyanopyridin-4-yl)-4-fluoro-6-isopropylphenyl) carbamoyl)-1-isopropyl-1H-imidazole-4-sulfonamide

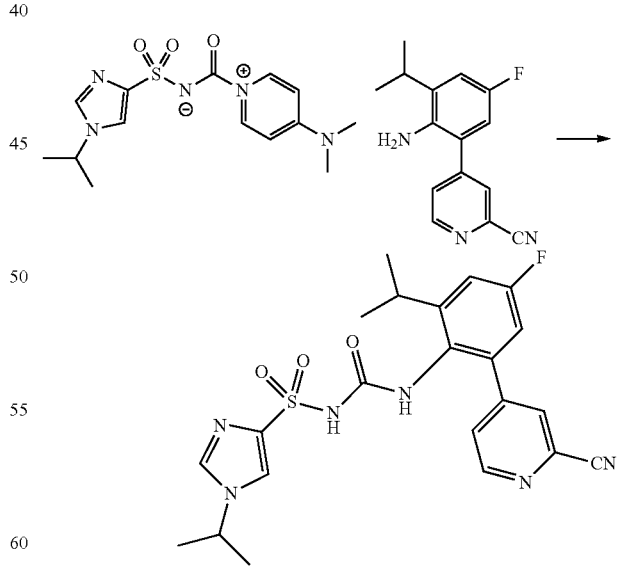

4-(2-Amino-5-fluoro-3-isopropylphenyl)picolinonitrile (Intermediate A5) (38 mg, 0.149 mmol) was added to (4-(dimethylamino)pyridin-1-ium-1-carbonyl)((1-isopropyl-1H-imidazol-4-yl)sulfonyl)amide (Intermediate P4) (50 mg, 0.148 mmol) in MeCN (1 mL) and the mixture was stirred at 50° C. for 2 hours. The crude product was purified by reversed phase prep-HPLC (General Methods, basic prep) to afford the title compound (19 mg, 27%) as a white solid.

$^1$H NMR (DMSO-d$_6$) δ 10.78 (bs, 1H), 8.68 (d, J=5.1 Hz, 1H), 8.02 (s, 2H), 7.89 (s, 1H), 7.82 (s, 1H), 7.63 (d, J=5.0 Hz, 1H), 7.28 (dd, J=10.1, 3.0 Hz, 1H), 7.16 (dd, J=8.8, 3.0 Hz, 1H), 4.46 (sept, J=6.9 Hz, 1H), 3.13-3.01 (m, 1H), 1.41 (d, J=6.7 Hz, 6H), 1.10 (d, J=6.2 Hz, 6H).

LCMS m/z 471.2 (M+H)+ (ES+).

Example 5: N-((4-Fluoro-2-isopropyl-6-(2-methoxy-pyridin-4-yl)phenyl) carbamoyl)-1-isopropyl-1H-imidazole-4-sulfonamide

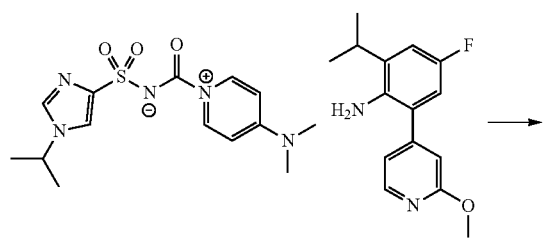

Prepared according to the general procedure of N-((2-(2-cyanopyridin-4-yl)-4-fluoro-6-isopropylphenyl)carbamoyl)-1-isopropyl-1H-imidazole-4-sulfonamide (Example 4) from 4-fluoro-2-isopropyl-6-(2-methoxypyridin-4-yl)aniline (Intermediate A3) (39 mg, 0.150 mmol) and (4-(dimethylamino)pyridin-1-ium-1-carbonyl)((1-isopropyl-1H-imidazol-4-yl)sulfonyl)amide (Intermediate P4) (50 mg, 0.148 mmol) to afford the title compound (20 mg, 28%) as a colourless solid.

$^1$H NMR (DMSO-d$_6$) δ 10.55 (bs, 1H), 8.09 (d, J=5.3 Hz, 1H), 7.95 (s, 1H), 7.90 (s, 1H), 7.80 (s, 1H), 7.21 (dd, J=10.0, 3.0 Hz, 1H), 7.03 (dd, J=8.9, 3.0 Hz, 1H), 6.83 (d, J=5.3 Hz, 1H), 6.74 (s, 1H), 4.48 (sept, J=6.1 Hz, 1H), 3.88 (s, 3H), 3.02-2.93 (m, 1H), 1.41 (d, J=6.7 Hz, 6H), 1.16-0.95 (m, 6H).

LCMS m/z 476.6 (M+H)+ (ES+).

Example 6: 1-Ethyl-N-((1,2,3,5,6,7-hexahydro-s-indacen-4-yl)carbamoyl)-2-methyl-1H-imidazole-4-sulfonamide, potassium salt

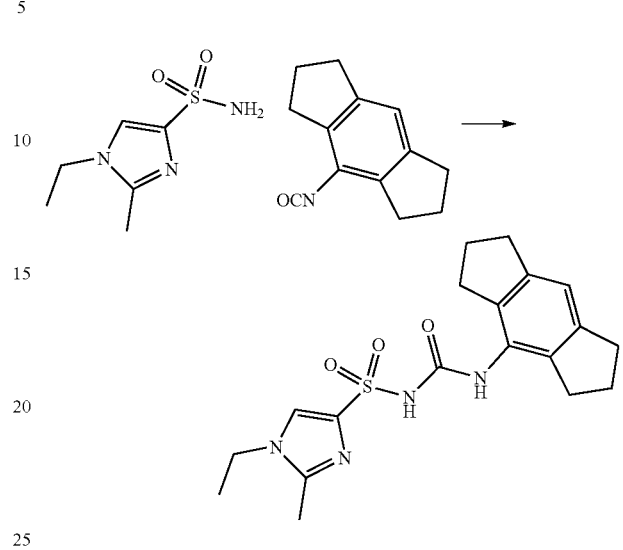

Prepared as described for N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 1-ethyl-2-methyl-1H-imidazole-4-sulfonamide (Intermediate P10) to afford the title compound (70%) as a white solid.

$^1$H NMR (Methanol-d4) δ 7.45 (s, 1H), 6.85 (s, 1H), 3.96 (q, 2H), 2.76 (m, 8H), 2.36 (s, 3H), 1.99 (m, 4H), 1.37 (t, 3H).

LCMS m/z 389 (M+H)+ (ES+); 387 (M−H)− (ES−).

Example 7: N-((1,2,3,5,6,7-Hexahydro-s-indacen-4-yl)carbamoyl)-1-isopropyl-2-methyl-1H-imidazole-4-sulfonamide, potassium salt

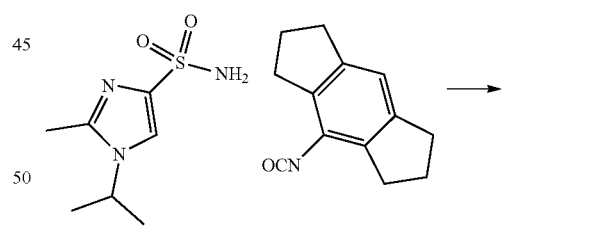

Prepared as described for N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 1-isopropyl-2-methyl-1H-imidazole-4-sulfonamide (Intermediate P9) to afford the title compound (47%) as a white solid.

$^1$H NMR (Methanol-d4) δ 7.54 (s, 1H), 6.84 (s, 1H), 4.50-4.27 (m, 1H), 2.76 (m, 8H), 2.37 (s, 3H), 1.98 (m, 4H), 1.42 (d, 6H).

LCMS m/z 403 (M+H)+ (ES+); 401 (M–H)– (ES–).

Example 8: N-((1,2,3,5,6,7-Hexahydro-s-indacen-4-yl)carbamoyl)-2-isopropyl-1-methyl-1H-imidazole-5-sulfonamide, potassium salt

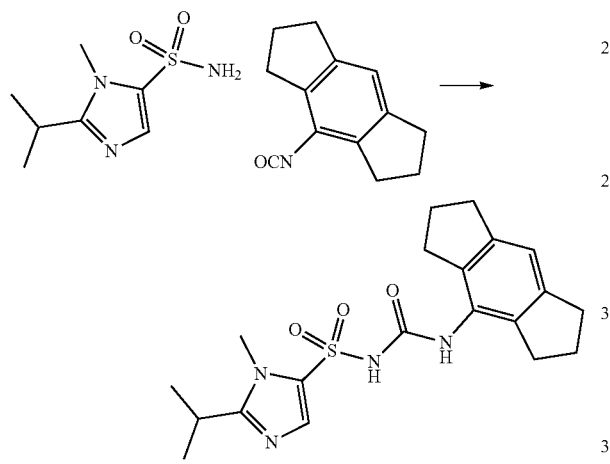

Prepared as described N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 2-isopropyl-1-methyl-1H-imidazole-5-sulfonamide (Intermediate P7) to afford the title compound (57%) as a white solid.

$^1$H NMR (Methanol-d4) δ 7.30 (s, 1H), 6.85 (s, 1H), 3.86 (s, 3H), 3.19-3.04 (m, 1H), 2.91-2.52 (m, 8H), 2.10-1.83 (m, 4H), 1.29 (d, 6H).

LCMS m/z 403 (M+H)+ (ES+); 401 (M–H)– (ES–).

Example Q: N-((1,2,3,5,6,7-Hexahydro-s-indacen-4-yl)carbamoyl)-1-methyl-1H-imidazole-2-sulfonamide, potassium salt

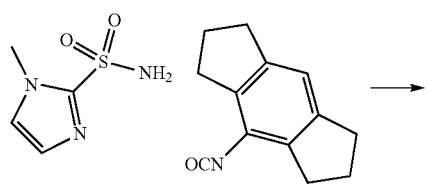

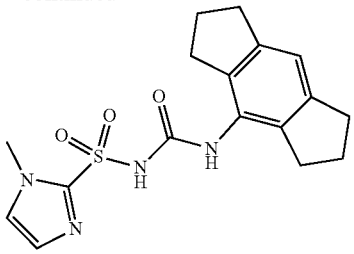

Prepared as described for N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 1-methyl-1H-imidazole-2-sulfonamide to afford the title compound (62%) as a white solid.

$^1$H NMR (Methanol-d4) δ 7.13 (s, 1H), 6.93 (s, 1H), 6.85 (s, 1H), 3.96 (s, 3H), 2.73 (m, 8H), 1.97 (m, 4H).

LCMS m/z 361 (M+H)+ (ES+); 359 (M–H)– (ES–).

Example 10: N-((4-Fluoro-2-isopropyl-6-(i-methyl-1H-pyrazol-4-yl) phenyl)carbamoyl)-1-isopropyl-1H-imidazole-4-sulfonamide

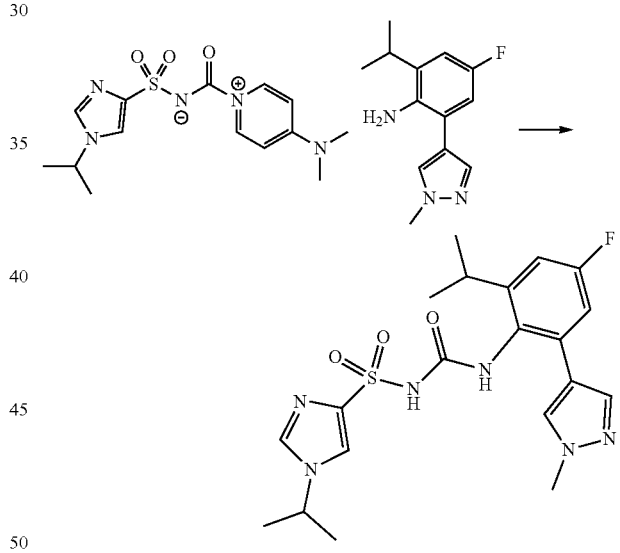

Prepared according to the general procedure of N-((2-(2-cyanopyridin-4-yl)-4-fluoro-6-isopropylphenyl)carbamoyl)-1-isopropyl-1H-imidazole-4-sulfonamide (Example 4) from 4-fluoro-2-isopropyl-6-(2-methoxypyridin-4-yl)aniline (Intermediate A4) (34.6 mg, 0.148 mmol) and (4-(dimethylamino)pyridin-1-ium-1-carbonyl)((1-isopropyl-1H-imidazol-4-yl)sulfonyl)amide (Intermediate P4) (50 mg, 0.148 mmol) to afford the title compound (24.9 mg, 37%) as a colourless solid.

$^1$H NMR (DMSO-d$_6$) δ 7.95 (s, 1H), 7.90 (s, 1H), 7.81 (s, 1H), 7.68 (s, 1H), 7.68-7.64 (m, 1H), 7.14 (dd, J=9.9, 3.0 Hz, 1H), 6.94 (dd, J=10.0, 3.0 Hz, 1H), 4.44 (sept, J=6.3 Hz, 1H), 3.87 (s, 3H), 3.14-2.87 (m, 1H), 1.38 (d, J=6.7 Hz, 6H), 1.04 (d, J=6.8 Hz, 6H). NH not observed.

LCMS m/z 449.4 (M+H)+ (ES+).

Example 11: N-((1,2,3,5,6,7-Hexahydro-s-indacen-,4-yl)carbamoyl)-1,2-dimethyl-1H-imidazole-4-sulfonamide

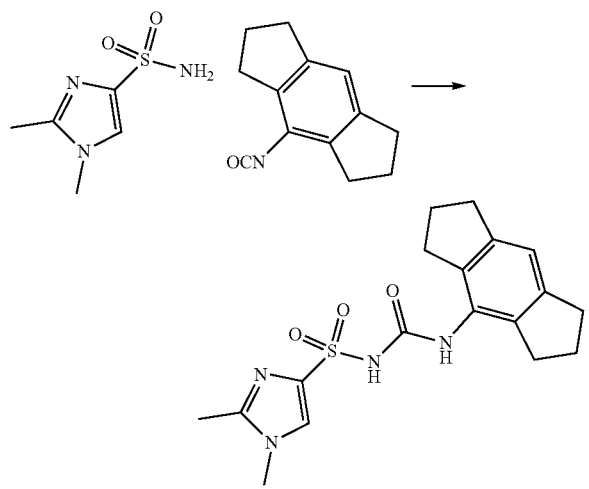

Prepared according to the general procedure of (R)—N-((1,2,3,5,6,7-hexahydro-s-indacen-4-yl)carbamoyl)-1-(2-hydroxypropyl)-1H-imidazole-4-sulfonamide (Example 1) from 1,2-dimethyl-1H-imidazole-4-sulfonamide and 4-isocyanato-1,2,3,5,6,7-hexahydro-s-indacene (Intermediate A1) to afford the title compound (14 mg, 15%) as a white solid.

$^1$H NMR (DMSO-d$_6$) δ 10.48 (br s, 1H), 8.10 (s, 1H), 7.82 (s, 1H), 6.94 (s, 1H), 3.35 (s, 3H), 2.79 (t, J=7.4 Hz, 4H), 2.59 (t, J=7.3 Hz, 4H), 2.32 (s, 3H), 1.99-1.92 (m, 4H).
LCMS m/z 375 (M+H)$^+$ (ES$^+$).

Example 12: N-((1,2,3,5,6,7-Hexahydro-s-indacen-4-yl)carbamoyl)-1-methyl-1H-imidazole-4-sulfonamide

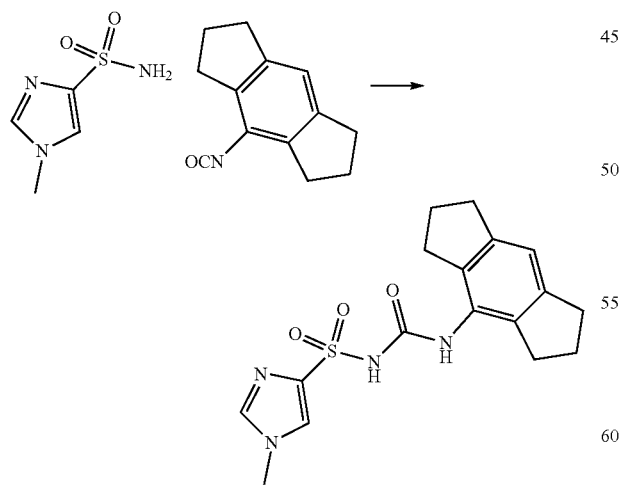

Prepared according to the general procedure of (R)—N-((1,2,3,5,6,7-hexahydro-s-indacen-4-yl)carbamoyl)-1-(2-hydroxypropyl)-1H-imidazole-4-sulfonamide (Example 1) from 1-methyl-1H-imidazole-4-sulfonamide and 4-isocyanato-1,2,3,5,6,7-hexahydro-s-indacene (Intermediate A1) to afford the title compound (21 mg, 24%) as a white solid.

$^1$H NMR (DMSO-d$_6$) δ 10.58 (br s, 1H), 8.05 (s, 1H), 7.89 (s, 1H), 7.83 (s, 1H), 6.93 (s, 1H), 3.70 (s, 3H), 2.78 (t, J=7.4 Hz, 4H), 2.58 (t, J=7.4 Hz, 4H), 1.97-1.90 (m, 4H).
LCMS m/z 361 (M+H)$^+$ (ES$^+$).

Example 13: N-((1,2,3,5,6,7-Hexahydro-s-indacen-4-yl)carbamoyl)-2-isopropyl-1-methyl-1H-imidazole-4-sulfonamide, potassium salt

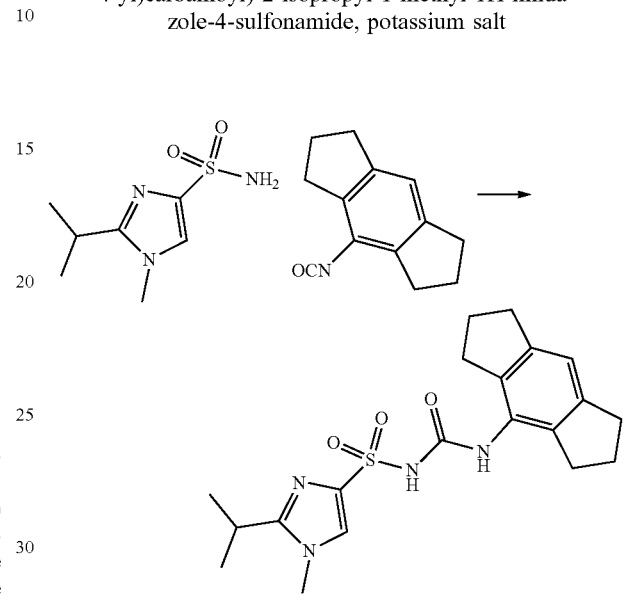

To a solution of 2-isopropyl-1-methyl-1H-imidazole-4-sulfonamide (Intermediate P8) (85 mg, 0.42 mmol) in THF (3 mL) was added potassium tert-butoxide (47 mg, 0.42 mmol). The mixture was stirred for 40 minutes. A solution of 4-isocyanato-1,2,3,5,6,7-hexahydro-s-indacene (Intermediate A1) (83 mg, 0.41 mmol) in THF (1 mL) was added and the mixture was stirred overnight at room temperature. The reaction mixture was concentrated in vacuo and DMSO (1 mL) was added. The solution (suspensions were filtered first over cotton wool) was submitted for purification by reversed phase column chromatography (see "Experimental Methods") to afford the title compound (44 mg, 26%) as a white solid.

$^1$H NMR (Methanol-d4) δ 7.36 (s, 1H), 6.85 (s, 1H), 3.64 (s, 3H), 3.17-3.01 (m, 1H), 2.75 (m, 8H), 1.99 (m, 4H), 1.29 (d, 6H).
LCMS m/z 403 (M+H)+ (ES+); 401 (M–H)– (ES–).

Example 14: N-((2,6-Diisopropylphenyl)carbamoyl)-1-isopropyl-1H-imidazole-4-sulfonamide, sodium salt

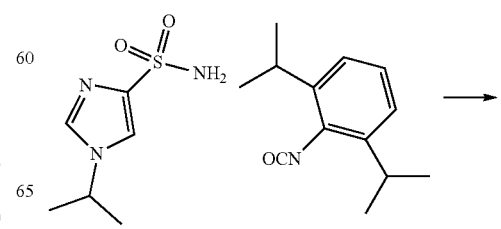

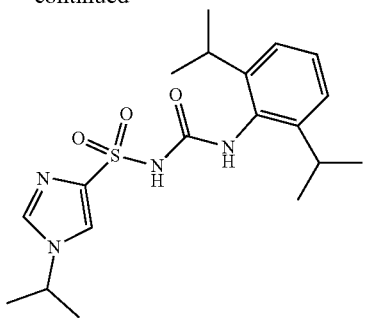

Prepared according to the general procedure of (R)—N-((1,2,3,5,6,7-hexahydro-s-indacen-4-yl)carbamoyl)-1-(2-hydroxypropyl)-1H-imidazole-4-sulfonamide (Example 1) from 1-isopropyl-1H-imidazole-4-sulfonamide and 2-isocyanato-1,3-diisopropylbenzene (Intermediate A2) to afford the title compound (27 mg, 28%) as a colourless solid.

$^1$H NMR (DMSO-d$_6$) δ 7.65 (d, J=1.4 Hz, 1H), 7.45 (br s, 2H), 7.13-7.05 (m, 1H), 7.01 (d, J=7.6 Hz, 2H), 4.44-4.38 (m, 1H), 3.15-3.07 (m, 2H), 1.38 (d, J=6.7 Hz, 6H), and 1.03 (d, J=6.9 Hz, 12H).

LCMS m/z 393 (M+H)$^+$ (ES$^+$).

Example 15: N-((1,2,3,5,6,7-Hexahydro-s-indacen-4-yl)carbamoyl)-1-isopropyl-1H-imidazole-4-sulfonamide, sodium salt

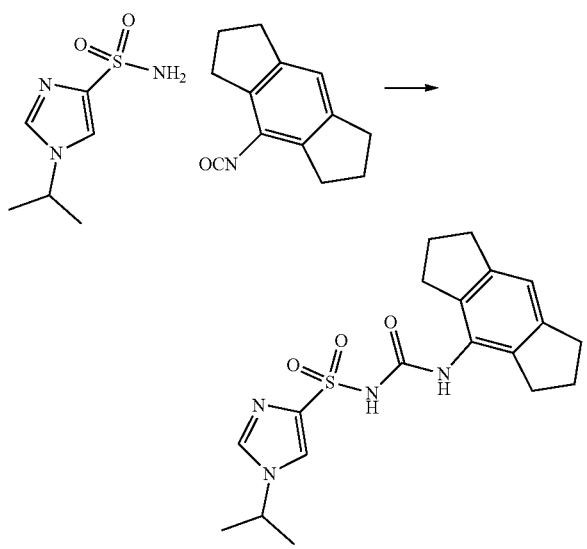

1-Isopropyl-1H-imidazole-4-sulfonamide (35.5 mg, 0.188 mmol) was dissolved in THF (5 mL) and 2 M sodium tert-butoxide in THF (0.098 ml, 0.197 mmol) added. After the mixture had been stirred at room temperature for 1 hour, 4-isocyanato-1,2,3,5,6,7-hexahydro-s-indacene (Intermediate A1) (37.4 mg, 0.188 mmol) was added and the mixture stirred at room temperature for 15 hours. Ethyl acetate (5 mL) was added to the mixture and the suspension filtered and washed with ethyl acetate (1 mL). The collected solid was dried under reduced pressure to afford the title compound (32 mg, 40%) as a white solid.

$^1$H NMR (DMSO-d$_6$) δ 7.67 (d, J=1.5 Hz, 1H), 7.62 (br s, 1H), 7.45 (d, J=1.5 Hz, 1H), 6.77 (s, 1H), 4.45-4.39 (m, 1H), 2.75 (t, J=7.4 Hz, 4H), 2.64 (t, J=7.3 Hz, 4H), 1.93-1.86 (m, 4H), and 1.39 (d, J=6.7 Hz, 6H).

LCMS m/z 389 (M+H)$^+$ (ES$^+$).

Example 16: N-((1,2,3,5,6,7-Hexahydro-s-indacen-4-yl)carbamoyl)-2-methyl-1-((tetrahydrofuran-2-yl)methyl)-1H-imidazole-4-sulfonamide, potassium salt

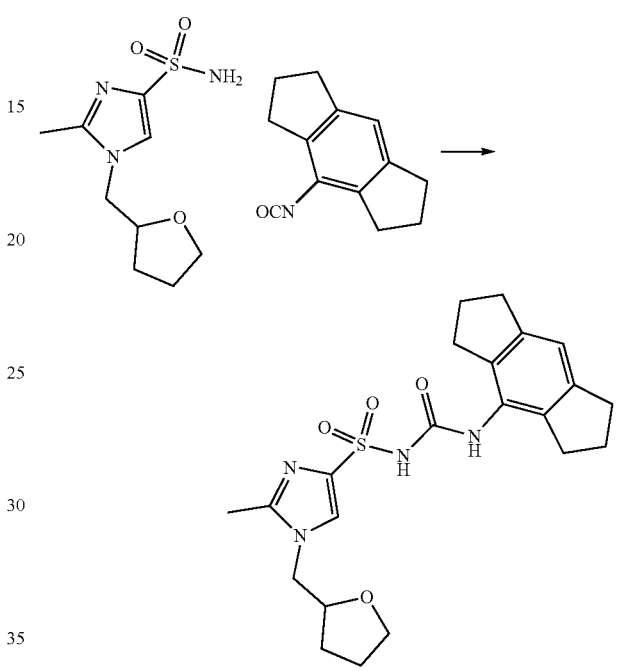

Prepared as described for N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 2-methyl-1-((tetrahydrofuran-2-yl)methyl)-1H-imidazole-4-sulfonamide (Intermediate P11) to afford the title compound (53%) as a white solid.

$^1$H NMR (Methanol-d4) δ 7.49 (s, 1H), 6.85 (s, 1H), 4.18-4.01 (m, 2H), 4.01-3.86 (m, 1H), 3.88-3.59 (m, 2H), 2.76 (m, 9H), 2.38 (s, 3H), 2.18-1.91 (m, 4H), 1.89-1.71 (m, 2H), 1.70-1.41 (m, 1H).

LCMS m/z 445 (M+H)+ (ES+); 443 (M–H)– (ES–).

Example 17: N-((1,2,3,5,6,7-Hexahydro-s-indacen-4-yl)carbamoyl)-1-(2-hydroxyethyl)-2-methyl-1H-imidazole-4-sulfonamide, potassium salt

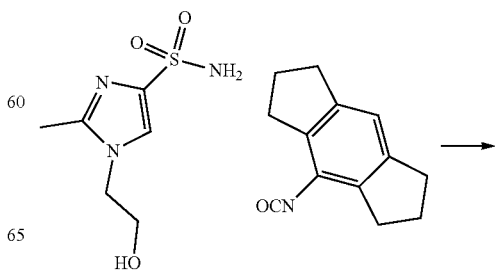

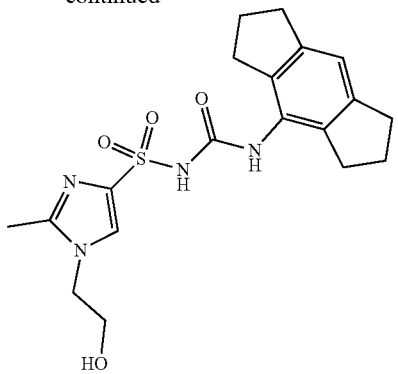

Prepared as described for N-((1,2,3,5,6,7-hexahydro-s-indacen-4-yl)carbamoyl)-2-isopropyl-1-methyl-1H-imidazole-4-sulfonamide, potassium salt (Example 13) using 4-isocyanato-1,2,3,5,6,7-hexahydro-s-indacene (Intermediate A1) and 1-(2-hydroxyethyl)-2-methyl-1H-imidazole-4-sulfonamide (Intermediate P12) and one additional equivalent of KOtBu to afford the title compound (14%) as a white solid.

$^1$H NMR (Methanol-d4) δ 7.60 (s, 1H), 6.90 (s, 1H), 4.04 (d, 2H), 3.80 (t, 2H), 2.94-2.61 (m, 9H), 2.41 (s, 3H), 2.12-1.94 (m, 4H).

LCMS m/z 405 (M+H)+ (ES+).

Example 18: 2-((Dimethylamino)methyl)-N-((1,2,3,5,6,7-hexahydro-s-indacen-4-yl)carbamoyl)-1-methyl-1H-imidazole-4-sulfonamide, and Example 19: 5-((Dimethylaminomethyl)-N-((1,2,2,5,6,7-hexahydro-s-indacen-4-yl)carbamoyl)-1-methyl-1H-imidazole-4-sulfonamide

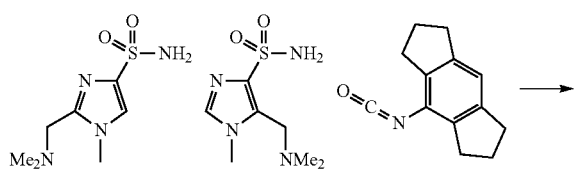

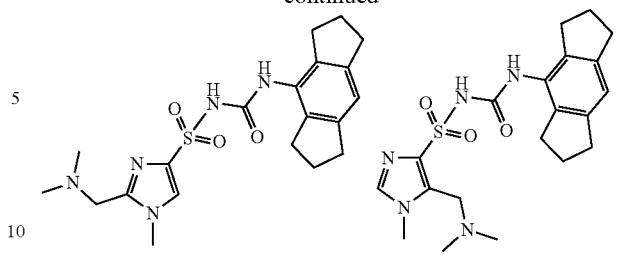

Sodium tert-butoxide, 2 M in THF (0.120 mL, 0.241 mmol) was added to a solution of a mixture of 2-((dimethylamino)methyl)-1-methyl-1H-imidazole-4-sulfonamide and 5-((dimethylamino)methyl)-1-methyl-1H-imidazole-4-sulfonamide (Intermediates P5 and P6) (50 mg, 0.229 mmol) in THF (1 mL) and stirred at room temperature for 1 hour. Then 4-isocyanato-1,2,3,5,6,7-hexahydro-s-indacene (Intermediate A1) (47.9 mg, 0.241 mmol) in THF (1 mL) was added and the reaction stirred at room temperature over the weekend. The reaction mixture was concentrated and the crude product was purified by chromatography (Companion apparatus, RP Flash C18, 12 g column, 5.50% MeCN/10 mM ammonium bicarbonate) to afford 2-((dimethylamino)methyl)-N-((1,2,3,5,6,7-hexahydro-s-indacen-4-yl)carbamoyl)-1-methyl-1H-imidazole-4-sulfonamide (Example 18) (44 mg, 46%) and 5-((dimethylamino)methyl)-N-((1,2,3,5,6,7-hexahydro-s-indacen-4-yl)carbamoyl)-1-methyl-1H-imidazole-4-sulfonamide (Example 19) (3 mg, 3%), both as colourless solids.

Example 18: $^1$H NMR (DMSO-d$_6$) δ 7.91 (s, 1H), 7.77 (s, 1H), 6.83 (s, 1H), 4.26 (s, 2H), 3.67 (s, 3H), 2.76 (t, J=7.4 Hz, 4H), 2.66-2.53 (m, 10H), 1.96-1.84 (m, 4H) (1 exchangeable NH not observed).

LCMS; m/z 418.3 (M+H)$^+$ (ES$^+$).

Example 19: $^1$H NMR (DMSO-d$_6$) δ 10.70 (br s, 1H), 7.96 (s, 1H), 7.80 (s, 1H), 6.90 (s, 1H), 3.68 (s, 3H), 346 (s, 2H), 2.78 (t, J=7.4 Hz, 4H), 2.58 (t, J=7.4 Hz, 4H), 2.14 (s, 6H), 1.99-1.86 (m, 4H).

LCMS; m/z 418.3 (M+H)$^+$ (ES$^+$).

The compounds of examples 20-21 were synthesised by methods analogous to those outlined above.

TABLE 1

| | 1H NMR and MS data | | | |
|---|---|---|---|---|
| Ex | Structure and Name | $^1$H NMR spectrum | MS | MW |
| 20 | N-((5-(2-Cyanopyridin-4-yl)-2,3-dihydro-1H-inden-4-yl)carbamoyl)-1-isopropyl-1H-imidazole-4-sulfonamide | $^1$H NMR (DMSO-d$_6$) δ 8.65 (dd, J = 5.1, 0.8 Hz, 1H), 8.13 (s, 1H), 7.94 (dd, J = 1.8, 0.8 Hz, 1H), 7.87 (s, 1H), 7.77 (s, 1H), 7.60 (dd, J = 5.1, 1.8 Hz, 1H), 7.23 (d, J = 7.7 Hz, 1H), 7.19 (d, J = 7.7 Hz, 1H), 4.46 (sept, J = 6.8 Hz, 1H), 2.93 (t, J = 7.5 Hz, 2H), 2.71 (t, J = 7.5 Hz, 2H), 2.01 (p, J = 7.5 Hz, 2H), 1.42 (d, J = 6.7 Hz, 6H). One NH not observed. | m/z 451.2 (M + H)$^+$ (ES$^+$) | 450.5 |

TABLE 1-continued

1H NMR and MS data

| Ex | Structure and Name | 1H NMR spectrum | MS | MW |
|---|---|---|---|---|
| 21 | 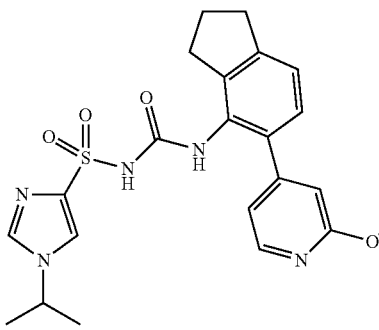<br>1-Isopropyl-N-((5-(2-methoxypyridin-4-yl)-2,3-dihydro-1H-inden-4-yl)carbamoyl)-1H-imidazole-4-sulfonamide | $^1$H NMR (DMSO-$d_6$) δ 8.11 (d, J = 5.3 Hz, 1H), 7.92-7.80 (m, 3H), 7.18 (d, J = 7.7 Hz, 1H), 7.10 (d, J = 7.6 Hz, 1H), 6.83 (d, J = 5.3 Hz, 1H), 6.70 (s, 1H), 4.48 (sept, J = 6.5 Hz, 1H), 3.88 (s, 3H), 2.90 (t, J = 7.4 Hz, 2H), 2.61 (t, J = 7.4 Hz, 2H), 1.96 (p, J = 7.5 Hz, 2H), 1.42 (d, J = 6.6 Hz, 6H). One NH not observed. | m/z 456.3 (M + H)$^+$ (ES$^+$) | 455.5 |

Examples—Biological Studies

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), 62579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~$10^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% $CO_2$
4. Add 5 μl nigericin (Sigma #N7143) (FAC 5 μM) to all wells
5. Incubate for 1 hr at 37° C. and 5% $CO_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

96-Well Plate Map

| | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |

-continued

| 1 | 2 | 3 | 4 | 5 | 6 | 7 | 8 | 9 | 10 | 11 | 12 |
|---|---|---|---|---|---|---|---|---|---|---|---|
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950(10 uM)
Compound 8-point half-log dilution
Low Drug free control

The results of the pyroptosis assay performed are summarised in Table 2 below as THP $IC_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 µl of whole blood containing 1 µg/ml of LPS in 96-well, clear bottom cell culture plate (Corning #3585)
2. Add 10 µl compound (8 points half-log dilution with 10 µM top dose) or vehicle (DMSO 0.1% FAC) to the appropriate wells
3. Incubate for 3 hrs at 37° C. 5% $CO_2$
4. Add 10 µl Nigericin (Sigma #N7143) (10 µM FAC) to all wells
5. Incubate for 1 hr at 37° C. 5% $CO_2$
6. At the end of the incubation period, spin plates at 300×g for 5 mins to pellet cells and remove 20 µl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 2 below as HWB $IC_{50}$.

TABLE 2

| NLRP3 inhibitory activity | | |
|---|---|---|
| Example No | THP $IC_{50}$ | HWB $IC_{50}$ |
| 1 | +++ | *** |
| 2 | +++ | *** |
| 3 | ++ | ** |
| 4 | +++ | **** |
| 5 | ++++ | *** |
| 6 | +++ | * |
| 7 | +++ | ** |
| 8 | +++ | ND |
| 9 | + | ND |
| 10 | + | ND |
| 11 | ++ | ND |
| 12 | ++ | ND |
| 13 | ++ | * |
| 14 | + | ND |
| 15 | +++ | ** |
| 16 | +++ | *** |
| 17 | ++ | *** |
| 18 | + | ND |

TABLE 2-continued

| NLRP3 inhibitory activity | | |
|---|---|---|
| Example No | THP $IC_{50}$ | HWB $IC_{50}$ |
| 19 | +++ | *** |
| 20 | +++++ | ***** |
| 21 | ++++ | **** |

[THP $IC_{50}$ (≤0.04 µM = +++++, ≤0.16 µM = ++++, ≤0.64 µM = +++, ≤2.56 µM = ++, ≤10 µM = +, not determined = ND)]
[HWB $IC_{50}$ (≤0.4 µM = ***, ≤0.8 µM = , ≤1.6 µM = *, ≤3.2 µM = **, ≤10 µM = *, not determined = ND)]

PK Protocol

Pharmacokinetic parameters were determined in male Sprague Dawley rats (Vital River Laboratory Animal Technology Co Ltd, Beijing, China, 7-9 weeks old). Animals were individually housed during the study and maintained under a 12 h light/dark cycle. Animals had free access to food and water.

For intravenous administration, compounds were formulated as a solution in DMSO:PBS [10:90] in 2 mL/kg dosing volume and administered via tail vein.

Serial blood samples (about 200 µL) were taken from each animal at each of 8 time-points post dose (0.083, 0.25, 0.5, 1, 2, 4, 8 and 24 h). Samples were held on ice for no longer than 30 minutes before centrifugation (5,696 rpm (3,000 g) for 15 minutes) for plasma generation. Plasma was frozen on dry ice prior to bioanalysis. PK parameters were generated from LC-MS/MS data using Phoenix WinNonlin 6.3 software.

TABLE 3

| PK data (intravenous administration) | | | | | |
|---|---|---|---|---|---|
| Example No | Dose (mg/kg) | AUC (ng · hr/mL) | $T_{1/2}$ (hr) | $V_{dss}$ (L/kg) | Cl (mL/min/kg) |
| 4 | 1 | 200 | 1.6 | 2.5 | 85.4 |

As is evident from the results presented in Table 2, surprisingly in spite of the structural differences versus the prior art compounds, the compounds of the invention show high levels of NLRP3 inhibitory activity in the pyroptosis assay and in the human whole blood assay.

As is evident from the results presented in Table 3, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

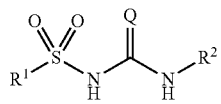

Formula (I)

or a pharmaceutically acceptable salt or solvate thereof, wherein:
- $R^1$ is an imidazolyl group, wherein the imidazolyl group is an imidazol-2-yl group, an imidazol-4-yl group or an imidazol-5-yl group, and wherein the imidazolyl group is substituted with one or more monovalent substituents; and
- $R^2$ is a phenyl or a 5- or 6-membered heteroaryl group, wherein the phenyl or the 5- or 6-membered heteroaryl group is substituted at the α and α' positions, and wherein $R^2$ may optionally be further substituted.

2. The compound or pharmaceutically acceptable salt or solvate thereof, as claimed in claim 1, wherein $R^1$ is an imidazol-4-yl group or an imidazol-5-yl group.

3. The compound or pharmaceutically acceptable salt or solvate thereof, as claimed in claim 1, wherein $R^1$ is an imidazol-2-yl group.

4. The compound or pharmaceutically acceptable salt or solvate thereof, as claimed in claim 1, wherein the imidazolyl group of $R^1$ is substituted with one, two or three substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$_a$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;
- wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and
- wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

5. The compound or pharmaceutically acceptable salt or solvate thereof, as claimed in claim 1, wherein the imidazolyl group of $R^1$ is substituted with one monovalent substituent.

6. The compound or pharmaceutically acceptable salt or solvate thereof, as claimed in claim 1, wherein the imidazolyl group of $R^1$ is substituted with two or three monovalent substituents.

7. The compound or pharmaceutically acceptable salt or solvate thereof, as claimed in claim 1, wherein each monovalent substituent of the imidazolyl group of $R^1$ is independently selected from a saturated hydrocarbyl group, wherein the saturated hydrocarbyl group may be straight-chained or branched, or be or include cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton.

8. The compound or pharmaceutically acceptable salt or solvate thereof, as claimed in claim 1, wherein each monovalent substituent of the imidazolyl group of $R^1$ is acyclic.

9. The compound or pharmaceutically acceptable salt or solvate thereof, as claimed in claim 1, wherein $R^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions and a second cycloalkyl, cycloalkenyl, non-aromatic heterocyclic, aryl or heteroaryl ring is fused to the phenyl or the 5- or 6-membered heteroaryl group across the α',β' positions, and wherein $R^2$ may optionally be further substituted.

10. The compound or pharmaceutically acceptable salt or solvate thereof, as claimed in claim 1, wherein the substituent at the α-position of the phenyl or the 5- or 6-membered heteroaryl group of $R^2$ is a monovalent heterocyclic group or a monovalent aromatic group, wherein a ring atom of the heterocyclic or aromatic group is directly attached to the α-ring atom of the phenyl or the 5- or 6-membered heteroaryl group of $R^2$, wherein the heterocyclic or aromatic group may optionally be substituted, and wherein the cyclic group may optionally be further substituted.

11. The compound or pharmaceutically acceptable salt or solvate thereof, as claimed in claim 1, which is (a) a compound is selected from the group consisting of:

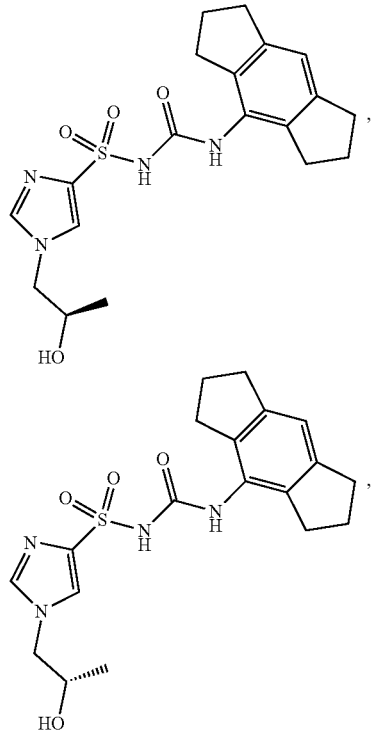

101
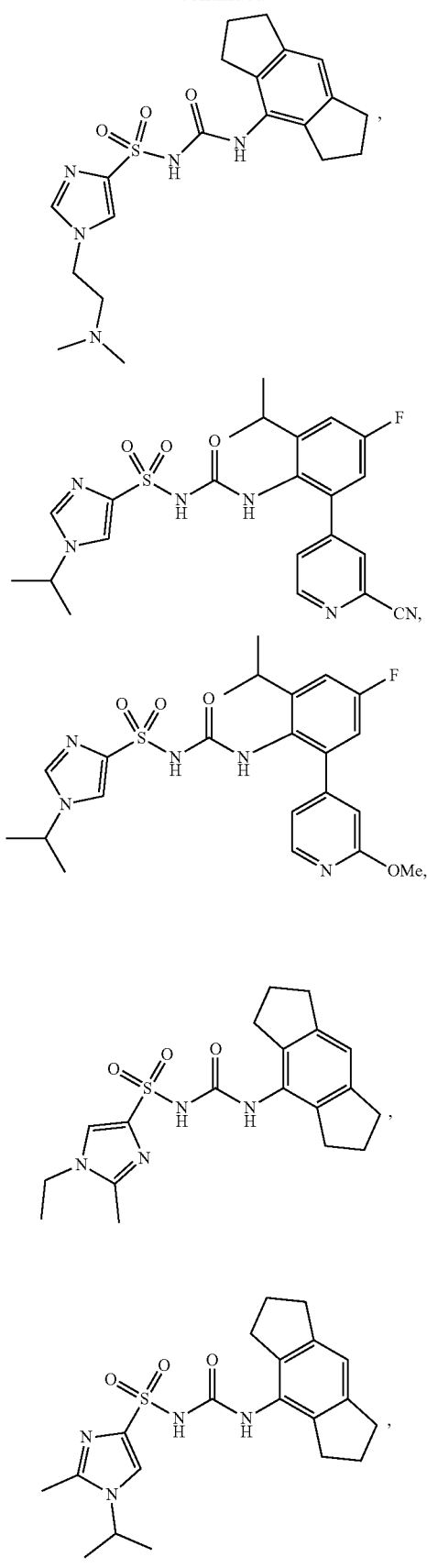
102
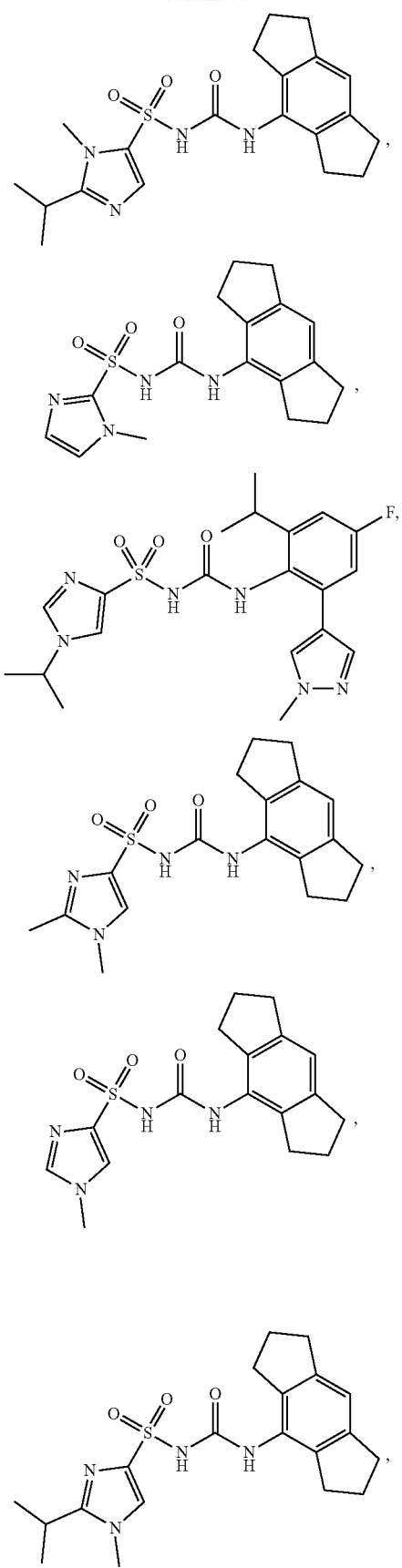

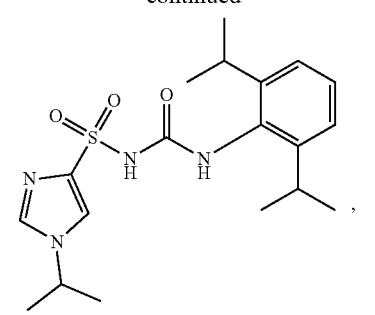
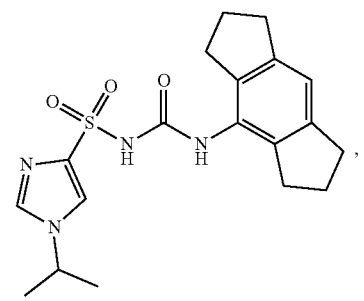
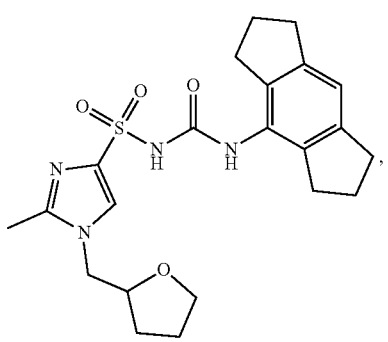
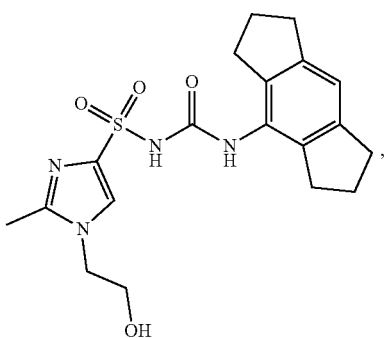
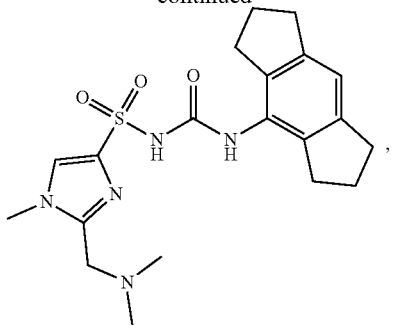
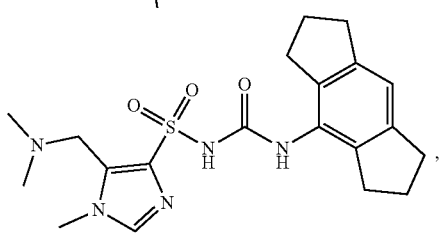
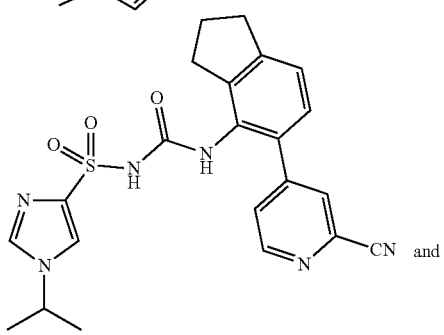
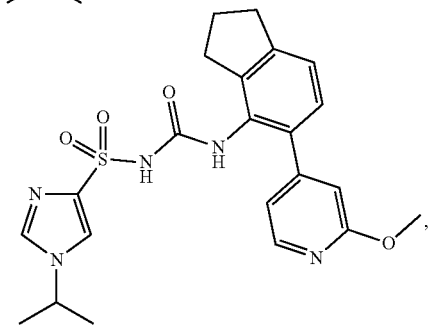
or (b) a pharmaceutically acceptable salt or solvate of the selected compound.
12. A pharmaceutical composition comprising the compound or the pharmaceutically acceptable salt or solvate thereof, as claimed in claim 1, and a pharmaceutically acceptable excipient.
* * * * *